(12) United States Patent
Fitzgerald et al.

(10) Patent No.: US 7,700,724 B2
(45) Date of Patent: Apr. 20, 2010

(54) ISOLATED INSP 163 PROTEIN

(75) Inventors: Stephen Noel Fitzgerald, London (GB); Richard Joseph Fagan, London (GB); Christine Power, Thoiry (FR); Melanie Yorke, Confignon (CH); Jadwiga Bienkowska, Cambridge, MA (US)

(73) Assignee: Ares Trading S.A., Aubonne (CH)

( * ) Notice: Subject to any disclaimer, the term of this patent is extended or adjusted under 35 U.S.C. 154(b) by 528 days.

(21) Appl. No.: 10/573,936

(22) PCT Filed: Oct. 27, 2004

(86) PCT No.: PCT/GB2004/004544
§ 371 (c)(1),
(2), (4) Date: Nov. 13, 2006

(87) PCT Pub. No.: WO2005/042576
PCT Pub. Date: May 12, 2005

(65) Prior Publication Data
US 2007/0072260 A1    Mar. 29, 2007

(30) Foreign Application Priority Data
Oct. 27, 2003    (GB)    .................. 0325038.8

(51) Int. Cl.
C07K 1/00    (2006.01)
C07K 14/00    (2006.01)
C07K 17/00    (2006.01)
C07K 16/00    (2006.01)
C08H 1/00    (2006.01)

(52) U.S. Cl. .................. 530/350; 530/351; 530/402

(58) Field of Classification Search ............ None
See application file for complete search history.

(56) References Cited

FOREIGN PATENT DOCUMENTS

WO    WO 02/20569 A2    3/2002
WO    WO 03/031586 A2    4/2003

OTHER PUBLICATIONS

Skolnick et al. Trends in Biotech. 18:34-39, 2000.*
Bork P. Genome Research 10:398-400, 2000.*
Doerks et al. Trends in Genetics 14:248-250, 1998.*
Smith et al. Nature Biotechnology 15:1222-1223, 1997.*
Brenner SE. Trends in Genetics 15:132-133, 1999.*
Bork, et al. Trends in Genetics 12:425-427, 1996.*
Shapiro, L., and Scherer, P.E., "The crystal structure of a complement-1q family protein suggests an evolutionary link to tumor necrosis factor" *Current Biology*, Mar. 2, 1998, pp. 335-338, vol. 8, No. 6.
Database EMBL Human protein, Mar. 30, 2000, retrieved from EBI accession No. Q5T7M4, Database Accession No. AL162741.
Kishore, U., and Reid, K.B.M., "C1q: structure, function, and receptors" *Immunopharmacology*, Mar. 27, 2000, pp. 159-170, vol. 49.
Database GenBank Human protein, Jan. 22, 2004, retrieved from GenBank accession No. XP_371208, Database Accession No. XM_371208.1.

* cited by examiner

*Primary Examiner*—Robert Landsman
(74) *Attorney, Agent, or Firm*—Saliwanchik, Lloyd & Saliwanchik

(57) ABSTRACT

This invention relates to the novel protein, termed INSP163, herein identified as a secreted protein containing a jelly-roll fold, in particular, as a member of the TNF (tumor necrosis factor)-like family of cytokines, specifically as a C1q-like protein and to the use of this protein and nucleic acid sequence from the encoding gene in the diagnosis, prevention and treatment of disease.

18 Claims, 4 Drawing Sheets

Figure 1: Genome Threader output for INSP163 polypeptide sequence (SEQ ID NO: 30)

Genome Threader results - Energy Scores

| Num | PDB Code | Norm Align Score | Raw Align Score | %IDs | %Struct Aligned | %Query Seq Aligned | Pairwise Energy | Solvation Energy | Neural Net Score | %Confidence | From Pos for Query | To Pos for Query | From Pos for Target | To Pos for Target | Alignment Length |
|---|---|---|---|---|---|---|---|---|---|---|---|---|---|---|---|
| 1 | 1c3aA00 biopendium (align) | 67.63 | 96 | 19.8 | 75.0 | 37.7 | -155.89 | -4.34 | 0.983 | 96 | 187 | 300 | 31 | 129 | 116 |
| 2 | 1c28A00 biopendium (align) | 55.86 | 94 | 17.4 | 72.8 | 37.7 | -105.30 | -2.65 | 0.983 | 96 | 187 | 300 | 31 | 121 | 115 |
| 3 | 1c28c00 biopendium (align) | 51.74 | 79 | 20.2 | 70.6 | 37.7 | -9.01 | -3.13 | 0.977 | 92 | 187 | 300 | 28 | 99 | 114 |
| 4 | 1c28B00 biopendium (align) | 45.38 | 73 | 18.2 | 29.7 | 10.9 | -6.72 | -2.55 | 0.971 | 88 | 187 | 219 | 25 | 57 | 93 |
| 5 | 1tcyA00 biopendium (align) | 42.14 | 71 | 20.3 | 82.4 | 39.1 | -94.33 | 1.68 | 0.965 | 84 | 182 | 299 | 25 | 146 | 128 |
| 6 | 2mfA00 biopendium (align) | 39.14 | 68 | 17.8 | 81.8 | 39.1 | -69.55 | -2.50 | 0.961 | 81 | 182 | 299 | 26 | 146 | 129 |
| 7 | 1kcoA00 biopendium (align) | 34.25 | 63 | 19.0 | 77.8 | 38.7 | -43.14 | 3.51 | 0.937 | 69 | 183 | 299 | 30 | 141 | 121 |
| 8 | 1d2oA00 biopendium (align) | 32.56 | 61 | 16.8 | 75.4 | 39.4 | -12.75 | -4.44 | 0.943 | 72 | 183 | 301 | 34 | 134 | 119 |
| 9 | 1dq6A00 biopendium (align) | 31.11 | 60 | 15.3 | 80.5 | 39.7 | -7.91 | -3.18 | 0.933 | 68 | 182 | 301 | 30 | 149 | 131 |

Figure 2

```
  1  tgagccgcct cggggacggag ccatgcggcg ctgggcctgg gccgcggtcg tggtcctcct
                             m  r  r  w  a  w  a  a  v  v  v  l
     ─────────────────────────►
         INSP163-CP1

61  cgggccgcag ctcgtgctcc tcggggggcgt cggggcccgg cgggaggcac agaggacgca
      l  g  p  q  l  v  l  l  g  g  v  g  a  r  r  e  a  q  r  t 121  gcagcctggc cagcgcgcag atccccccaa cgccaccgcc agcgcgtcct cccgcgaggg
      q  q  p  g  q  r  a  d  p  p  n  a  t  a  s  a  s  s  r  e 181  gctgcccgag gcccccaagc catcccaggc ctcaggacct gagttctccg acgcccacat
      g  l  p  e  a  p  k  p  s  q  a  s  g  p  e  f  s  d  a  h 241  gacatggctg aactttgtcc ggcggccgga cgacggcgcc ttaaggaagc ggtgcggaag
      d  m  a  e  l  c  p  l  s  g  r  p  d  d  g  a  l  r  k  r  c  g
      m  t  w  l  n  f  v  r  r  p  d  d  g  a  l  r  k  r  c  g 301  cagggacaag aagccgcggg atctcttcgg tccccagga cctccaggtg cagaagtgac
      s  r  d  k  k  p  r  d  l  f  g  p  q  p  p  g  a  e  v 361  cgcggagact ctgcttcacg agtttcagga gctgctgaaa gaggccacgg agcgccggtt
      t  a  e  t  l  l  h  e  f  q  e  l  l  k  e  a  t  e  r  r 421  ctcagggctt ctggaccgc tgctgcccca gggggcgggc ctgcggctgg tgggcgaggc
      f  s  g  l  l  d  p  l  l  p  q  g  a  g  l  r  l  v  g  e 481  ctttcactgc cggctgcagg gtccccgccg ggtggacaag cggacgctgg tggagctgca
      a  f  h  c  r  l  q  g  p  r  v  d  k  r  t  l  v  e  l 541  tggtttccag gctcctgctg cccaaggtgc cttcctgcga ggctccggtc tgagcctggc
      h  g  f  q  a  p  a  a  q  g  a  f  l  r  g  s  g  l  s  l 601  ctcgggtcgg ttcacggccc ccgtgtccgg catcttccag ttctctgcca gtctgcacgt
      a  s  g  r  f  t  a  p  v  s  g  i  f  q  f  s  a  s  l  h 661  ggaccacagt gagctgcagg gcaaggcccg gctgcgggcc cgggacgtgg tgtgtgttct
      v  d  h  s  e  l  q  g  k  a  r  l  r  a  r  d  v  v  c  v 721  catctgtatt gagtccctgt gccagcgcca cacgtgcctg gaggccgtct caggcctgga
      l  i  c  i  e  s  l  c  q  r  h  t  c  l  e  a  v  s  g  l 781  gagcaacagc agggtcttca cgctacaggt gcagggctg ctgcagctgc aggctggaca
      e  s  n  s  r  v  f  t  l  q  v  q  g  l  l  q  l  q  a  g 841  gtacgcttct gtgtttgtgg acaatggctc cggggccgtc ctcaccatcc aggcgggctc
      q  y  a  s  v  f  v  d  n  g  s  g  a  v  l  t  i  q  a  g 901  cagcttctcc gggctgctcc tgggcacgt
      s  s  f  s  g  l  l  l  g  t
         ◄───────────────────────
               INSP163-CP2
```

Figure 3

A) INSP163-A

```
  1  PDDGALRKRC GSRDKKPRDL FGPPGPPGAE VTAETLLHEF QELLKEATER
 51  RFSGLLDPLL PQGAGLRLVG EAFHCRLQGP RRVDKRTLVE LHGFQAPAAQ
101  GAFLRGSGLS LASGRFTAPV SGIFQFSASL HVDHSELQGK ARLRARDVVC
151  VLICIESLCQ RHTCLEAVSG LESNSRVFTL QVQGLLQLQA GQYASVFVDN
201  GSGAVLTIQA GSSFSGLLLG T
```

B) INSP163-B

```
  1  KRCGSRDKKP RDLFGPPGPP GAEVTAETLL HEFQELLKEA TERRFSGLLD
 51  PLLPQGAGLR LVGEAFHCRL QGPRRVDKRT LVELHGFQAP AAQGAFLRGS
101  GLSLASGRFT APVSGIFQFS ASLHVDHSEL QGKARLRARD VVCVLICIES
151  LCQRHTCLEA VSGLESNSRV FTLQVQGLLQ LQAGQYASVF VDNGSGAVLT
201  IQAGSSFSGL LLGT
```

C) INSP163-C

```
  1  CGSRDKKPRD LFGPPGPPGA EVTAETLLHE FQELLKEATE RRFSGLLDPL
 51  LPQGAGLRLV GEAFHCRLQG PRRVDKRTLV ELHGFQAPAA QGAFLRGSGL
101  SLASGRFTAP VSGIFQFSAS LHVDHSELQG KARLRARDVV CVLICIESLC
151  QRHTCLEAVS GLESNSRVFT LQVQGLLQLQ AGQYASVFVD NGSGAVLTIQ
201  AGSSFSGLLL GT
```

D) INSP163-D

```
  1  FSGLLDPLLP QGAGLRLVGE AFHCRLQGPR RVDKRTLVEL HGFQAPAAQG
 51  AFLRGSGLSL ASGRFTAPVS GIFQFSASLH VDHSELQGKA RLRARDVVCV
101  LICIESLCQR HTCLEAVSGL ESNSRVFTLQ VQGLLQLQAG QYASVFVDNG
151  SGAVLTIQAG SSFSGLLLGT
```

E) INSP163-E

```
  1  VDKRTLVELH GFQAPAAQGA FLRGSGLSLA SGRFTAPVSG IFQFSASLHV
 51  DHSELQGKAR LRARDVVCVL ICIESLCQRH TCLEAVSGLE SNSRVFTLQV
101  QGLLQLQAGQ YASVFVDNGS GAVLTIQAGS SFSGLLLGT
```

F) INSP163-F

```
  1  TLVELHGFQA PAAQGAFLRG SGLSLASGRF TAPVSGIFQF SASLHVDHSE
 51  LQGKARLRAR DVVCVLICIE SLCQRHTCLE AVSGLESNSR VFTLQVQGLL
101  QLQAGQYASV FVDNGSGAVL TIQAGSSFSG LLLGT
```

ISOLATED INSP 163 PROTEIN

CROSS-REFERENCE TO RELATED APPLICATION

This application is the National Stage of International Application Number PCT/GB2004/004544, filed Oct. 27, 2004, which is hereby incorporated by reference herein in its entirety, including any figures, tables, nucleic acid sequences, amino acid sequences, or drawings.

This invention relates to a novel protein, termed INSP163, herein identified as a secreted protein containing a jelly-roll fold, in particular, as a member of the TNF (tumor necrosis factor)-like family of cytokines, specifically as a c1q-like protein and to the use of this protein and nucleic acid sequence from the encoding gene in the diagnosis, prevention and treatment of disease.

All publications, patents and patent applications cited herein are incorporated in full by reference.

BACKGROUND

The process of drug discovery is presently undergoing a fundamental revolution as the era of functional genomics comes of age. The term "functional genomics" applies to an approach utilising bioinformatics tools to ascribe function to protein sequences of interest. Such tools are becoming increasingly necessary as the speed of generation of sequence data is rapidly outpacing the ability of research laboratories to assign functions to these protein sequences.

As bioinformatics tools increase in potency and in accuracy, these tools are rapidly replacing the conventional techniques of biochemical characterisation. Indeed, the advanced bioinformatics tools used in identifying the present invention are now capable of outputting results in which a high degree of confidence can be placed.

Various institutions and commercial organisations are examining sequence data as they become available and significant discoveries are being made on an on-going basis. However, there remains a continuing need to identify and characterise further genes and the polypeptides that they encode, as targets for research and for drug discovery.

INTRODUCTION

Secreted Proteins

The ability for cells to make and secrete extracellular proteins is central to many biological processes. Enzymes, growth factors, extracellular matrix proteins and signalling molecules are all secreted by cells. This is through fusion of a secretory vesicle with the plasma membrane. In most cases, but not all, proteins are directed to the endoplasmic reticulum and into secretory vesicles by a signal peptide. Signal peptides are cis-acting sequences that affect the transport of polypeptide chains from the cytoplasm to a membrane bound compartment such as a secretory vesicle. Polypeptides that are targeted to the secretory vesicles are either secreted into the extracellular matrix or are retained in the plasma membrane. The polypeptides that are retained in the plasma membrane will have one or more transmembrane domains. Examples of secreted proteins that play a central role in the functioning of a cell are cytokines, hormones, extracellular matrix proteins (adhesion molecules), proteases, and growth and differentiation factors. Description of some of the properties of these proteins follows.

Cytokines

Cytokines are a family of growth factors secreted primarily from leukocytes, and are messenger proteins that act as potent regulators capable of effecting cellular processes at sub-nanomolar concentrations. Interleukins, neurotrophins, growth factors, interferons and chemokines all define cytokine families that work in conjunction with cellular receptors to regulate cell proliferation and differentiation. Their size allows cytokines to be quickly transported around the body and degraded when required. Their role in controlling a wide range of cellular functions, especially the immune response and cell growth, has been revealed by extensive research over the last twenty years (Boppana, S. B (1996) Indian. J. Pediatr. 63(4):447-52). Cytokines, as for other growth factors, are differentiated from classical hormones by the fact that they are produced by a number of different cell types rather than just one specific tissue or gland, and also affect a broad range of cells via interaction with specific high affinity receptors located on target cells.

All cytokine communication systems show both pleiotropy (one messenger producing multiple effects) and redundancy (each effect is produced by more than one messenger) (Tringali, G. et al., (2000) Therapie. 55(1):171-5; Tessarollo, L. (1998) Cytokine Growth Factor Rev. 9(2):125-137). An individual cytokine's effects on a cell can also be dependent on its concentration, the concentration of other cytokines, the temporal sequence of cytokines, and the internal state of the cell (cell cycle, presence of neighbouring cells, cancerous).

Although cytokines are typically small proteins (under 200 amino acids) they are often formed from larger precursors which are post-translationally spliced. This, in addition to MRNA alternative splicing pathways, give a wide spectrum of variants of each cytokine, each of which may differ substantially in biological effect. Membrane and extracellular matrix associated forms of many cytokines have also been isolated (Okada-Ban, M. et al., (2000) Int. J. Biochem. Cell Biol. 32(3):263-267; Atamas, S. P. (1997) Life Sci. 61(12): 1105-1112).

Cytokines can be grouped into families, though most are unrelated. Categorisation is usually based on secondary structure composition, as sequence similarity is often very low. The families are named after the archetypal member e.g. IFN-like, IL-2-like, IL-1-like, IL-6-like and TNF-like (Zlotnik, A. et al., (2000) Immunity. 12(2):121-127).

Studies have shown that cytokines are involved in many important reactions in multi-cellular organisms such as immune response regulation (Nishihira, J. (1998) Int. J. Mol. Med. 2(1):17-28), inflammation (Kim, P. K. et al., (2000) Surg. Clin. North. Am. 80(3):885-894), wound healing (Clark, R. A. (1991) J. Cell Biochem. 46(1):1-2), embryogenesis and development, and apoptosis (Flad, H. D. et al, (1999) Pathobiology. 67(5-6):291-293). Pathogenic organisms (both viral and bacterial) such as HIV and Kaposi's sarcoma-associated virus encode anti-cytokine factors as well as cytokine analogues, which allow them to interact with cytokine receptors and control the body's immune response (Sozzani, S. et al., (2000) Pharm. Acta. Helv. 74(2-3):305-312; Aoki, Y. et al., (2000) J. Hematother. Stem Cell Res. 9(2):137-145). Virally-encoded cytokines, virokines, have been shown to be required for pathogenicity of viruses due to their ability to mimic and subvert the host immune system.

It has been shown that the viral-encoded cytokine, macrophage inhibitory protein-II is able to mediate selective recruitment of Th2-type cells and evasion from a cytotoxic immune response (Weber K S et al., (2001), Eur J Immunol. 2001 31(8):2458-66). These data provide evidence for an immunomodulatory role of vMIP-II in directing inflammatory cell recruitment away from a Th1-type towards a Th2-type response and thereby facilitating evasion from cytotoxic reactions. Cytokines may therefore be used to modulate diseases in which over-stimulation of the Th1-type immune response is implicated, such as irritable bowel syndrome. In another study, Kawamoto S et al., (Int Immunol. 2001 13(5): 685-94) presented results that indicate that vIL-10 may well be superior to cellular IL-10 in the treatment of autoimmune diabetes. These results indicate that viral-encoded cytokines have potential therapeutic benefit beyond viral clearance alone.

Clinical use of cytokines has focused on their role as regulators of the immune system (Rodriguez, F. H. et al., (2000) Curr. Pharm. Des. 6(6):665-680) for instance in promoting a response against thyroid cancer (Schmutzler, C. et al., (2000) 143(1):15-24). Their control of cell growth and differentiation has also made cytokines anti-cancer targets (Lazar-Molnar, E. et al., (2000) Cytokine. 12(6):547-554; Gado, K. (2000) 24(4):195-209). Novel mutations in cytokines and cytokine receptors have been shown to confer disease resistance in some cases (van Deventer, S. J. et al., (2000) Intensive Care Med. 26 (Suppl 1):S98:S102). The creation of synthetic cytokines (muteins) in order to modulate activity and remove potential side effects has also been an important avenue of research (Shanafelt, A. B. et al., (1998) 95(16): 9454-9458).

Tumor necrosis factors (TNF) alpha and beta are examples of cytokines, which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, a number of members of the TNF ligand superfamily have been identified and several members of the TNF-receptor superfamily have been characterized.

Among the ligands there are included TNF-alpha, lymphotoxin-alpha (LT-alpha, also known as TNF-beta), LT-beta (found in complex heterotrimer LT-alpha2-beta), FasL, CD40L, CD27L, CD30L, 4-1BBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-1BB, OX40, low affinity p75 and NGF-receptor (Meager, A., Biologicals 22:291-295 (1994)).

Many members of the TNF-ligand superfamily are expressed by activated T-cells, implying that they are necessary for T-cell interactions with other cell types which underlie cell ontogeny and functions. (Meager, A., [supra]).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga. et al., Nature 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (Allen et al., Science 259:990 (1993)). Targeted mutations of the low affinity nerve growth factor receptor cause a disorder characterized by faulty sensory innovation of peripheral structures (Lee et al., Cell 69:737 (1992)).

C1q

C1q is a subunit of the C1 enzyme complex that activates the serum complement system. It is composed of 9 disulfide-linked dimers of the chains A, B and C, which share a common structure which consist of a N-terminal nonhelical region, a triple helical (collagenous) region and a C-terminal globular head which is called the c1q domain (Smith et al. 1994 Biochem. J. 301:249-256). Members of the c1q and TNF superfamily are involved in host defense, inflammation, apopotosis, autoimmunity, cell differentiation, organogenesis, hibernation and insulin-resistant obesity. Five strictly conserved residues have been identified in the c1q family (Kishore et al. Trends in Immunology 2004. 25(10):551-561). Each c1q domain exhibits a ten-stranded β-sandwich fold with a jelly-roll topology, consisting of two five-standed β-sheets (A', A, H, C, F) and (B', B, G, D, E), each made of antiparallel strands. Each of the five conserved residues within c1q family proteins belongs to the hydrophobic core of the c1q domain. The β-strands are strongly conserved in the different c1q domains (relative to orientation and size), in contrast with the loops connecting the β-strands which exhibit significant variability. There are two well conserved regions within the c1q domain: an aromatic motif is located within the first half of the domain, the other conserved region is located near the C-terminal extremity.

The C1q and TNF family proteins have similar gene structures: their c1q or THD domains are each encoded within one exon, whereas introns in both families are restricted to respective N-terminal collagen or stalk regions. The jelly-roll structure is remarkably similar to the capsid proteins of plant viruses and mammlian picoranviruses including foot-and-mouth and poliovirus.

C1q Containing Proteins include:
  Complement c1q subcomponent chains A, B and C. Efficient activation of C1 takes place on interaction of the globular heads of c1q with the Fc regions of IgG or IgM antibody present in immune complexes.
  Vertebrate short-chain collagen type VIII, the major component of the basement membrane of corneal endothelial cells. It is composed of a triple helical domain in between a short N-terminal and a larger C-terminal globule which contains the c1q domain.
  Vertebrate collagen type X, which has the same structure than collagen type VIII. It is a product of hyperthrophic chondrotocytes.
  Bluegill inner-ear specific structural protein. This short-chain collagen forms a microstructural matrix within the otolithic membrane.
  Chipmunk hibernation-associated plasma proteins HP-20, HP-25 and HP-27. These proteins disappear from blood specifically during hibernation. They contain a collagen-like domain near the N-terminus and a C-terminal c1q domain.
  Human precerebellin, which is located within postsynaptic structures of Purkinje cells, probably membrane-bound. Cerebellin is involved in synaptic activity.
  Rat precerebellin-like glycoprotein, a probable membrane protein. The c1q domain is located at the C-terminal extracellular extremity.
  Human endothelial cell multimerin (ECM), a carrier protein for platelet factor V/VA.
  Vertebrate 30 Kd adipocyte complement-related protein (ACRP30), also known as ApM1 or AdipoQ.

C1q represents a link between classical pathway-driven innate immunity and IgG- or IgM-mediated acquired immunity (the c1q and tumor necrosis factor superfamily has been reviewed by Kishore et al. 2004 Trends in Immunology.

25(10):551-561). IgG or IgM containing immune complexes bind to the c1q domain, including a conformational change in the collagen region. C1 q is involved in antimocrobial defense, maintenance of immune tolerance via clearance of apoptotic cells, phagocytosis of bacteria, neutralization of retroviruses, cell adhesion, and modulation of dentritic cells (DCs), B cells and fibroblasts through the action of a plethora of ligands such as envelope proteins of certain retroviruses, β-amyloid fibrils, lipopolysaccharides (LPS), porins from Gram-negative bacteria, phospholipids (PL), apoptotic cells and some acute phase reactants, including pentraxins (Kishore et al.). Nearly all ligands are recognized by the heterotrimeric c1q domain (~140 residues long).

The c1q domain interacts with other various proteins, including:

C-reactive protein (CRP) (major acute phase reactant). CRP binds chromatin and might have a major role in clearing chromosomal material from necrotic cells.

SAP, which results in complement activation.

PTX3, which mediates complement activation on apoptotic cells.

Decorin, which modulates the classical pathway activation in the tissue.

Gram negative bacteria proteins via lipid A, LPS and porins. OmpK36 (from *Klebsiella pneumoniae*) competes directly with IgG for binding to c1q.

Viral proteins (enveloped and non-enveloped) like envelope protein gp41 of HIV-1, gp21 of HTLV-I, p15e of MuLV). The c1q domain binding to viruses might result in virus neutralization. C1q-gp41 interaction leads to enhanced infection of complement-receptor-bearing cells, instead of viral lysis. Interaction between HTLV-I peptide and the c1q domain might affect the fusion process required for syncytium formation.

Pentraxins on apoptotic cells. C1q deficiency can cause SLE as a result of an impaired clearance of apoptotic cells. Surface blebs of apoptotic keratinocytes and peripheral blood mononuclear cells, which contain autoantigens are targeted in SLE. In c1q knockout mice, which have glomerulonephritis with immune deposits; a large number of apoptotic bodies are also present in diseased glomeruli. C1q might protect against autoimmunity by serving as an opsonin in the efficient recognition and physiological clearance of apoptotic cells, hence be required to maintain immune tolerance.

β-amayloid and familial dementia peptides (to the N-terminal region). Classical pathway activation leads to inflammation in neuritic plaques.

Cardiolipin and other anionic PLs, suggesting a possible role in the clearance of apoptotic and necrotic cells.

The C-terminal globular domain of the c1q subcomponents and collagen types VIII and X is important both for the correct folding and alignment of the triple helix and for protein-protein recognition events. For collagen type X it has been suggested that the domain is important for initiation and maintenance of the correct assembly of the protein (Kwan et al. 1991 J. Cell Biol. 114:597-604). In adiponectin, the c1q domain can ameliorate hyperglycemia and hyperinsulinemia much more potently than full-length adiponectin. Adiponectin was shown to suppress mature macrophage function by significantly inhibiting their phagocytic activity and their LPS-induced production of TNF-α, and thus might resolve inflammation. Adiponectin has also been shown to reverse insulin resistance associated with obesity by decreasing triglyceride content in the muscle and liver of obese mice. Decreased adiponectin has been implicated in the development of insulin resistance in mouse models of obesity and type 2 diabetes. A mild autosomal disorder associated with growth plate abnormalities, called 'Schmid metaphyseal chondrodysplasia' has been associated with missense mutations in the c1q domain of collagen X which disrupt the hydrophobic core and perturb trimer assembly. Specific mutations in the c1q domain of CTRP5 have been associated with late-onset retinal degeneration.

The collagen domain is found in collagens that are generally extracellular structural proteins involved in formation of connective tissue structure. The domain contains 20 copies of the G-X-Y repeat that forms a triple helix. The first position of the repeat is glycine, the second and third positions can be any residue but are frequently proline and hydroxyproline. Collagens are post translationally modified by proline hydroxylase to form the hydroxyproline residues. Defective hydroxylation is the cause of scurvy. Some members of the collagen superfamily are not involved in connective tissue structure but share the same triple helical structure. The antiproliferative (G1 mitotic arrest) and proapoptotic effect of c1q on human fibroblasts is mediated by the collagen region, via the calreticulin-CD91 complex. This interaction enhances p38 MAPK activation, NF-κB activity and production of prooinflammatory cytokines and chemokines in macrophages.

Alteration of the activity of c1q domain containing proteins thus provides a means to alter disease phenotype and as such, identification of novel proteins of this type is highly relevant as they may play a role in or be useful in the development of treatments for the diseases identified above, as well as other disease states.

THE INVENTION

The invention is based on the discovery that the INSP163 polypeptide is a member of the jelly-roll fold containing family of proteins, and particularly is a member of the TNF-like family of proteins and specifically is a c1q related protein.

In one embodiment of the first aspect of the invention, there is provided a polypeptide which:
(i) consists of the amino acid sequence as recited in SEQ ID NO:2 (alternative mature INSP163), SEQ ID NO: 34 (mature INSP163), SEQ ID NO: 4 (INSP163-A), SEQ ID NO: 6 (INSP163-B), SEQ ID NO: 8 (INSP163-C), SEQ ID NO: 10 (INSP163-D), SEQ ID NO: 12 (INSP163-E), and/or SEQ ID NO: 14 (INSP163-F);
(ii) is a fragment thereof which functions as a biological active polypeptide and/or has an antigenic determinant in common with the polypeptides of (i); or
(iii) is a functional equivalent of (i) or (ii).

Preferably a polypeptide according to this aspect of the invention is a c1q and collagen domain containing polypeptide.

The polypeptide having the sequence recited in SEQ ID NO: 2 is referred to hereafter as the "alternative mature INSP163 polypeptide". The polypeptide having the sequence recited in SEQ ID NO: 34 is referred to hereafter as the "mature INSP163 polypeptide". The polypeptide having the sequence recited in SEQ ID NO: 4 is referred to hereafter as the "INSP163-A polypeptide". The polypeptide having the sequence recited in SEQ ID NO: 6 is referred to hereafter as the "INSP163-B polypeptide". The polypeptide having the sequence recited in SEQ ID NO: 8 is referred to hereafter as the "INSP163-C polypeptide". The polypeptide having the sequence recited in SEQ ID NO: 10 is referred to hereafter as the "INSP163-D polypeptide". The polypeptide having the sequence recited in SEQ ID NO: 12 is referred to hereafter as the "INSP163-E polypeptide". The polypeptide having the sequence recited in SEQ ID NO: 14 is referred to hereafter as the "INSP163-F polypeptide".

Although the Applicant does not wish to be bound by this theory, it is postulated that the mature INSP163 polypeptide further comprises a signal peptide at the N-terminus that is 25 amino acids in length.

Furthermore, it is postulated that the alternative mature INSP163 polypeptide further comprises a signal peptide at the N-terminus that is 20 amino acids in length.

The full length mature INSP163 polypeptide and alternative mature INSP163 polypeptide sequence with their respective postulated signal sequence is recited in SEQ ID NO: 30.

The polypeptide having the sequence recited in SEQ ID NO: 30 is referred to hereafter as "the INSP163 polypeptide".

The polypeptides of the first aspect of the invention may further comprise a histidine tag. Preferably the histidine tag is found at the C-terminus of the polypeptide. Preferably the histidine tag comprises 1-10 histidine residues (e.g. 1, 2, 3, 4, 5, 6, 7, 8, 9 or 10 residues). More preferably, the histidine tag comprises 6 residues. Preferred polypeptides are therefore those comprising the sequence recited in SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 32 and/or SEQ ID NO: 36.

The polypeptide having the sequence recited in SEQ ID NO: 16 is referred to hereafter as the "histidine tag alternative mature INSP163 polypeptide". The polypeptide having the sequence recited in SEQ ID NO: 18 is referred to hereafter as the "histidine tag INSP163-A polypeptide". The polypeptide having the sequence recited in SEQ ID NO: 20 is referred to hereafter as the "histidine tag INSP163-B polypeptide". The polypeptide having the sequence recited in SEQ ID NO: 22 is referred to hereafter as the "histidine tag INSP163-C polypeptide". The polypeptide having the sequence recited in SEQ ID NO: 24 is referred to hereafter as the "histidine tag INSP163-D polypeptide". The polypeptide having the sequence recited in SEQ ID NO: 26 is referred to hereafter as the "histidine tag INSP163-E polypeptide". The polypeptide having the sequence recited in SEQ ID NO: 28 is referred to hereafter as the "histidine tag INSP163-F polypeptide". The polypeptide having the sequence recited in SEQ ID NO: 32 is referred to hereafter as the "histidine tag INSP163 polypeptide". The polypeptide having the sequence recited in SEQ ID NO: 36 is referred to hereafter as the "histidine tag mature INSP163 polypeptide".

The term "INSP163 polypeptides" as used herein includes the alternative mature INSP163 polypeptide, the mature INSP163 polypeptide, the INSP163-A polypeptide, the INSP163-B polypeptide, the INSP163-C polypeptide, the INSP163-D polypeptide, the INSP163-E polypeptide, the INSP163-F polypeptide, the INSP163 polypeptide, the histidine tag alternative mature INSP163 polypeptide, the histidine tag INSP163-A polypeptide, the histidine tag INSP163-B polypeptide, the histidine tag INSP163-C polypeptide, the histidine tag INSP163-D polypeptide, the histidine tag INSP163-E polypeptide, the histidine tag INSP163-F polypeptide, the histidine tag INSP163 polypeptide and the histidine tag mature INSP 163 polypeptide.

Preferably, a polypeptide according to any one of the above-described aspects of the invention functions as a member of the TNF-like family of proteins, more preferably as a c1q domain containing and/or a collagen domain containing protein.

By "functions as a member of the TNF-like family of proteins" we refer to polypeptides that comprise amino acid sequence or structural features that can be identified as conserved features within the polypeptides of the TNF-like family of proteins. Clinical use of such cytokines includes use as regulators of the immune system, and control of cell growth and differentiation and apoptosis.

By "functions as a c1q domain containing protein" we refer to polypeptides that comprise amino acid sequence or structural features that can be identified as conserved features within the polypeptides of the c1q domain containing family of proteins. In particular, we refer to the presence of cysteine residues in specific positions within the polypeptide that allow the formation of disulphide bonds. Like c1q itself, the INSP163 polypeptide may have an immune function; the polypeptide may also function as part of the extracellular matrix, the protein may also function in bone or cartilage formation and repair or have a role in energy metabolism.

By "functions as a collagen domain containing protein" we refer to polypeptides that comprise amino acid sequence or structural features that can be identified as conserved features within the polypeptides of the collagen domain containing family of proteins. In particular, we refer to the presence of cysteine residues in specific positions within the polypeptide that allow the formation of disulphide bonds. Furthermore, such polypeptides may have an antiproliferative and/or proapoptotic effect.

INSP163 has been shown to be structurally related (FIG. 4) with inner ear specific structural protein (SwissProt Acc. Code: COLE_LEPMA; Davis et al. 1995 Science 267:1031-1034), otolin-1 in fish otolith (SwissProt Acc. Code: OTO1_ONCKE; Murayama et al. Eur. J. Biochem 2002. 269:688-696), human alpha 1, alpha 2 and alpha 4 chains of different types (e.g. COL8A1, SwissProt Acc. Code: CA18_HUMAN and COL8A2, SwissProt Acc. Code: CA28_HUMAN; Muragaki et al. 1991 Eur. J. Biochem. 197: 615-622; Ota et al. Nat. Genet. 2004. 36:40-45), Collagen alpha 1(x) chain precursor (COL10A1, SwissProt Acc. Code: CA1A_HUMAN; Thomas et al. 1991 Biochem. J. 280:617-623), adiponectin (SwissProt Acc. Code: APM1_HUMAN), Complement c1q tumor necrosis factor-related protein 3 (CORS26; SwissProt Acc. Code: CQT3_HUMAN), Complement c1q tumor necrosis factor-related protein 5 (UNQ303; SwissProt Acc. Code: CQT5_HUMAN), tumor necrosis factor ligand superfamily member 13B (TNFSF-13B, also named BAFF, TALL-1, BLyS, THANK, zTNF-4; SwissProt Acc. Code: T13B_HUMAN), Ectodysplasin A (EDA, SwissProt Acc. Code: EDA_HUMAN), cerebellin 2 (CBLN2, SwissProt Acc. Code: CBN2_HUMAN) and Mus musculus 18-day embryo whole body cDNA (SwissProt Acc. Code: Q9CQI8).

Inner ear specific structural protein probably forms a microstructural matrix within the otolithic membrane in specialized secretory supporting cells at the outer perimeter of the saccular epithelium. Otolin-1 may be part of the internal framework of the otolith where it may provide nucleation sites to facilitate calcification (selectively expressed in the sacculus where it is localised to the otolith, the gelatinous layer of the otolithic membrane, and part of the transitional epithelium). COL8A1 and COL8A2 are major components of the Descemet's membrane (basement membrane) of corneal endothelial cells and form together homotrimers, or heterotrimers associations (tissue expression in lung and mammary tumor in mouse). Missense mutations in COL8A2 cause two forms of corneal endothelial dystrophy (Biswas et al. 2001 Hum. Mol. Genet. 10:2415-2423). Defects in COL8A2 are a cause of posterior polymorphous corneal dystrophy. PPCD is a slowly progressive hereditary disorder of the corneal endothelium that leads to a variable degree of visual impairment usually in adulthood. PPCD is usually inherited as an autosomal dominant trait. Defects in COL8A2 are also a cause of Fuchs endothelial corneal dystrophy (FECD). FECD is the commonest primary disorder of the corneal endothelium in developed countries. Symptoms of painful visual loss result from corneal decompensation. Signs may be present from the fourth decade of life onwards. Typically, focal wart-like guttata arising from Descemet's membrane develops in the central cornea; Descemet's membrane is thickened by abnormal collagenous deposition. FECD is usually sporadic but familial highly penetrant forms showing autosomal dominant inheritance are also recognised. In addition, elevated expression of type VIII collagen gene was found in the atherosclerotic plaque of the ApoE-deficient mouse, suggesting a role of COL8A chains in atherosclerosis (Yasuda et al. 2001 Ann N Y Acad Sci. 947:312-5). Overexpression of COL8A1 was detected in gastrointestinal stromal tumours (Koon et al. 2004 Gut. 53(2):235-40). Type X collagen (homotrimer subunit) is a product of hyperthrophic chondrotocytes and has been localized to presumptive mineralization zones of hyaline cartilage. Defects in COL10A1 are the cause of Schmid type metaphyseal chondrodysplasia (SMCD; Wallis et al. 1994 Am. J. Hum. Genet. 54:169-178). SMCD is a dominantly inherited disorder of the osseous skeleton. The cardinal features of the phenotype are mild short stature, coax vara and a waddling gait. Radiography usually shows sclerosis of the ribs, flaring of the metaphyses, and a wide irregular growth plate, especially of the knees. Defects in COL10A1 are also a cause of spondylometaphyseal dysplasia japanese type (SMD). SMD comprises a heterogeneous group of heritable skeletal dysplasias characterized by modifications of the vertebral bodies of the spine and metaphyses of the tubular bones. Adiponectin (ACDC gene) is an important negative regulator in hematopoiesis and immune systems. It may be involved in ending inflammatory responses through its inhibitory functions. It inhibits endothelial NF-kappa-B signaling through a cAMP-dependent pathway as well as TNF-alpha-induced expression of endothelial adhesion molecules. Adiponectin is involved in the control of fat metabolism and insulin sensitivity. It is synthesized exclusively by adipocytes and secreted into plasma. Defects in ACDC are the cause of adiponectin deficiency. The result is a very low concentration of plasma adiponectin. Decreased adiponectin plasma levels are associated with obesity insulin resistance, and diabetes type 2. CORS-26 might be involved in arthritis, bone or skeletal disease, osteosarcoma, chondroblastoma and giant cell tumor (Schaffler et al. 2003 Biochim Biophys Acta. 1628(1):64-70. 2003 Biochim Biophys Acta. 1630(2-3):123-9). Mutation in the c1q domain of Complement c1q tumor necrosis factor-related protein 5 could lead to late-onset retinal degeneration (L-ORD), age-related macular degeneration (AMD) and/or blindness (Hayward et al. 2003 Hum Mol Genet. 12(20):2657-67).

BAFF and the apoptosis ligand APRIL (also named TALL-2, TRDL-1 and TNFSF-13), including EDA and TWEAK, belong to a subgroup of the THD family. This subfamily share functional properties such as cell survival and differentiation, and structural features such as the presence of a furin convertase cleavage site in the stalk region of the protein and a disulfide bond link between the E and F strands within the molecules (Mackay and Ambrose, 2003 Cytokine Growth Factor Rev. 14(3-4):311-24). Soluble BAFF has been detected in serum (furin cleavage site RNKR↓) and APRIL is predominantly secreted as a soluble molecule (furin cleavage site RKRR↓). Cleavage sites have also been detected in INSP163. BAFF has been implicated in B cell survival, maturation and activation (involved in B cell immune responses), in T cell activation, and in maintenance of Ig-secreting cells, suggesting a critical role in promoting humoral responses and the maintenance of immune tolerance. BAFF has a role in:

1. Autoimmune diseases and inflammation. BAFF has been implicated in rheumatoid arthritis (RA), osteoarritis, Systemic lupus erythematosus (SLE), Sjögren syndrome, and multiple sclerosis (Thangarajh et al. 2004 J Neuroimmunol. 152(1-2):183-90).
2. Cancer. BAFF has been implicated in lymphomas (Non-Hodgkin's lymphoma (NHL), follicular lymphomas, Burkitt's lymphoma, mantle cell lymphoma (MCL), multiple myeloma (MM), leukemia (chronic lymphocytic leukemia/small lymphocity lymphoma (CLL/SLL)), diffuse large cell B cell lymphoma (DLCL), B cell hyperplasia.
3. Infections. BAFF has been implicated in HIV, *Streptococcus pneumoniae* and *Ascaris lumbricoides* infections.

It has been suggested that antagonism of BAFF may be a useful therapeutic approach for autoimmune disease, by e.g. the soluble forms of BAFF or antibodies targeted to BAFF. WO00/40716 discloses soluble secreted TNF receptor polypeptides inhibiting ztnf4 useful for the treament of autoimmune diseases (systemic lupus erythematosis, myasthenia gravis, multiple sclerosis, or rheumatoid arthritis), asthma, bronchitis or emphysema, renal failure (glomerulonephritis, vasculitis, nephritis or pyrlonephritis), renal neoplasms, multiple myelomas, lymphomas, light chain neuropathy or amyloidosis, graft rejection, graft verses host disease, diabetes mellitus or Crohn's Disease and inflammation (joint pain, swelling, anemia, or septic shock). The use of fusion proteins like transmembrane activator and calcium modulator and cyclophilin ligand interactor (TACI)-Ig or B cell maturation Ag (BCMA)-Ig alone or in combination with other fusion proteins (e.g. CTLA4-Ig), or Soluble TACI or BCMA for the treatment of autoimmune diseases has also been addressed (e.g. Ramanujam et al. 2004 J Immunol. 173(5):3524-34; US200301033986). WO04/039841 discloses trimeric binding units capable of binding a trimeric cytokine (e.g. BAFF) useful for the treatment of rheumatoid arthritis, psoriasis and Crohn's disease. WO04/024076 discloses compositions containing proteins (e.g. PRO738=BAFF) for the diagnosis and treatment of immune related diseases such as lupus erythematosis, rheumatoid arthritis, osteoarthritis, juvenile chronic arthritis, spondyloarthropathies, systemic sclerosis, idiopathic inflammatory myopathies, Sjogren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious, autoimmune chronic active hepatitis, primary biliary cirrhosis, granulomatous hepatitis, and sclerosing cholangitis, inflammatory bowel disease, gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host disease. WO03/016468 discloses human monoclonal antibodies that specifically bind to TNFSF13b for the treatment of systemic lupus erythematosus, rheumatoid arthritis, juvenile chronic arthritis, Lyme arthritis, Crohn's disease, ulcerative colitis, inflammatory bowel disease, asthma, allergic diseases, psoriasis, acute or chronic immune disease associated with organ transplantation, organ transplant rejection, graft-versus-host disease, sarcoidosis, infectious diseases, parasitic diseases, female infertility, autoimmune thrombocytopenia, autoimmune thyroid disease, Hashimoto's disease, Sjogren's syndrome, and cancer.

Ectodyslapin A plays a key role in ectodermal differentiation and has been involved in ectodermal dysplasia (e.g. X-linked hypohidrotic ectodermal dysplasia (HED). Chang and Chaudhary. 2004 Protein Expr Purif. 37(1):162-9).

The adrenal cortex and adrenocortical tumors produce and secrete peptides like cerebellin (Takahashi et al. 2002 Exp Clin Endocrinol Diabetes. 110(8):373-80). These peptides are involved in the regulation of steroid hormone secretion and the proliferation of adrenocotical cells as autocrine and/or paracrine factors. Takahashi et al. state that adrenocortical peptides are involved in the pathophysiology of inflammatory, ischemic or neoplastic diseases of the adrenal cortex. Cerebellin has been shown to be expressed in adrenal tumour, ganglioneuroblastoma, neuroblastoma, phaeochromocytomas and corstisol-producing adrenocortical adenomas (Satoh et al. 1997 J Endocrinol. 154(1):27-34). Cerebellin has also been involved in diseases linked to spinocerebellar degeneration, i.e. cerebellar diseases like olivopontocerebellar atrophy (OPCA) and Shy-Drager syndrome (Mizuno et al. No To Shinkei. 1995 47(11):1069-74); Mizuno et al. 1995 Brain Res. 686(1):115-8).

In a second aspect, the invention provides a purified nucleic acid molecule which encodes a polypeptide of the first aspect of the invention.

Preferably, the purified nucleic acid molecule comprises of the nucleic acid sequence as recited in SEQ ID NO: 1 (encoding the alternative mature INSP163 polypeptide), SEQ ID NO: 3 (encoding the INSP163-A polypeptide), SEQ ID NO: 5 (encoding the INSP163-B polypeptide), SEQ ID NO: 7 (encoding the INSP163-C polypeptide), SEQ ID NO: 9 (encoding the INSP163-D polypeptide), SEQ ID NO: 11 (encoding the INSP163-E polypeptide), SEQ ID NO: 13 (encoding the NSP163-F polypeptide), SEQ ID NO: 15 (encoding the histidine tag alternative mature NSP163 polypeptide), SEQ ID NO: 17 (encoding the histidine tag INSP163-A polypeptide), SEQ ID NO: 19 (encoding the histidine tag INSP163-B polypeptide), SEQ ID NO: 21 (encoding the histidine tag INSP163-C polypeptide), SEQ ID NO: 23 (encoding the histidine tag INSP163-D polypeptide), SEQ ID NO: 25 (encoding the histidine tag INSP163-E polypeptide), SEQ ID NO: 27 (encoding the histidine tag INSP163-F polypeptide), SEQ ID NO: 29 (encoding the INSP163 polypeptide), SEQ ID NO: 31 (encoding the histidine tag INSP163 polypeptide), SEQ ID NO: 33 (encoding the mature INSP163 polypeptide), SEQ ID NO: 35 (encoding the histidine tag mature INSP163 polypeptide).

The invention further provides that the purified nucleic acid molecule consists of the nucleic acid sequence recited in SEQ ID NO: 1 (encoding the alternative mature INSP163 polypeptide), SEQ ID NO: 3 (encoding the INSP163-A polypeptide), SEQ ID NO: 5 (encoding the INSP163-B polypeptide), SEQ ID NO: 7 (encoding the INSP163-C polypeptide), SEQ ID NO: 9 (encoding the INSP163-D polypeptide), SEQ ID NO: 11 (encoding the INSP163-E polypeptide), SEQ ID NO: 13 (encoding the INSP163-F polypeptide), SEQ ID NO: 15 (encoding the histidine tag alternative mature INSP163 polypeptide), SEQ ID NO: 17 (encoding the histidine tag INSP163-A polypeptide), SEQ ID NO: 19 (encoding the histidine tag INSP163-B polypeptide), SEQ ID NO: 21 (encoding the histidine tag INSP163-C polypeptide), SEQ ID NO: 23 (encoding the histidine tag INSP163-D polypeptide), SEQ ID NO: 25 (encoding the histidine tag INSP163-E polypeptide), SEQ ID NO: 27 (encoding the histidine tag INSP163-F polypeptide), SEQ ID NO: 29 (encoding the INSP163 polypeptide), SEQ ID NO: 31 (encoding the histidine tag INSP163 polypeptide), SEQ ID NO: 33 (encoding the mature INSP163 polypeptide), SEQ ID NO: 35 (encoding the histidine tag mature INSP163 polypeptide).

In a third aspect, the invention provides a purified nucleic acid molecule which hybridizes under high stringency conditions with a nucleic acid molecule of the second aspect of the invention.

In a fourth aspect, the invention provides a vector, such as an expression vector, that contains a nucleic acid molecule of the second or third aspect of the invention.

In a fifth aspect, the invention provides a host cell transformed with a vector of the fourth aspect of the invention.

In a sixth aspect, the invention provides a ligand which binds specifically to protein members of the TNF-like family of proteins, specifically c1q related proteins of the first aspect of the invention. Preferably, the ligand inhibits the function of a polypeptide of the first aspect of the invention which is a member of the TNF-like family of proteins, and specifically a c1q related protein. Ligands to a polypeptide according to the invention may come in various forms, including natural or modified substrates, enzymes, receptors, small organic molecules such as small natural or synthetic organic molecules of up to 2000 Da, preferably 800 Da or less, peptidomimetics, inorganic molecules, peptides, polypeptides, antibodies, structural or functional mimetics of the aforementioned.

In a seventh aspect, the invention provides a compound that is effective to alter the expression of a natural gene which encodes a polypeptide of the first aspect of the invention or to regulate the activity of a polypeptide of the first aspect of the invention.

A compound of the seventh aspect of the invention may either increase (agonise) or decrease (antagonise) the level of expression of the gene or the activity of the polypeptide.

Importantly, the identification of the function of the INSP163 polypeptides allows for the design of screening methods capable of identifying compounds that are effective in the treatment and/or diagnosis of disease. Ligands and compounds according to the sixth and seventh aspects of the invention may be identified using such methods. These methods are included as aspects of the present invention.

INSP163 and/or fragments thereof (e.g. fragments containing the c1q and/or collagen domain(s)) can be useful in the diagnosis and/or treatment of diseases for which other c1q domain containing proteins demonstrate therapeutic activity.

Therefore, in an eighth aspect, the invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in therapy or diagnosis of diseases in which members of the TNF-like family of proteins are implicated. Such diseases may include cell proliferative disorders, autoimmune/inflammatory disorders, genetic disorders, developmental disorders, nervous system disorders, metabolic disorders, infections and other pathological conditions; particularly immune disorders, such as autoimmune disease, rheumatoid arthritis, osteoarthritis, psoriasis, systemic lupus erythematosus, and multiple sclerosis, inflammatory disorders, such as allergy, rhinitis, conjunctivitis, glomerulonephritis, uveitis, Crohn's disease, ulcerative colitis, inflammatory bowel disease, pancreatitis, digestive system inflammation, sepsis, endotoxic shock, septic shock, cachexia, myalgia, ankylosing spondylitis, myasthenia gravis, post-viral fatigue syndrome, pulmonary disease, respiratory distress syndrome, asthma, chronic-obstructive pulmonary disease, airway inflammation, wound healing, endometriosis, dermatological disease, Behcet's disease, neoplastic disorders, such as melanoma, sarcoma, renal tumour, colon tumour, haematological disease, myeloproliferative disorder, diseases associated with the disregulation of apoptosis, Hodgkin's disease, osteoporosis, obesity, diabetes, gout, cardiovascular disorders, reperfusion injury, atherosclerosis, ischaemic heart disease, cardiac failure, stroke, liver disease, AIDS, AIDS related complex, neurological disorders, male infertility, ageing and infections, including plasmodium infection, bacterial infection and viral infection, hereditary diseases, including hyper IgM syndrome (HIM, CD40L), type I autoimmune lymphoproliferative syndrome (ALPS, Fas/FasL), TNF-R1-associated periodic fever syndrome (TRAPS, TNF-R1), hypohidrotic ectodermal dysplasia (HED, EDA/EDAR), familial expansile osteolysis (FEO, RANK) and other pathological conditions. Preferably the disease is selected from autoimmune diseases, autoimmune inner ear disease, Labyrinthitis, Ménière disease and Ménière syndrome, Perilymphatic or labyrinthine fistula, Tinnitus, neurodegenerative diseases, amyloidosis, Alzheimer's disease, Parkinson's disease, familial dementia, inflammation (joint pain, swelling, anemia, or septic shock), infectious diseases, parasitic diseases, microbial diseases, bacterial diseases, viral diseases (HIV, HTLV, MuLV, *Streptococcus pneumoniae* and *Ascaris lumbricoides* infections), glomerulonephritis, obesity, diabetes, diabetes mellitus, Schmid metaphyseal chondrodysplasia, corneal endothelial dystrophies, posterior polymorphous corneal dystrophy (PPCD), Fuchs endothelial corneal dystrophy (FECD), atherosclerosis, scurvy, cancer, gastrointestinal stromal tumours, osteosarcoma, chondroblastoma, giant cell tumor, spondylometaphyseal dysplasia japanese type (SMD), lymphomas (Non-Hodgkin's lymphoma (NHL), follicular lymphomas, Burkitt's lymphoma, mantle cell lymphoma (MCL), multiple myeloma (MM), leukemia (chronic lymphocytic leukemia/small lymphocity lymphoma (CLL/SLL)), diffuise large cell B cell lymphoma (DLCL), B cell hyperplasia, Osteogenesis Imperfecta, Ehlers-Danlos syndrome, susceptibility to dissection of cervical arteries, aortic aneurysm, otospondylomegaepiphyseal dysplasia, hearing loss (deafness), Weissenbacher-Zweymuller syndrome, bone or skeletal disease, late-onset retinal degeneration (L-ORD), age-related macular degeneration (AMD), blindness, athritis, rheumatoid arthritis (RA), osteoarthritis, lyme arthritis, juvenile chronic arthritis, spondyloarthropathies, Systemic lupus erythematosus (SLE), Sjögren syndrome, demyelinating diseases of the central and peripheral nervous systems such as multiple sclerosis, idiopathic demyelinating polyneuropathy or Guillain-Barre syndrome, and chronic inflammatory demyelinating polyneuropathy, myasthenia gravis, bronchitis, emphysema, renal failure (glomerulonephritis, vasculitis, nephritis or pyrlonephritis), renal neoplasms, renal cell carcinomas, renal tumour, light chain neuropathy or amyloidosis, acute or chronic immune disease associated with organ transplantation, organ transplant rejection, graft-versus-host disease, Crohn's Disease, systemic sclerosis, idiopathic inflammatory myopathies, systemic vasculitis, sarcoidosis, autoimmune hemolytic anemia, autoimmune thrombocytopenia, thyroiditis, immune-mediated renal disease, hepatobiliary diseases such as infectious, autoimmune chronic active hepatitis, primary biliary cirrhosis, granulomatous hepatitis, and sclerosing cholangitis, inflammatory bowel disease, gluten-sensitive enteropathy, and Whipple's disease, autoimmune or immune-mediated skin diseases including bullous skin diseases, erythema multiforme and contact dermatitis, psoriasis, atopic dermatitis, food hypersensitivity and urticaria, immunologic diseases of the lung such as eosinophilic pneumonias, idiopathic pulmonary fibrosis and hypersensitivity pneumonitis, ulcerative colitis, inflammatory bowel disease, allergic diseases such as asthma, allergic rhinitis, sarcoidosis, female infertility, autoimmune thrombocytopenia, autoimmune thyroid disease, Hashimoto's disease, Sjogren's syndrome, ectodermal dysplasia, X-linked hypohidrotic ectodermal dysplasia (HED), inflammatory, ischemic or neoplastic diseases of the adrenal cortex, adrenal tumour, ganglioneuroblastoma, neuroblastoma, phaeochromocytomas, corstisol-producing adrenocortical adenomas, diseases linked to spinocerebellar degeneration, cerebellar diseases, olivopontocerebellar atrophy (OPCA) and/or Shy-Drager syndrome.

These molecules may also be used in the manufacture of a medicament for the treatment of such diseases. These molecules may also be used in contraception or for the treatment of reproductive disorders including infertility.

In a ninth aspect, the invention provides a method of diagnosing a disease in a patient, comprising assessing the level of expression of a natural gene encoding a polypeptide of the first aspect of the invention or the activity of a polypeptide of the first aspect of the invention in tissue from said patient and comparing said level of expression or activity to a control level, wherein a level that is different to said control level is indicative of disease. Such a method will preferably be carried out in vitro. Similar methods may be used for monitoring the therapeutic treatment of disease in a patient, wherein altering the level of expression or activity of a polypeptide or nucleic acid molecule over the period of time towards a control level is indicative of regression of disease.

A preferred method for detecting polypeptides of the first aspect of the invention comprises the steps of: (a) contacting a ligand, such as an antibody, of the sixth aspect of the invention with a biological sample under conditions suitable for the formation of a ligand-polypeptide complex; and (b) detecting said complex.

A number of different such methods according to the ninth aspect of the invention exist, as the skilled reader will be aware, such as methods of nucleic acid hybridization with short probes, point mutation analysis, polymerase chain reaction (PCR) amplification and methods using antibodies to detect aberrant protein levels. Similar methods may be used on a short or long term basis to allow therapeutic treatment of a disease to be monitored in a patient. The invention also provides kits that are useful in these methods for diagnosing disease.

In a tenth aspect, the invention provides for the use of a polypeptide of the first aspect of the invention as a member of the TNF-like family of proteins, specifically as a c1q related protein. Suitable uses of the polypeptides of the invention as members of the TNF-like family of proteins and as c1q related proteins include use for fertility control and follicular development, use as part of a receptor/ligand pair and use as a diagnostic marker for a physiological or pathological condition selected from the list given above.

In an eleventh aspect, the invention provides a pharmaceutical composition comprising a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, in conjunction with a pharmaceutically-acceptable carrier.

In a twelfth aspect, the present invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in the manufacture of a medicament for the diagnosis or treatment of a disease.

In a thirteenth aspect, the invention provides a method of treating a disease in a patient comprising administering to the patient a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention.

For diseases in which the expression of a natural gene encoding a polypeptide of the first aspect of the invention, or in which the activity of a polypeptide of the first aspect of the invention, is lower in a diseased patient when compared to the level of expression or activity in a healthy patient, the polypeptide, nucleic acid molecule, ligand or compound administered to the patient should be an agonist. Conversely, for diseases in which the expression of the natural gene or activity of the polypeptide is higher in a diseased patient when compared to the level of expression or activity in a healthy patient, the polypeptide, nucleic acid molecule, ligand or compound administered to the patient should be an antagonist. Examples of such antagonists include antisense nucleic acid molecules, ribozymes and ligands, such as antibodies.

The INSP163 polypeptides are members of the TNF-like family of cytokines and more specifically are c1q related proteins and thus have roles in many disease states. Antagonists of the INSP163 polypeptides are of particular interest as they provide a way of modulating these disease states.

In a fourteenth aspect, the invention provides transgenic or knockout non-human animals that have been transformed to express higher, lower or absent levels of a polypeptide of the first aspect of the invention. Such transgenic animals are very useful models for the study of disease and may also be used in screening regimes for the identification of compounds that are effective in the treatment or diagnosis of such a disease.

A summary of standard techniques and procedures which may be employed in order to utilise the invention is given below. It will be understood that this invention is not limited to the particular methodology, protocols, cell lines, vectors and reagents described. It is also to be understood that the terminology used herein is for the purpose of describing particular embodiments only and it is not intended that this terminology should limit the scope of the present invention. The extent of the invention is limited only by the terms of the appended claims.

Standard abbreviations for nucleotides and amino acids are used in this specification.

The practice of the present invention will employ, unless otherwise indicated, conventional techniques of molecular biology, microbiology, recombinant DNA technology and immunology, which are within the skill of those working in the art.

Such techniques are explained fully in the literature. Examples of particularly suitable texts for consultation include the following: Sambrook Molecular Cloning; A Laboratory Manual, Second Edition (1989); DNA Cloning, Volumes I and II (D. N Glover ed. 1985); Oligonucleotide Synthesis (M. J. Gait ed. 1984); Nucleic Acid Hybridization (B. D. Hames & S. J. Higgins eds. 1984); Transcription and Translation (B. D. Harnes & S. J. Higgins eds. 1984); Animal Cell Culture (R. I. Freshney ed. 1986); Immobilized Cells and Enzymes (IRL Press, 1986); B. Perbal, A Practical Guide to Molecular Cloning (1984); the Methods in Enzymology series (Academic Press, Inc.), especially volumes 154 & 155; Gene Transfer Vectors for Mammalian Cells (J. H. Miller and M. P. Calos eds. 1987, Cold Spring Harbor Laboratory); Immunochemical Methods in Cell and Molecular Biology (Mayer and Walker, eds. 1987, Academic Press, London); Scopes, (1987) Protein Purification: Principles and Practice, Second Edition (Springer Verlag, N.Y.); and Handbook of Experimental Immunology, Volumes I-IV (D. M. Weir and C. C. Blackwell eds. 1986).

As used herein, the term "polypeptide" includes any peptide or protein comprising two or more amino acids joined to each other by peptide bonds or modified peptide bonds, i.e. peptide isosteres. This term refers both to short chains (peptides and oligopeptides) and to longer chains (proteins).

The polypeptide of the present invention may be in the form of a mature protein or may be a pre-, pro- or preproprotein that can be activated by cleavage of the pre-, pro- or prepro-portion to produce an active mature polypeptide. In such polypeptides, the pre-, pro- or prepro-sequence may be a leader or secretory sequence or may be a sequence that is employed for purification of the mature polypeptide sequence.

The polypeptide of the first aspect of the invention may form part of a fusion protein. For example, it is often advantageous to include one or more additional amino acid sequences which may contain secretory or leader sequences, pro-sequences, sequences which aid in purification, or sequences that confer higher protein stability, for example during recombinant production. Alternatively or additionally, the mature polypeptide may be fused with another compound, such as a compound to increase the half-life of the polypeptide (for example, polyethylene glycol).

In a further preferred embodiment, the polypeptide of the invention comprising a sequence having at least 85% of homology with INSP163 is a fusion protein.

These fusion proteins can be obtained by cloning a polynucleotide encoding a polypeptide comprising a sequence having at least 85% of homology INSP163 in frame to the coding sequences for a heterologous protein sequence.

The term "heterologous", when used herein, is intended to designate any polypeptide other than a human INSP163 polypeptide.

Example of heterologous sequences, that can be comprised in the soluble fusion proteins either at N- or at C-terminus, are the following: extracellular domains of membrane-bound protein, immunoglobulin constant regions (Fc region), multimerization domains, domains of extracellular proteins, signal sequences, export sequences, or sequences allowing purification by affinity chromatography.

Many of these heterologous sequences are commercially available in expression plasmids since these sequences are commonly included in the fusion proteins in order to provide additional properties without significantly impairing the specific biological activity of the protein fused to them (Terpe K, 2003 Appl Microbiol Biotechnol, 60:523-33). Examples of such additional properties are a longer lasting half-life in body fluids, the extracellular localization, or an easier purification procedure as allowed by the a stretch of Histidines forming the so-called "histidine tag" (Gentz et al., 1989 Proc Natl Acad Sci USA, 86:821-4) or by the "HA" tag, an epitope derived from the influenza hemagglutinin protein (Wilson et al., Cell, 37: 767-78, 1994). If needed, the heterologous sequence can be eliinated by a proteolytic cleavage, for example by inserting a proteolytic cleavage site between the protein and the heterologous sequence, and exposing the purified fusion protein to the appropriate protease. These features are of particular importance for the fusion proteins since they facilitate their production and use in the preparation of pharmaceutical compositions. For example, the protein used in the examples (INSP163) can be purified by means of a hexahistidine peptide fused at the C-terminus of INSP163. When the fusion protein comprises an immunoglobulin region, the fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met introduced between the sequence of the substances of the invention and the immunoglobulin sequence. The resulting fusion protein has improved properties, such as an extended residence time in body fluids (half-life), increased specific activity, increased expression level, or the purification of the fusion protein is facilitated.

In a preferred embodiment, the protein is fused to the constant region of an Ig molecule. Preferably, it is fused to heavy chain regions, like the CH2 and CH3 domains of human IgG1, for example. Other isoforms of Ig molecules are also suitable for the generation of fusion proteins according to the present invention, such as isoforms IgG2 or IgG4, or other Ig classes, like IgM or IgA, for example. Fusion proteins may be monomeric or multimeric, hetero- or homomultimeric.

In a further preferred embodiment, the functional derivative comprises at least one moiety attached to one or more functional groups, which occur as one or more side chains on the amino acid residues. Preferably, the moiety is a polyethylene (PEG) moiety. PEGylation may be carried out by known methods, such as the ones described in WO99/55377, for example.

Polypeptides may contain amino acids other than the 20 gene-encoded amino acids, modified either by natural processes, such as by post-translational processing or by chemical modification techniques which are well known in the art. Among the known modifications which may commonly be present in polypeptides of the present invention are glycosylation, lipid attachment, sulphation, gamma-carboxylation, for instance of glutamic acid residues, hydroxylation and ADP-ribosylation. Other potential modifications include acetylation, acylation, amidation, covalent attachment of flavin, covalent attachment of a haeme moiety, covalent attachment of a nucleotide or nucleotide derivative, covalent attachment of a lipid derivative, covalent attachment of phosphatidylinositol, cross-linking, cyclization, disulphide bond formation, demethylation, formation of covalent cross-links, formation of cysteine, formation of pyroglutamate, formylation, GPI anchor formation, iodination, methylation, myristoylation, oxidation, proteolytic processing, phosphorylation, prenylation, racemization, selenoylation, transfer-RNA mediated addition of amino acids to proteins such as arginylation, and ubiquitination.

Modifications can occur anywhere in a polypeptide, including the peptide backbone, the amino acid side-chains and the amino or carboxyl termini. In fact, blockage of the amino or carboxyl terminus in a polypeptide, or both, by a covalent modification is common in naturally-occurring and synthetic polypeptides and such modifications may be present in polypeptides of the present invention.

The modifications that occur in a polypeptide often will be a function of how the polypeptide is made. For polypeptides that are made recombinantly, the nature and extent of the modifications in large part will be determined by the post-translational modification capacity of the particular host cell and the modification signals that are present in the amino acid sequence of the polypeptide in question. For instance, glycosylation patterns vary between different types of host cell.

The polypeptides of the present invention can be prepared in any suitable manner. Such polypeptides include isolated naturally-occurring polypeptides (for example purified from cell culture), recombinantly-produced polypeptides (including fusion proteins), synthetically-produced polypeptides or polypeptides that are produced by a combination of these methods.

The functionally-equivalent polypeptides of the first aspect of the invention may be polypeptides that are homologous to the INSP163 polypeptides. Two polypeptides are said to be "homologous", as the term is used herin, if the sequence of one of the polypeptides has a high enough degree of identity or similarity to the sequence of the other polypeptide. "Identity" indicates that at any particular position in the aligned sequences, the amino acid residue is identical between the sequences. "Similarity" indicates that, at any particular position in the aligned sequences, the amino acid residue is of a similar type between the sequences. Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Percentage identity, as referred to herein, is as determined using BLAST version 2.1.3 using the default parameters specified by the NCBI (the National Center for Biotechnology Information; See Worldwide Website: ncbi.nlm.nih.gov/) [Blosum 62 matrix; gap open penalty=11 and gap extension penalty=1].

Homologous polypeptides therefore include natural biological variants (for example, allelic variants or geographical variations within the species from which the polypeptides are derived) and mutants (such as mutants containing amino acid substitutions, insertions or deletions) of the INSP163 polypeptides. Such mutants may include polypeptides in which one or more of the amino acid residues are substituted with a conserved or non-conserved amino acid residue (preferably a conserved amino acid residue) and such substituted amino acid residue may or may not be one encoded by the genetic code. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr. Particularly preferred are variants in which several, i.e. between 5 and 10, 1 and 5, 1 and 3, 1 and 2 or just 1 amino acids are substituted, deleted or added in any combination. Especially preferred are silent substitutions, additions and deletions, which do not alter the properties and activities of the protein. Also especially preferred in this regard are conservative substitutions. Such mutants also include polypeptides in which one or more of the amino acid residues includes a substituent group.

Typically, greater than 30% identity between two polypeptides is considered to be an indication of functional equivalence. Preferably, functionally equivalent polypeptides of the first aspect of the invention have a degree of sequence identity with the INSP163 polypeptide, or with active fragments thereof, of greater than 80%. More preferred polypeptides have degrees of identity of greater than 85%, 90%, 95%, 98% or 99%, respectively.

The functionally-equivalent polypeptides of the first aspect of the invention may also be polypeptides which have been identified using one or more techniques of structural alignment. For example, the Inpharmatica Genome Threader technology that forms one aspect of the search tools used to generate the Biopendium™ search database may be used (see PCT application WO 01/69507) to identify polypeptides of presently-unknown function which, while having low sequence identity as compared to the INSP163 polypeptides, are predicted to be members of the TNF-like family of proteins and c1q related proteins, by virtue of sharing significant structural homology with the INSP163 polypeptide sequence. By "significant structural homology" is meant that the Inpharmatica Genome Threader predicts two proteins to share structural homology with a certainty of 10% and above.

Polypeptides may be divided into fragments and similarly fragments of functional equivalents may exist. Such fragments are identified by being members of the same protein family as the full-length polypeptide, or having an antigenic determinant in common with the full-length polypeptides.

As used herein, the term "fragment" refers to a polypeptide having an amino acid sequence that is the same as part, but not all, of the amino acid sequence of a polypeptide or one of the functional equivalents of that polypeptide. The fragments should comprise at least n consecutive amino acids from the sequence and, depending on the particular sequence, n preferably is 7 or more (for example, 8, 10, 12, 14, 16, 18, 20 or more). Small fragments may form an antigenic determinant.

Fragments of full length polypeptides may consist of combinations of 1, 2, 3, 4, 5, 6, 7 or all 8 neighbouring exon sequences in the polypeptide sequences, respectively. For example, such combinations include exons 1 and 2, exons 2 and 3 or exons 1, 2 and 3, and so on. Such fragments are included in the present invention.

Such fragments may be "free-standing", i.e. not part of or fused to other amino acids or polypeptides, or they may be comprised within a larger polypeptide of which they form a part or region. When comprised within a larger polypeptide, the fragment of the invention most preferably forms a single continuous region. For instance, certain preferred embodiments relate to a fragment having a pre- and/or pro- polypeptide region fused to the amino terminus of the fragment and/or an additional region fused to the carboxyl terminus of the fragment. However, several fragments may be comprised within a single larger polypeptide.

The polypeptides of the present invention or their immunogenic fragments (comprising at least one antigenic determinant) can be used to generate ligands, such as polyclonal or monoclonal antibodies, that are immunospecific for the polypeptides. Such antibodies may be employed to isolate or to identify clones expressing the polypeptides of the invention or to purify the polypeptides by affinity chromatography. The antibodies may also be employed as diagnostic or therapeutic aids, amongst other applications, as will be apparent to the skilled reader.

The term "immunospecific" means that the antibodies have substantially greater affinity for the polypeptides of the invention than their affinity for other related polypeptides in the prior art. As used herein, the term "antibody" refers to intact molecules as well as to fragments thereof, such as Fab, F(ab')2 and Fv, which are capable of binding to the antigenic determinant in question. Such antibodies thus bind to the polypeptides of the first aspect of the invention.

By "substantially greater affinity" we mean that there is a measurable increase in the affinity for a polypeptide of the invention as compared with the affinity for known secreted proteins.

Preferably, the affinity is at least 1.5-fold, 2-fold, 5-fold 10-fold, 100-fold, $10^3$-fold, $10^4$-fold, $10^5$-fold, $10^6$-fold or greater for a polypeptide of the invention than for known secreted proteins such as members of the TNF-like family of proteins.

If polyclonal antibodies are desired, a selected mammal, such as a mouse, rabbit, goat or horse, may be immunised with a polypeptide of the first aspect of the invention. The polypeptide used to immunise the animal can be derived by recombinant DNA technology or can be synthesized chemically. If desired, the polypeptide can be conjugated to a carrier protein. Commonly used carriers to which the polypeptides may be chemically coupled include bovine serum albumin, thyroglobulin and keyhole limpet haemocyanin. The coupled polypeptide is then used to immunise the animal. Serum from the immunised animal is collected and treated according to known procedures, for example by immunoaffinity chromatography.

Monoclonal antibodies to the polypeptides of the first aspect of the invention can also be readily produced by one skilled in the art. The general methodology for making monoclonal antibodies using hybridoma technology is well known (see, for example, Kohler, G. and Milstein, C., Nature 256: 495-497 (1975); Kozbor et al, Immunology Today 4: 72 (1983); Cole et al., 77-96 in Monoclonal Antibodies and Cancer Therapy, Alan R. Liss, Inc. (1985).

Panels of monoclonal antibodies produced against the polypeptides of the first aspect of the invention can be screened for various properties, i.e., for isotype, epitope, affinity, etc. Monoclonal antibodies are particularly useful in purification of the individual polypeptides against which they are directed. Alternatively, genes encoding the monoclonal antibodies of interest may be isolated from hybridomas, for instance by PCR techniques known in the art, and cloned and expressed in appropriate vectors.

Chimeric antibodies, in which non-human variable regions are joined or fused to human constant regions (see, for example, Liu et al., Proc. Natl. Acad. Sci. USA, 84, 3439 (1987)), may also be of use.

The antibody may be modified to make it less immunogenic in an individual, for example by humanisation (see Jones et aL, Nature, 321, 522 (1986); Verhoeyen et al., Science, 239, 1534 (1988); Kabat et al., J. Immunol., 147, 1709 (1991); Queen et aL, Proc. Natl. Acad. Sci. USA, 86, 10029 (1989); Gorman et al., Proc. Natl Acad. Sci. USA, 88, 34181 (1991); and Hodgson et al., Bio/Technology, 9, 421 (1991)). The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody.

In a further alternative, the antibody may be a "bispecific" antibody, that is, an antibody having two different antigen binding domains, each domain being directed against a different epitope.

Phage display technology may be utilised to select genes which encode antibodies with binding activities towards the polypeptides of the invention either from repertoires of PCR amplified V-genes of lymphocytes from humans screened for possessing the relevant antibodies, or from naive libraries (McCafferty, J. et al., (1990), Nature 348, 552-554; Marks, J. et aL, (1992) Biotechnology 10, 779-783). The affinity of these antibodies can also be improved by chain shuffling (Clackson, T. et al., (1991) Nature 352, 624-628).

Antibodies generated by the above techniques, whether polyclonal or monoclonal, have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme.

Preferred nucleic acid molecules of the second and third aspects of the invention are those which encode a polypeptide sequence as recited in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 and/or SEQ ID NO: 36 and functionally equivalent polypeptides. These nucleic acid molecules may be used in the methods and applications described herein. The nucleic acid molecules of the invention preferably comprise at least n consecutive nucleotides from the sequences disclosed herein where, depending on the particular sequence, n is 10 or more (for example, 12, 14, 15, 18, 20, 25, 30, 35, 40 or more).

The nucleic acid molecules of the invention also include sequences that are complementary to nucleic acid molecules described above (for example, for antisense or probing purposes).

Nucleic acid molecules of the present invention may be in the form of RNA, such as MRNA, or in the form of DNA, including, for instance CDNA, synthetic DNA or genomic DNA. Such nucleic acid molecules may be obtained by cloning, by chemical synthetic techniques or by a combination thereof. The nucleic acid molecules can be prepared, for example, by chemical synthesis using techniques such as solid phase phosphoramidite chemical synthesis, from genomic or cDNA libraries or by separation from an organism. RNA molecules may generally be generated by the in vitro or in vivo transcription of DNA sequences.

The nucleic acid molecules may be double-stranded or single-stranded. Single-stranded DNA may be the coding strand, also known as the sense strand, or it may be the non-coding strand, also referred to as the anti-sense strand.

The term "nucleic acid molecule" also includes analogues of DNA and RNA, such as those containing modified backbones, and peptide nucleic acids (PNA). The term "PNA", as used herein, refers to an antisense molecule or an anti-gene agent which comprises an oligonucleotide of at least five nucleotides in length linked to a peptide backbone of amino acid residues, which preferably ends in lysine. The terminal lysine confers solubility to the composition. PNAs may be pegylated to extend their lifespan in a cell, where they preferentially bind complementary single stranded DNA and RNA and stop transcript elongation (Nielsen, P. E. et al. (1993) Anticancer Drug Des. 8:53-63).

A nucleic acid molecule which encodes a polypeptide of this invention may be identical to the coding sequence of one or more of the nucleic acid molecules disclosed herein.

These molecules also may have a different sequence which, as a result of the degeneracy of the genetic code, encodes a polypeptide SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36. Such nucleic acid molecules may include, but are not limited to, the coding sequence for the mature polypeptide by itself, the coding sequence for the mature polypeptide and additional coding sequences, such as those encoding a leader or secretory sequence, such as a pro-, pre- or prepro-polypeptide sequence; the coding sequence of the mature polypeptide, with or without the aforementioned additional coding sequences, together with further additional, non-coding sequences, including non-coding 5' and 3' sequences, such as the transcribed, non-translated sequences that play a role in transcription (including termination signals), ribosome binding and MRNA stability. The nucleic acid molecules may also include additional sequences which encode additional amino acids, such as those which provide additional functionalities.

The nucleic acid molecules of the second and third aspects of the invention may also encode the functional equivalents of the polypeptides of the first aspect of the invention. Such a nucleic acid molecule may be a naturally-occurring variant such as a naturally-occurring allelic variant, or the molecule may be a variant that is not known to occur naturally. Such non-naturally occurring variants of the nucleic acid molecule may be made by mutagenesis techniques, including those applied to nucleic acid molecules, cells or organisms.

Among variants in this regard are variants that differ from the aforementioned nucleic acid molecules by nucleotide substitutions, deletions or insertions. The substitutions, deletions or insertions may involve one or more nucleotides. The variants may be altered in coding or non-coding regions or both. Alterations in the coding regions may produce conservative or non-conservative amino acid substitutions, deletions or insertions.

The nucleic acid molecules of the invention can also be engineered, using methods generally known in the art, for a variety of reasons, including modifying the cloning, processing, and/or expression of the gene product (the polypeptide). DNA shuffling by random fragmentation and PCR reassembly of gene fragments and synthetic oligonucleotides are included as techniques which may be used to engineer the nucleotide sequences. Site-directed mutagenesis may be used to insert new restriction sites, alter glycosylation patterns, change codon preference, produce splice variants, introduce mutations and so forth.

Nucleic acid molecules which encode a polypeptide of the first aspect of the invention may be ligated to a heterologous sequence so that the combined nucleic acid molecule encodes a fusion protein. Such combined nucleic acid molecules are included within the second or third aspects of the invention. For example, to screen peptide libraries for inhibitors of the activity of the polypeptide, it may be useful to express, using such a combined nucleic acid molecule, a fusion protein that can be recognised by a commercially-available antibody. A fusion protein may also be engineered to contain a cleavage site located between the sequence of the polypeptide of the invention and the sequence of a heterologous protein so that the polypeptide may be cleaved and purified away from the heterologous protein.

The nucleic acid molecules of the invention also include antisense molecules that are partially complementary to nucleic acid molecules encoding polypeptides of the present invention and that therefore hybridize to the encoding nucleic acid molecules (hybridization). Such antisense molecules, such as oligonucleotides, can be designed to recognise, specifically bind to and prevent transcription of a target nucleic acid encoding a polypeptide of the invention, as will be known by those of ordinary skill in the art (see, for example, Cohen, J. S., Trends in Pharm. Sci., 10, 435 (1989), Okano, J. Neurochem. 56, 560 (1991); O'Connor, J. Neurochem 56, 560 (1991); Lee et al., Nucleic Acids Res 6, 3073 (1979); Cooney et al., Science 241, 456 (1988); Dervan et al., Science 251, 1360 (1991).

The term "hybridization" as used here refers to the association of two nucleic acid molecules with one another by hydrogen bonding. Typically, one molecule will be fixed to a solid support and the other will be free in solution. Then, the two molecules may he placed in contact with one another under conditions that favour hydrogen bonding. Factors that affect this bonding include: the type and volume of solvent; reaction temperature; time of hybridization; agitation; agents to block the non-specific attachment of the liquid phase molecule to the solid support (Denhardt's reagent or BLOTTO); the concentration of the molecules; use of compounds to increase the rate of association of molecules (dextran sulphate or polyethylene glycol); and the stringency of the washing conditions following hybridization (see Sambrook et al. [supra]).

The inhibition of hybridization of a completely complementary molecule to a target molecule may be examined using a hybridization assay, as known in the art (see, for example, Sambrook et al. [supra]). A substantially homologous molecule will then compete for and inhibit the binding of a completely homologous molecule to the target molecule under various conditions of stringency, as taught in Wahl, G. M. and S. L. Berger (1987; Methods Enzymol. 152:399-407) and Kimmel, A. R. (1987; Methods Enzymol. 152:507-511).

"Stringency" refers to conditions in a hybridization reaction that favour the association of very similar molecules over association of molecules that differ. High stringency hybridisation conditions are defined as overnight incubation at 42° C. in a solution comprising 50% formamide, 5×SSC (150 mM NaCl, 15 nM trisodium citrate), 50 mM sodium phosphate (pH7.6), 5× Denhardts solution, 10% dextran sulphate, and 20 microgram/ml denatured, sheared salmon sperm DNA, followed by washing the filters in 0.1×SSC at approximately 65° C. Low stringency conditions involve the hybridisation reaction being carried out at 35° C. (see Sambrook et al. [supra]). Preferably, the conditions used for hybridization are those of high stringency.

Preferred embodiments of this aspect of the invention are nucleic acid molecules that are at least 70% identical over their entire length to a nucleic acid molecule encoding the INSP163 polypeptides and nucleic acid molecules that are substantially complementary to such nucleic acid molecules. Preferably, a nucleic acid molecule according to this aspect of the invention comprises a region that is at least 80% identical over its entire length to such coding sequences, or is a nucleic acid molecule that is complementary thereto. In this regard, nucleic acid molecules at least 90%, preferably at least 95%, more preferably at least 98%, 99% or more identical over their entire length to the same are particularly preferred. Preferred embodiments in this respect are nucleic acid molecules that encode polypeptides which retain substantially the same biological function or activity as the INSP163 polypeptides.

The invention also provides a process for detecting a nucleic acid molecule of the invention, comprising the steps of: (a) contacting a nucleic probe according to the invention with a biological sample under hybridizing conditions to form duplexes; and (b) detecting any such duplexes that are formed.

As discussed additionally below in connection with assays that may be utilised according to the invention, a nucleic acid molecule as described above may be used as a hybridization probe for RNA, cDNA or genomic DNA, in order to isolate full-length cDNAs and genomic clones encoding the INSP163 polypeptides and to isolate cDNA and genomic clones of homologous or orthologous genes that have a high sequence similarity to the gene encoding this polypeptide.

In this regard, the following techniques, among others known in the art, may be utilised and are discussed below for purposes of illustration. Methods for DNA sequencing and analysis are well known and are generally available in the art and may, indeed, be used to practice many of the embodiments of the invention discussed herein. Such methods may employ such enzymes as the Klenow fragment of DNA polymerase I, Sequenase (US Biochemical Corp, Cleveland, Ohio), Taq polymerase (Perkin Elmer), thermostable T7 polymerase (Amersham, Chicago, Ill.), or combinations of polymerases and proof-reading exonucleases such as those found in the ELONGASE Amplification System marketed by Gibco/BRL (Gaithersburg, Md.). Preferably, the sequencing process may be automated using machines such as the Hamilton Micro Lab 2200 (Hamilton, Reno, Nev.), the Peltier Thermal Cycler (PTC200; MJ Research, Watertown, Mass.) and the ABI Catalyst and 373 and 377 DNA Sequencers (Perkin Elmer).

One method for isolating a nucleic acid molecule encoding a polypeptide with an equivalent function to that of the INSP163 polypeptide is to probe a genomic or cDNA library with a natural or artificially-designed probe using standard procedures that are recognised in the art (see, for example, "Current Protocols in Molecular Biology", Ausubel et al. (eds). Greene Publishing Association and John Wiley Interscience, New York, 1989, 1992). Probes comprising at least 15, preferably at least 30, and more preferably at least 50, contiguous bases that correspond to, or are complementary to, nucleic acid sequences from the appropriate encoding gene (SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33 and SEQ ID NO: 35), are particularly useful probes. Such probes may be labelled with an analytically-detectable reagent to facilitate their identification. Useful reagents include, but are not limited to, radioisotopes, fluorescent dyes and enzymes that are capable of catalysing the formation of a detectable product. Using these probes, the ordinarily skilled artisan will be capable of isolating complementary copies of genomic DNA, cDNA or RNA polynucleotides encoding proteins of interest from human, mammalian or other animal sources and screening such sources for related sequences, for example, for additional members of the family, type and/or subtype.

In many cases, isolated cDNA sequences will be incomplete, in that the region encoding the polypeptide will be cut short, normally at the 5' end. Several methods are available to obtain full length cDNAs, or to extend short cDNAs. Such sequences may be extended utilising a partial nucleotide sequence and employing various methods known in the art to detect upstream sequences such as promoters and regulatory elements. For example, one method which may be employed is based on the method of Rapid Amplification of cDNA Ends (RACE; see, for example, Frohman et al., PNAS USA 85, 8998-9002, 1988). Recent modifications of this technique, exemplified by the Marathon™ technology (Clontech Laboratories Inc.), for example, have significantly simplified the search for longer cDNAs. A slightly different technique, termed "restriction-site" PCR, uses universal primers to retrieve unknown nucleic acid sequence adjacent a known locus (Sarkar, G. (1993) PCR Methods Applic. 2:318-322). Inverse PCR may also be used to amplify or to extend sequences using divergent primers based on a known region (Triglia, T. et al. (1988) Nucleic Acids Res. 16:8186). Another method which may be used is capture PCR which involves PCR amplification of DNA fragments adjacent a known sequence in human and yeast artificial chromosome DNA (Lagerstrom, M. et al. (1991) PCR Methods Applic., 1, 111-119). Another method which may be used to retrieve unknown sequences is that of Parker, J. D. et al. (1991); Nucleic Acids Res. 19:3055-3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

In one embodiment of the invention, the nucleic acid molecules of the present invention may be used for chromosome localisation. In this technique, a nucleic acid molecule is specifically targeted to, and can hybridize with, a particular location on an individual human chromosome. The mapping of relevant sequences to chromosomes according to the present invention is an important step in the confirmatory correlation of those sequences with the gene-associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopldns University Welch Medical Library). The relationships between genes and diseases that have been mapped to the same chromosomal region are then identified through linkage analysis (coinheritance of physically adjacent genes). This provides valuable information to investigators searching for disease genes using positional cloning or other gene discovery techniques. Once the disease or syndrome has been crudely localised by genetic linkage to a particular genomic region, any sequences mapping to that area may represent associated or regulatory genes for further investigation. The nucleic acid molecule may also be used to detect differences in the chromosomal location due to translocation, inversion, etc. among normal, carrier, or affected individuals.

The nucleic acid molecules of the present invention are also valuable for tissue localisation. Such techniques allow the determination of expression patterns of the polypeptide in tissues by detection of the mRNAs that encode them. These techniques include in situ hybridization techniques and nucleotide amplification techniques, such as PCR. Results from these studies provide an indication of the normal functions of the polypeptide in the organism. In addition, comparative studies of the normal expression pattern of mRNAs with that of mRNAs encoded by a mutant gene provide valuable insights into the role of mutant polypeptides in disease. Such inappropriate expression may be of a temporal, spatial or quantitative nature.

Gene silencing approaches may also be undertaken to down-regulate endogenous expression of a gene encoding a polypeptide of the invention. RNA interference (RNAi) (Elbashir, SM et al., Nature 2001, 411, 494-498) is one method of sequence specific post-transcriptional gene silencing that may be employed. Short dsRNA oligonucleotides are synthesised in vitro and introduced into a cell. The sequence specific binding of these dsRNA oligonucleotides triggers the degradation of target MRNA, reducing or ablating target protein expression.

Efficacy of the gene silencing approaches assessed above may be assessed through the measurement of polypeptide expression (for example, by Western blotting), and at the RNA level using TaqMan-based methodologies.

The vectors of the present invention comprise nucleic acid molecules of the invention and may be cloning or expression vectors. The host cells of the invention, which may be transformed, transfected or transduced with the vectors of the invention may be prokaryotic or eukaryotic.

The polypeptides of the invention may be prepared in recombinant form by expression of their encoding nucleic acid molecules in vectors contained within a host cell. Such expression methods are well known to those of skill in the art and many are described in detail by Sambrook et al. (supra) and Fernandez & Hoeffler (1998, eds. "Gene expression systems. Using nature for the art of expression". Academic Press, San Diego, London, Boston, New York, Sydney, Tokyo, Toronto).

Generally, any system or vector that is suitable to maintain, propagate or express nucleic acid molecules to produce a polypeptide in the required host may be used. The appropriate nucleotide sequence may be inserted into an expression system by any of a variety of well-known and routine techniques, such as, for example, those described in Sambrook et al., (supra). Generally, the encoding gene can be placed under the control of a control element such as a promoter, ribosome binding site (for bacterial expression) and, optionally, an operator, so that the DNA sequence encoding the desired polypeptide is transcribed into RNA in the transformed host cell.

Examples of suitable expression systems include, for example, chromosomal, episomal and virus-derived systems, including, for example, vectors derived from: bacterial plasmids, bacteriophage, transposons, yeast episomes, insertion elements, yeast chromosomal elements, viruses such as baculoviruses, papova viruses such as SV40, vaccinia viruses, adenoviruses, fowl pox viruses, pseudorabies viruses and retroviruses, or combination thereof, such as those derived from plasmid and bacteriophage genetic elements, including cosmids and phagemids. Human artificial chromosomes (HACs) may also be employed to deliver larger fragments of DNA than can be contained and expressed in a plasmid. The vectors pCR4-TOPO-INSP163, pENTR_INSP163-6HIS, pEAK12d_INSP163-6HIS, pDEST12.2_INSP163-6HIS are preferred examples of suitable vectors for use in accordance with the aspects of this invention relating to INSP163.

Particularly suitable expression systems include microorganisms such as bacteria transformed with recombinant bacteriophage, plasmid or cosmid DNA expression vectors; yeast transformed with yeast expression vectors; insect cell systems infected with virus expression vectors (for example, baculovirus); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems. Cell-free translation systems can also be employed to produce the polypeptides of the invention.

Introduction of nucleic acid molecules encoding a polypeptide of the present invention into host cells can be effected by methods described in many standard laboratory manuals, such as Davis et al, Basic Methods in Molecular Biology (1986) and Sambrook et al., (supra). Particularly suitable methods include calcium phosphate transfection, DEAE-dextran mediated transfection, transfection, microinjection, cationic lipid-mediated transfection, electroporation, transduction, scrape loading, ballistic introduction or infection (see Sambrook et al., 1989 [supra]; Ausubel et al., 1991 [supra]; Spector, Goldman & Leinwald, 1998). In eukaryotic cells, expression systems may either be transient (for example, episomal) or permanent (chromosomal integration) according to the needs of the system.

The encoding nucleic acid molecule may or may not include a sequence encoding a control sequence, such as a signal peptide or leader sequence, as desired, for example, for secretion of the translated polypeptide into the lumen of the endoplasmic reticulum, into the periplasmic space or into the extracellular environment. These signals may be endogenous to the polypeptide or they may be heterologous signals. Leader sequences can be removed by the bacterial host in post-translational processing.

In addition to control sequences, it may be desirable to add regulatory sequences that allow for regulation of the expression of the polypeptide relative to the growth of the host cell Examples of regulatory sequences are those which cause the expression of a gene to be increased or decreased in response to a chemical or physical stimulus, including the presence of a regulatory compound or to various temperature or metabolic conditions. Regulatory sequences are those non-translated regions of the vector, such as enhancers, promoters and 5' and 3' untranslated regions. These interact with host cellular proteins to carry out transcription and translation. Such regulatory sequences may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the Bluescript phagemid (Stratagene, LaJolla, Calif.) or pSportI™ plasmid (Gibco BRL) and the like may be used. The baculovirus polyhedrin promoter may be used in insect cells. Promoters or enhancers derived from the genomes of plant cells (for example, heat shock, RUBISCO and storage protein genes) or from plant viruses (for example, viral promoters or leader sequences) may be cloned into the vector. In mammalian cell systems, promoters from mammalian genes or from mammalian viruses are preferable. If it is necessary to generate a cell line that contains multiple copies of the sequence, vectors based on SV40 or EBV may be used with an appropriate selectable marker.

An expression vector is constructed so that the particular nucleic acid coding sequence is located in the vector with the appropriate regulatory sequences, the positioning and orientation of the coding sequence with respect to the regulatory sequences being such that the coding sequence is transcribed under the "control" of the regulatory sequences, i.e., RNA polymerase which binds to the DNA molecule at the control sequences transcribes the coding sequence. In some cases it may be necessary to modify the sequence so that it may be attached to the control sequences with the appropriate orientation; i.e., to maintain the reading frame.

The control sequences and other regulatory sequences may be ligated to the nucleic acid coding sequence prior to insertion into a vector. Alternatively, the coding sequence can be cloned directly into an expression vector that already contains the control sequences and an appropriate restriction site.

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines.

In the baculovirus system, the materials for baculovirus/ insect cell expression systems are commercially available in kit form from, inter alia, Invitrogen, San Diego Calif. (the "MaxBac" kit). These techniques are generally known to those skilled in the art and are described fully in Summers and Smith, Texas Agricultural Experiment Station Bulletin No. 1555 (1987). Particularly suitable host cells for use in this system include insect cells such as Drosophila S2 and Spodoptera Sf9 cells.

There are many plant cell culture and whole plant genetic expression systems known in the art. Examples of suitable plant cellular genetic expression systems include those described in U.S. Pat. No. 5,693,506; U.S. Pat. No. 5,659, 122; and U.S. Pat. No. 5,608,143. Additional examples of genetic expression in plant cell culture has been described by Zenk, Phytochemistry 30, 3861-3863 (1991).

In particular, all plants from which protoplasts can be isolated and cultured to give whole regenerated plants can be utilised, so that whole plants are recovered which contain the transferred gene. Practically all plants can be regenerated from cultured cells or tissues, including but not limited to all major species of sugar cane, sugar beet, cotton, fruit and other trees, legumes and vegetables.

Examples of particularly preferred bacterial host cells include *streptococci, staphylococci, E. coli, Streptomyces* and *Bacillus subtilis* cells.

Examples of particularly suitable host cells for fungal expression include yeast cells (for example, *S. cerevisiae*) and *Aspergillus* cells.

Any number of selection systems are known in the art that may be used to recover transformed cell lines. Examples include the herpes simplex virus thymidine kinase (Wigler, M. et al. (1977) Cell 11:223-32) and adenine phosphoribosyltransferase (Lowy, I. et al. (1980) Cell 22:817-23) genes that can be employed in tk$^-$ or aprt$^\pm$ cells, respectively.

Also, antimetabolite, antibiotic or herbicide resistance can be used as the basis for selection; for example, dihydrofolate reductase (DHFR) that confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al. (1981) J. Mol. Biol. 150:1-14) and als or pat, which confer resistance to chlorsulfuron and phosphinotricin acetyltransferase, respectively. Additional selectable genes have been described, examples of which will be clear to those of skill in the art.

Although the presence or absence of marker gene expression suggests that the gene of interest is also present, its presence and expression may need to be confirmed. For example, if the relevant sequence is inserted within a marker gene sequence, transformed cells containing the appropriate sequences can be identified by the absence of marker gene function. Alternatively, a marker gene can be placed in tandem with a sequence encoding a polypeptide of the invention under the control of a single promoter. Expression of the marker gene in response to induction or selection usually indicates expression of the tandem gene as well.

Alternatively, host cells that contain a nucleic acid sequence encoding a polypeptide of the invention and which express said polypeptide may be identified by a variety of procedures known to those of skill in the art. These procedures include, but are not limited to, DNA-DNA or DNA-RNA hybridizations and protein bioassays, for example, fluorescence activated cell sorting (FACS) or immunoassay techniques (such as the enzyme-linked immunosorbent assay [ELISA] and radioimmunoassay [RIA]), that include membrane, solution, or chip based technologies for the detection and/or quantification of nucleic acid or protein (see Hampton, R. et al (1990) Serological Methods, a Laboratory Manual, APS Press, St Paul, Minn.) and Maddox, D. E. et al. (1983) J. Exp. Med, 158, 1211-1216).

A wide variety of labels and conjugation techniques are known by those skilled in the art and may be used in various nucleic acid and amino acid assays. Means for producing labelled hybridization or PCR probes for detecting sequences related to nucleic acid molecules encoding polypeptides of the present invention include oligolabelling, nick translation, end-labelling or PCR amplification using a labelled polynucleotide. Alternatively, the sequences encoding the polypeptide of the invention may be cloned into a vector for the production of an MRNA probe. Such vectors are known in the art, are commercially available, and may be used to synthesise RNA probes in vitro by addition of an appropriate RNA polymerase such as T7, T3 or SP6 and labelled nucleotides. These procedures may be conducted using a variety of commercially available kits (Pharmacia & Upjohn, (Kalamazoo, Mich.); Promega (Madison Wis.); and U.S. Biochemical Corp. (Cleveland, Ohio)).

Suitable reporter molecules or labels, which may be used for ease of detection, include radionucleides, enzymes and fluorescent, chemiluminescent or chromogenic agents as well as substrates, cofactors, inhibitors, magnetic particles, and the like.

Nucleic acid molecules according to the present invention may also be used to create transgenic animals, particularly rodent animals. Such transgenic animals form a further aspect of the present invention. This may be done locally by modification of somatic cells, or by germ line therapy to incorporate heritable modifications. Such transgenic animals may be particularly useful in the generation of animal models for drug molecules effective as modulators of the polypeptides of the present invention.

The polypeptide can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography is particularly useful for purification. Well known techniques for refolding proteins may be employed to regenerate an active conformation when the polypeptide is denatured during isolation and or purification.

Specialised vector constructions may also be used to facilitate purification of proteins, as desired, by joining sequences encoding the polypeptides of the invention to a nucleotide sequence encoding a polypeptide domain that will facilitate purification of soluble proteins. Examples of such purification-facilitating domains include metal chelating peptides such as histidine-tryptophan modules that allow purification on immobilised metals, protein A domains that allow purification on immobilised immunoglobulin, and the domain utilised in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the polypeptide of the invention may be used to facilitate purification. One such expression vector provides for expression of a fusion protein containing the polypeptide of the invention fused to several histidine residues preceding a thioredoxin or an enterokinase cleavage site. The histidine residues facilitate purification by IMAC (immobilised metal ion affinity chromatography as described in Porath, J. et al. (1992), Prot. Exp. Purif. 3: 263-281) while the thioredoxin or enterokinase cleavage site provides a means for purifying the polypeptide from the fusion protein. A discussion of vectors which contain fusion proteins is provided in Kroll, D. J. et al. (1993; DNA Cell Biol. 12:441-453).

If the polypeptide is to be expressed for use in screening assays, generally it is preferred that it be produced at the surface of the host cell in which it is expressed. In this event, the host cells may be harvested prior to use in the screening assay, for example using techniques such as fluorescence activated cell sorting (FACS) or immunoaffinity techniques. If the polypeptide is secreted into the medium, the medium can be recovered in order to recover and purify the expressed polypeptide. If polypeptide is produced intracellularly, the cells must first be lysed before the polypeptide is recovered.

The polypeptide of the invention can be used to screen libraries of compounds in any of a variety of drug screening techniques. Such compounds may activate (agonise) or inhibit (antagonise) the level of expression of the gene or the activity of the polypeptide of the invention and form a further aspect of the present invention. Preferred compounds are effective to alter the expression of a natural gene which encodes a polypeptide of the first aspect of the invention or to regulate the activity of a polypeptide of the first aspect of the invention.

Agonist or antagonist compounds may be isolated from, for example, cells, cell-free preparations, chemical libraries or natural product mixtures. These agonists or antagonists may be natural or modified substrates, ligands, enzymes, receptors or structural or functional mimetics. For a suitable review of such screening techniques, see Coligan et al., Current Protocols in Immunology 1(2): Chapter 5 (1991).

Compounds that are most likely to be good antagonists are molecules that bind to the polypeptide of the invention without inducing the biological effects of the polypeptide upon binding to it. Potential antagonists include small organic molecules, peptides, polypeptides and antibodies that bind to the polypeptide of the invention and thereby inhibit or extinguish its activity. In this fashion, binding of the polypeptide to normal cellular binding molecules may be inhibited, such that the normal biological activity of the polypeptide is prevented.

The polypeptide of the invention that is employed in such a screening technique may be free in solution, affixed to a solid support, borne on a cell surface or located intracellularly. In general, such screening procedures may involve using appropriate cells or cell membranes that express the polypeptide that are contacted with a test compound to observe binding, or stimulation or inhibition of a functional response. The functional response of the cells contacted with the test compound is then compared with control cells that were not contacted with the test compound. Such an assay may assess whether the test compound results in a signal generated by activation of the polypeptide, using an appropriate detection system. Inhibitors of activation are generally assayed in the presence of a known agonist and the effect on activation by the agonist in the presence of the test compound is observed.

Methods for generating detectable signals in the types of assays described herein will be known to those of skill in the art. A particular example is cotransfecting a construct expressing a polypeptide according to the invention, or a fragment that is responsible for binding to target, in fusion with the GAL4 DNA binding domain, into a cell together with a reporter plasmid, an example of which is pFR-Luc (Stratagene Europe, Amsterdam, The Netherlands). This particular plasmid contains a synthetic promoter with five tandem repeats of GAL4 binding sites that control the expression of the luciferase gene. When a potential target or ligand is added to the cells, it will bind the GAL4-polypeptide fusion and induce transcription of the luciferase gene. The level of the luciferase expression can be monitored by its activity using a luminescence reader (see, for example, Lehman et al. JBC 270, 12953, 1995; Pawar et al. JBC, 277, 39243, 2002).

A further preferred method for identifying an agonist or antagonist of a polypeptide of the invention comprises:
(a) contacting a labelled or unlabeled compound with the polypeptide immobilized on any solid support (for example beads, plates, matrix support, chip) and detection of the compound by measuring the label or the presence of the compound itself; or
(b) contacting a cell expressing on the surface thereof the polypeptide, by means of artificially anchoring it to the cell membrane, or by constructing a chimeric receptor being associated with a second component capable of providing a detectable signal in response to the binding of a compound to the polypeptide, with a compound to be screened under conditions to permit binding to the polypeptide; and
(c) determining whether the compound binds to and activates or inhibits the polypeptide by comparing the level of a signal generated from the interaction of the compound with the polypeptide with the level of a signal in the absence of the compound.

For example, a method such as FRET detection of a ligand bound to the polypeptide in the presence of peptide co-activators (Norris et al., Science 285, 744, 1999) might be used.

In further preferred embodiments, the general methods that are described above may further comprise conducting the identification of agonist or antagonist in the presence of labelled or unlabelled ligand for the polypeptide.

In another embodiment of the method for identifying agonist or antagonist of a polypeptide of the present invention comprises:
determining the inhibition of binding of a ligand to the polypeptide of the invention on any solid or cellular surface thereof, in the presence of a candidate compound under conditions to permit binding to the polypeptide, and determining the amount of ligand bound to the polypeptide. A compound capable of causing reduction of binding of a ligand is considered to be a competitor which may act as an agonist or antagonist. Preferably the ligand is labelled.

More particularly, a method of screening for a polypeptide antagonist or agonist compound comprises the steps of:
(a) incubating a labelled ligand with a polypeptide according to the invention on any solid support or the cell surface, or a cell membrane containing a polypeptide of the invention.
(b) measuring the amount of labelled ligand bound to the polypeptide on the solid support, whole cell or the cell membrane;
(c) adding a candidate compound to a mixture of labelled ligand and immobilized polypeptide on the solid support, the whole cell or the cell membrane of step (a) and allowing the mixture to attain equilibrium;
(d) measuring the amount of labelled ligand bound to the immobilized polypeptide or the whole cell or the cell membrane after step (c); and
(e) comparing the difference in the labelled ligand bound in step (b) and (d), such that the compound which causes the reduction in binding in step (d) is considered to be an agonist or antagonist.

The polypeptides may be found to modulate a variety of physiological and pathological processes in a dose-dependent manner in the above-described assays. Thus, the "fimctional equivalents" of the polypeptides of the invention include polypeptides that exhibit any of the same modulatory activities in the above-described assays in a dose-dependent manner. Although the degree of dose-dependent activity need not be identical to that of the polypeptides of the invention, preferably the "functional equivalents" will exhibit substantially similar dose-dependence in a given activity assay compared to the polypeptides of the invention.

In certain of the embodiments described above, simple binding assays may be used, in which the adherence of a test compound to a surface bearing the polypeptide is detected by means of a label directly or indirectly associated with the test compound or in an assay involving competition with a labelled competitor. In another embodiment, competitive drug screening assays may be used, in which neutralising antibodies that are capable of binding the polypeptide specifically compete with a test compound for binding. In this manner, the antibodies can be used to detect the presence of any test compound that possesses specific binding affinity for the polypeptide.

Assays may also be designed to detect the effect of added test compounds on the production of MRNA encoding the polypeptide in cells. For example, an ELISA may be constructed that measures secreted or cell-associated levels of polypeptide using monoclonal or polyclonal antibodies by standard methods known in the art, and this can be used to search for compounds that may inhibit or enhance the production of the polypeptide from suitably manipulated cells or tissues. The formation of binding complexes between the polypeptide and the compound being tested may then be measured.

Assay methods that are also included within the terms of the present invention are those that involve the use of the genes and polypeptides of the invention in overexpression or ablation assays. Such assays involve the manipulation of levels of these genes/polypeptides in cells and assessment of the impact of this manipulation event on the physiology of the manipulated cells. For example, such experiments reveal details of signaling and metabolic pathways in which the particular genes/polypeptides are implicated, generate information regarding the identities of polypeptides with which the studied polypeptides interact and provide clues as to methods by which related genes and proteins are regulated.

Another technique for drug screening which may be used provides for high throughput screening of compounds having suitable binding affinity to the polypeptide of interest (see International patent application WO84/03564). In this method, large numbers of different small test compounds are synthesised on a solid substrate, which may then be reacted with the polypeptide of the invention and washed. One way of immobilising the polypeptide is to use non-neutralising antibodies. Bound polypeptide may then be detected using methods that are well known in the art. Purified polypeptide can also be coated directly onto plates for use in the aforementioned drug screening techniques.

The polypeptide of the invention may be used to identify membrane-bound or soluble receptors, through standard receptor binding techniques that are known in the art, such as ligand binding and crosslinking assays in which the polypeptide is labelled with a radioactive isotope, is chemically modified, or is fused to a peptide sequence that facilitates its detection or purification, and incubated with a source of the putative receptor (for example, a composition of cells, cell membranes, cell supernatants, tissue extracts, or bodily fluids). The efficacy of binding may be measured using biophysical techniques such as surface plasmon resonance and spectroscopy. Binding assays may be used for the purification and cloning of the receptor, but may also identify agonists and antagonists of the polypeptide, that compete with the binding of the polypeptide to its receptor. Standard methods for conducting screening assays are well understood in the art.

The invention also includes a screening kit useful in the methods for identifying agonists, antagonists, ligands, receptors, substrates, enzymes, that are described above.

The invention includes the agonists, antagonists, ligands, receptors, substrates and enzymes, and other compounds which modulate the activity or antigenicity of the polypeptide of the invention discovered by the methods that are described above.

The invention also provides pharmaceutical compositions comprising a polypeptide, nucleic acid, ligand or compound of the invention in combination with a suitable pharmaceutical carrier. These compositions may be suitable as therapeutic or diagnostic reagents, as vaccines, or as other immunogenic compositions, as outlined in detail below.

According to the terminology used herein, a composition containing a polypeptide, nucleic acid, ligand or compound [X] is "substantially free of" impurities [herein, Y] when at least 85% by weight of the total X+Y in the composition is X. Preferably, X comprises at least about 90% by weight of the total of X+Y in the composition, more preferably at least about 95%, 98% or even 99% by weight.

The pharmaceutical compositions should preferably comprise a therapeutically effective amount of the polypeptide, nucleic acid molecule, ligand, or compound of the invention. The term "therapeutically effective amount" as used herein refers to an amount of a therapeutic agent needed to treat, ameliorate, or prevent a targeted disease or condition, or to exhibit a detectable therapeutic or preventative effect. For any compound, the therapeutically effective dose can be estimated initially either in cell culture assays, for example, of neoplastic cells, or in animal models, usually mice, rabbits, dogs, or pigs. The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective dose will be from 0.01 mg/kg to 50 mg/kg, preferably 0.05 mg/kg to 10 mg/kg. Compositions may be administered individually to a patient or may be administered in combination with other agents, drugs or hormones.

A pharmaceutical composition may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmfull to the individual receiving the composition, and which may be administered without undue toxicity. Suitable carriers may be large, slowly metabolised macromolecules such as proteins, polysaccharides, polylactic acids, polyglycolic acids, polymeric amino acids, amino acid copolymers and inactive virus particles.

Pharmaceutically acceptable salts can be used therein, for example, mineral acid salts such as hydrochlorides, hydrobromides, phosphates, sulphates, and the like; and the salts of organic acids such as acetates, propionates, malonates, benzoates, and the like. A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The pharmaceutical compositions utilised in this invention may be administered by any number of routes including, but not limited to, oral, intravenous, intramuscular, intra-arterial, intramedullary, intrathecal, intraventricular, transdermal or transcutaneous applications (for example, see WO98/20734), subcutaneous, intraperitoneal, intranasal, enteral, topical, sublingual, intravaginal or rectal means. Gene guns or hyposprays may also be used to administer the pharmaceutical compositions of the invention. Typically, the therapeutic compositions may be prepared as injectables, either as liquid solutions or suspensions; solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

If the activity of the polypeptide of the invention is in excess in a particular disease state, several approaches are available. One approach comprises administering to a subject an inhibitor compound (antagonist) as described above, along with a pharmaceutically acceptable carrier in an amount effective to inhibit the function of the polypeptide, such as by blocking the binding of ligands, substrates, enzymes, receptors, or by inhibiting a second signal, and thereby alleviating the abnormal condition. Preferably, such antagonists are antibodies. Most preferably, such antibodies are chimeric and/or humanised to minimise their immunogenicity, as described previously.

In another approach, soluble forms of the polypeptide that retain binding affinity for the ligand, substrate, enzyme, receptor, in question, may be administered. Typically, the polypeptide may be administered in the form of fragments that retain the relevant portions.

In an alternative approach, expression of the gene encoding the polypeptide can be inhibited using expression blocking techniques, such as the use of antisense nucleic acid molecules (as described above), either internally generated or separately administered. Modifications of gene expression can be obtained by designing complementary sequences or antisense molecules (DNA, RNA, or PNA) to the control, 5' or regulatory regions (signal sequence, promoters, enhancers and introns) of the gene encoding the polypeptide. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, Molecular and Immunologic Approaches, Futura Publishing Co., Mt. Kisco, N.Y.). The complementary sequence or antisense molecule may also be designed to block translation of mRNA by preventing the transcript from binding to ribosomes. Such oligonucleotides may be administered or may be generated in situ from expression in vivo.

In addition, expression of the polypeptide of the invention may be prevented by using ribozymes specific to its encoding mRNA sequence. Ribozymes are catalytically active RNAs that can be natural or synthetic (see for example Usman, N, et al., Curr. Opin. Struct. Biol (1996) 6(4), 527-33). Synthetic ribozymes can be designed to specifically cleave mRNAs at selected positions thereby preventing translation of the mRNAs into functional polypeptide. Ribozymes may be synthesised with a natural ribose phosphate backbone and natural bases, as normally found in RNA molecules. Alternatively the ribozymes may be synthesised with non-natural backbones, for example, 2'-O-methyl RNA, to provide protection from ribonuclease degradation and may contain modified bases.

RNA molecules may be modified to increase intracellular stability and half-life. Possible modifications include, but are not limited to, the addition of flanking sequences at the 5'and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of non-traditional bases such as inosine, queosine and butosine, as well as acetyl-, methyl-, thio- and similarly modified forms of adenine, cytidine, guanine, thymine and uridine which are not as easily recognised by endogenous endonucleases.

For treating abnormal conditions related to an under-expression of the polypeptide of the invention and its activity, several approaches are also available. One approach comprises administering to a subject a therapeutically effective amount of a compound that activates the polypeptide, i.e., an agonist as described above, to alleviate the abnormal condition. Alternatively, a therapeutic amount of the polypeptide in combination with a suitable pharmaceutical carrier may be administered to restore the relevant physiological balance of polypeptide.

Gene therapy may be employed to effect the endogenous production of the polypeptide by the relevant cells in the subject. Gene therapy is used to treat permanently the inappropriate production of the polypeptide by replacing a defective gene with a corrected therapeutic gene.

Gene therapy of the present invention can occur in vivo or ex vivo. Ex vivo gene therapy requires the isolation and purification of patient cells, the introduction of a therapeutic gene and introduction of the genetically altered cells back into the patient. In contrast, in vivo gene therapy does not require isolation and purification of a patient's cells.

The therapeutic gene is typically "packaged" for administration to a patient. Gene delivery vehicles may be non-viral, such as liposomes, or replication-deficient viruses, such as adenovirus as described by Berkner, K. L., in Curr. Top. Microbiol. Immunol., 158, 39-66 (1992) or adeno-associated virus (AAV) vectors as described by Muzyczka, N., in Curr. Top. Microbiol. Immunol., 158, 97-129 (1992) and U.S. Pat. No. 5,252,479. For example, a nucleic acid molecule encoding a polypeptide of the invention may be engineered for expression in a replication-defective retroviral vector. This expression construct may then be isolated and introduced into a packaging cell transduced with a retroviral plasmid vector containing RNA encoding the polypeptide, such that the packaging cell now produces infectious viral particles containing the gene of interest. These producer cells may be administered to a subject for engineering cells in vivo and expression of the polypeptide in vivo (see Chapter 20, Gene Therapy and other Molecular Genetic-based Therapeutic Approaches, (and references cited therein) in Human Molecular Genetics (1996), T Strachan and A P Read, BIOS Scientific Publishers Ltd).

Another approach is the administration of "naked DNA" in which the therapeutic gene is directly injected into the bloodstream or muscle tissue.

In situations in which the polypeptides or nucleic acid molecules of the invention are disease-causing agents, the invention provides that they can be used in vaccines to raise antibodies against the disease causing agent.

Vaccines according to the invention may either be prophylactic (i.e. to prevent infection) or therapeutic (i.e. to treat disease after infection). Such vaccines comprise immunising antigen(s), immunogen(s), polypeptide(s), protein(s) or nucleic acid, usually in combination with pharmaceutically-acceptable carriers as described above, which include any carrier that does not itself induce the production of antibodies harmful to the individual receiving the composition. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, and other pathogens.

Since polypeptides may be broken down in the stomach, vaccines comprising polypeptides are preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient, and aqueous and non-aqueous sterile suspensions which may include suspending agents or thickening agents.

The vaccine formulations of the invention may be presented in unit-dose or multi-dose containers. For example, sealed ampoules and vials and may be stored in a freeze-dried condition requiring only the addition of the sterile liquid carrier immediately prior to use. The dosage will depend on the specific activity of the vaccine and can be readily determined by routine experimentation.

Genetic delivery of antibodies that bind to polypeptides according to the invention may also be effected, for example, as described in International patent application WO98/55607.

The technology referred to as jet injection (see, for example, www.powderject.com) may also be useful in the formulation of vaccine compositions.

A number of suitable methods for vaccination and vaccine delivery systems are described in International patent application WO00/29428.

This invention also relates to the use of nucleic acid molecules according to the present invention as diagnostic reagents. Detection of a mutated form of the gene characterised by the nucleic acid molecules of the invention which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acid molecules for diagnosis may be obtained from a subject's cells, such as from blood, urine, saliva, tissue biopsy or autopsy material. The genomic DNA may be used directly for detection or may be amplified enzymatically by using PCR, ligase chain reaction (LCR), strand displacement amplification (SDA), or other amplification techniques (see Saiki et aL, Nature, 324, 163-166 (1986); Bej, et aL, Crit. Rev. Biochem. Molec. Biol., 26, 301-334 (1991); Birkenmeyer et al., J. Virol. Meth., 35, 117-126 (1991); Van Brunt, J., Bio/Technology, 8, 291-294 (1990)) prior to analysis.

In one embodiment, this aspect of the invention provides a method of diagnosing a disease in a patient, comprising assessing the level of expression of a natural gene encoding a polypeptide according to the invention and comparing said level of expression to a control level, wherein a level that is different to said control level is indicative of disease. The method may comprise the steps of:

a) contacting a sample of tissue from the patient with a nucleic acid probe under stringent conditions that allow the formation of a hybrid complex between a nucleic acid molecule of the invention and the probe;
b) contacting a control sample with said probe under the same conditions used in step a);
c) and detecting the presence of hybrid complexes in said samples;

wherein detection of levels of the hybrid complex in the patient sample that differ from levels of the hybrid complex in the control sample is indicative of disease.

A further aspect of the invention comprises a diagnostic method comprising the steps of:

a) obtaining a tissue sample from a patient being tested for disease;
b) isolating a nucleic acid molecule according to the invention from said tissue sample; and
c) diagnosing the patient for disease by detecting the presence of a mutation in the nucleic acid molecule which is associated with disease.

To aid the detection of nucleic acid molecules in the above-described methods, an amplification step, for example using PCR, may be included.

Deletions and insertions can be detected by a change in the size of the amplified product in comparison to the normal genotype. Point mutations can be identified by hybridizing amplified DNA to labelled RNA of the invention or alternatively, labelled antisense DNA sequences of the invention. Perfectly-matched sequences can be distinguished from mismatched duplexes by RNase digestion or by assessing differences in melting temperatures. The presence or absence of the mutation in the patient may be detected by contacting DNA with a nucleic acid probe that hybridises to the DNA under stringent conditions to form a hybrid double-stranded molecule, the hybrid double-stranded molecule having an unhybridised portion of the nucleic acid probe strand at any portion corresponding to a mutation associated with disease; and detecting the presence or absence of an unhybridised portion of the probe strand as an indication of the presence or absence of a disease-associated mutation in the corresponding portion of the DNA strand.

Such diagnostics are particularly useful for prenatal and even neonatal testing.

Point mutations and other sequence differences between the reference gene and "mutant" genes can be identified by other well-known techniques, such as direct DNA sequencing or single-strand conformational polymorphism, (see Orita et al., Genomics, 5, 874-879 (1989)). For example, a sequencing primer may be used with double-stranded PCR product or a single-stranded template molecule generated by a modified PCR. The sequence determination is performed by conventional procedures with radiolabelled nucleotides or by automatic sequencing procedures with fluorescent-tags. Cloned DNA segments may also be used as probes to detect specific DNA segments. The sensitivity of this method is greatly enhanced when combined with PCR. Further, point mutations and other sequence variations, such as polymorphisms, can be detected as described above, for example, through the use of allele-specific oligonucleotides for PCR amplification of sequences that differ by single nucleotides.

DNA sequence differences may also be detected by alterations in the electrophoretic mobility of DNA fragments in gels, with or without denaturing agents, or by direct DNA sequencing (for example, Myers et al., Science (1985) 230: 1242). Sequence changes at specific locations may also be revealed by nuclease protection assays, such as RNase and S1 protection or the chemical cleavage method (see Cotton et al., Proc. Natl. Acad. Sci. USA (1985) 85: 4397-4401).

In addition to conventional gel electrophoresis and DNA sequencing, mutations such as microdeletions, aneuploidies, translocations, inversions, can also be detected by in situ analysis (see, for example, Keller et al, DNA Probes, 2nd Ed., Stockton Press, New York, N.Y., USA (1993)), that is, DNA or RNA sequences in cells can be analysed for mutations without need for their isolation and/or immobilisation onto a membrane. Fluorescence in situ hybridization (FISH) is presently the most commonly applied method and numerous reviews of FISH have appeared (see, for example, Trachuck et al, Science, 250, 559-562 (1990), and Trask et al., Trends, Genet., 7, 149-154 (1991)).

In another embodiment of the invention, an array of oligonucleotide probes comprising a nucleic acid molecule according to the invention can be constructed to conduct efficient screening of genetic variants, mutations and polymorphisms. Array technology methods are well known and have general applicability and can be used to address a variety of questions in molecular genetics including gene expression, genetic linkage, and genetic variability (see for example: M. Chee et al., Science (1996), Vol 274, pp 610-613).

In one embodiment, the array is prepared and used according to the methods described in PCT application WO95/11995 (Chee et al.); Lockhart, D. J. et al. (1996) Nat. Biotech. 14: 1675-1680); and Schena, M. et al. (1996) Proc. Natl. Acad. Sci. 93: 10614-10619). Oligonucleotide pairs may range from two to over one million. The oligomers are synthesized at designated areas on a substrate using a light-directed chemical process. The substrate may be paper, nylon or other type of membrane, filter, chip, glass slide or any other suitable solid support. In another aspect, an oligonucleotide may be synthesized on the surface of the substrate by using a chemical coupling procedure and an ink jet application apparatus, as described in PCT application W095/25116 (Baldeschweiler et al.). In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and over one million which lends itself to the efficient use of commercially-available instrumentation.

In addition to the methods discussed above, diseases may be diagnosed by methods comprising determining, from a sample derived from a subject, an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods.

Assay techniques that can be used to determine levels of a polypeptide of the present invention in a sample derived from a host are well-known to those of skill in the art and are discussed in some detail above (including radioimmunoassays, competitive-binding assays, Western Blot analysis and ELISA assays). This aspect of the invention provides a diagnostic method which comprises the steps of: (a) contacting a ligand as described above with a biological sample under conditions suitable for the formation of a ligand-polypeptide complex; and (b) detecting said complex.

Protocols such as ELISA, RIA, and FACS for measuring polypeptide levels may additionally provide a basis for diagnosing altered or abnormal levels of polypeptide expression. Normal or standard values for polypeptide expression are established by combining body fluids or cell extracts taken from normal mammalian subjects, preferably humans, with antibody to the polypeptide under conditions suitable for complex formation The amount of standard complex formation may be quantified by various methods, such as by photometric means.

Antibodies which specifically bind to a polypeptide of the invention may be used for the diagnosis of conditions or diseases characterised by expression of the polypeptide, or in assays to monitor patients being treated with the polypeptides, nucleic acid molecules, ligands and other compounds of the invention. Antibodies useful for diagnostic purposes may be prepared in the same manner as those described above for therapeutics. Diagnostic assays for the polypeptide include methods that utilise the antibody and a label to detect the polypeptide in human body fluids or extracts of cells or tissues. The antibodies may be used with or without modification, and may be labelled by joining them, either covalently or non-covalently, with a reporter molecule. A wide variety of reporter molecules known in the art may be used, several of which are described above.

Quantities of polypeptide expressed in subject, control and disease samples from biopsied tissues are compared with the standard values. Deviation between standard and subject values establishes the parameters for diagnosing disease. Diagnostic assays may be used to distinguish between absence, presence, and excess expression of polypeptide and to monitor regulation of polypeptide levels during therapeutic intervention. Such assays may also be used to evaluate the efficacy of a particular therapeutic treatment regimen in animal studies, in clinical trials or in monitoring the treatment of an individual patient.

A diagnostic kit of the present invention may comprise:
(a) a nucleic acid molecule of the present invention;
(b) a polypeptide of the present invention; or
(c) a ligand of the present invention.

In one aspect of the invention, a diagnostic kit may comprise a first container containing a nucleic acid probe that hybridises under stringent conditions with a nucleic acid molecule according to the invention; a second container containing primers useful for amplifying the nucleic acid molecule; and instructions for using the probe and primers for facilitating the diagnosis of disease. The kit may further comprise a third container holding an agent for digesting unhybridised RNA.

In an alternative aspect of the invention, a diagnostic kit may comprise an array of nucleic acid molecules, at least one of which may be a nucleic acid molecule according to the invention.

To detect polypeptide according to the invention, a diagnostic kit may comprise one or more antibodies that bind to a polypeptide according to the invention; and a reagent useful for the detection of a binding reaction between the antibody and the polypeptide.

Such kits will be of use in diagnosing a disease or susceptibility to disease in which members of the TNF-like family of proteins are implicated. Such diseases may include cell proliferative disorders, autoimmune/inflammatory disorders, genetic disorders, developmental disorders, nervous system disorders, metabolic disorders, infections and other pathological conditions; particularly immune disorders, such as autoimmune disease, rheumatoid arthritis, osteoarthritis, psoriasis, systemic lupus erythematosus, and multiple sclerosis, inflammatory disorders, such as allergy, rhinitis, conjunctivitis, glomerulonephritis, uveitis, Crohn's disease, ulcerative colitis, inflammatory bowel disease, pancreatitis, digestive system inflammation, sepsis, endotoxic shock, septic shock, cachexia, myalgia, ankylosing spondylitis, myasthenia gravis, post-viral fatigue syndrome, pulmonary disease, respiratory distress syndrome, asthma, chronic-obstructive pulmonary disease, airway inflammation, wound healing, endometriosis, dermatological disease, Behcet's disease, neoplastic disorders, such as melanoma, sarcoma, renal tumour, colon tumour, haematological disease, myeloproliferative disorder, diseases associated with the disregulation of apoptosis, Hodgkin's disease, osteoporosis, obesity, diabetes, gout, cardiovascular disorders, reperfusion injury, atherosclerosis, ischaemic heart disease, cardiac failure, stroke, liver disease, AIDS, AIDS related complex, neurological disorders, male infertility, ageing and infections, including plasmodium infection, bacterial infection and viral infection, hereditary diseases, including hyper IgM syndrome (HIM, CD40L), type I autoimmune lymphoproliferative syndrome (ALPS, Fas/FasL), TNF-R1-associated periodic fever syndrome (TRAPS, TNF-R1), hypohidrotic ectodermal dysplasia (HED, EDA/EDAR), familial expansile osteolysis (FEO, RANK) and other pathological conditions. Preferably the disease is selected from autoimmune diseases, autoimmune inner ear disease, Labyrinthitis, Ménière disease and Ménière syndrome, Perilymphatic or labyrinthine fistula, Tinnitus, neurodegenerative diseases, amyloidosis, Alzheimer's disease, Parkinson's disease, familial dementia, inflammation (joint pain, swelling, anemia, or septic shock), infectious diseases, parasitic diseases, microbial diseases, bacterial diseases, viral diseases (HIV, HTLV, MuLV, *Streptococcus pneumoniae* and *Ascaris lumbricoides* infections), glomerulonephritis, obesity, diabetes, diabetes mellitus, Schmid metaphyseal chondrodysplasia, corneal endothelial dystrophies, posterior polymorphous corneal dystrophy (PPCD), Fuchs endothelial corneal dystrophy (FECD), atherosclerosis, scurvy, cancer, gastrointestinal stromal tumours, osteosarcoma, chondroblastoma, giant cell tumor, spondylometaphyseal dysplasia japanese type (SMD), lymphomas (Non-Hodgkin's lymphoma (NHL), follicular lymphomas, Burkitt's lymphoma, mantle cell lymphoma (MCL), multiple myeloma (MM), leukemia (chronic lymphocytic leukemia/ small lymphocity lymphoma (CLL/SLL)), diffuse large cell B cell lymphoma (DLCL), B cell hyperplasia, Osteogenesis Imperfecta, Ehlers-Danlos syndrome, susceptibility to dissection of cervical arteries, aortic aneurysm, otospondylomegaepiphyseal dysplasia, hearing loss (deafness), Weissenbacher-Zweymuller syndrome, bone or skeletal disease, late-onset retinal degeneration (L-ORD), age-related macular degeneration (AMD), blindness, arthritis, rheumatoid arthritis (RA), osteoarthritis, lyme arthritis, juvenile chronic arthritis, spondyloarthropathies, Systemic lupus erythematosus (SLE), Sjögren syndrome, demyelinating diseases of the central and peripheral nervous systems such as multiple sclerosis, idiopathic demyelinating polyneuropathy or Guillain-Barre syndrome, and chronic inflammatory demyelinating polyneuropathy, myasthenia gravis, bronchitis, emphysema, renal failure (glomerulonephritis, vasculitis, nephritis or pyrlonephritis), renal neoplasms, renal cell carcinomas, renal tumour, light chain neuropathy or amyloidosis, acute or chronic immune disease associated with organ transplantation, organ transplant rejection, graft-versus-host disease, Crohn's Disease, systemic sclerosis, idiopathic inflammatory myopathies, systemic vasculitis, sarcoidosis, autoimmune hemolytic anemia, autoimmune thrombocytopenia, thyroiditis, immune-mediated renal disease, hepatobiliary diseases such as infectious, autoimmune chronic active hepatitis, primary biliary cirrhosis, granulomatous hepatitis, and sclerosing cholangitis, inflammatory bowel disease, gluten-sensitive enteropathy, and Whipple's disease, autoimmune or immune-mediated skin diseases including bullous skin diseases, erythema multiforme and contact dermatitis, psoriasis, atopic dermatitis, food hypersensitivity and urticaria, immunologic diseases of the lung such as eosinophilic pneumonias, idiopathic pulmonary fibrosis and hypersensitivity pneumonitis, ulcerative colitis, inflammatory bowel disease, allergic diseases such as asthma, allergic rhinitis, sarcoidosis, female infertility, autoimmune thrombocytopenia, autoimmune thyroid disease, Hashimoto's disease, Sjogren's syndrome, ectodermal dysplasia, X-linked hypohidrotic ectodermal dysplasia (HED), inflammatory, ischemic or neoplastic diseases of the adrenal cortex, adrenal tumour, ganglioneuroblastoma, neuroblastoma, phaeochromocytomas, corstisol-producing adrenocortical adenomas, diseases linked to spinocerebellar degeneration, cerebellar diseases, olivopontocerebellar atrophy (OPCA) and/or Shy-Drager syndrome. Such kits may also be used for the detection of reproductive disorders including infertility.

Various aspects and embodiments of the present invention will now be described in more detail by way of example, with particular reference to the INSP163 polypeptides.

It will be appreciated that modification of detail may be made without departing from the scope of the invention.

BRIEF DESCRIPTION OF THE FIGURES

FIG. 1: Genome Threader output for INSP163 polypeptide sequence (SEQ ID NO: 30).
KEY:
Top 7 (non-redundant) stand-alone-GT hits.
1gr3: Structure of the human collagen x nc1 trimer (contains a C-terminal c1q domain).
1c28: The crystal structure of a complment-1q family protein suggests an evolutionary link to tumor necrosis factor (c1q).
4tsv: High resolution crystal structure of a human TNF-alpha mutant (TNF)

Figure 4:
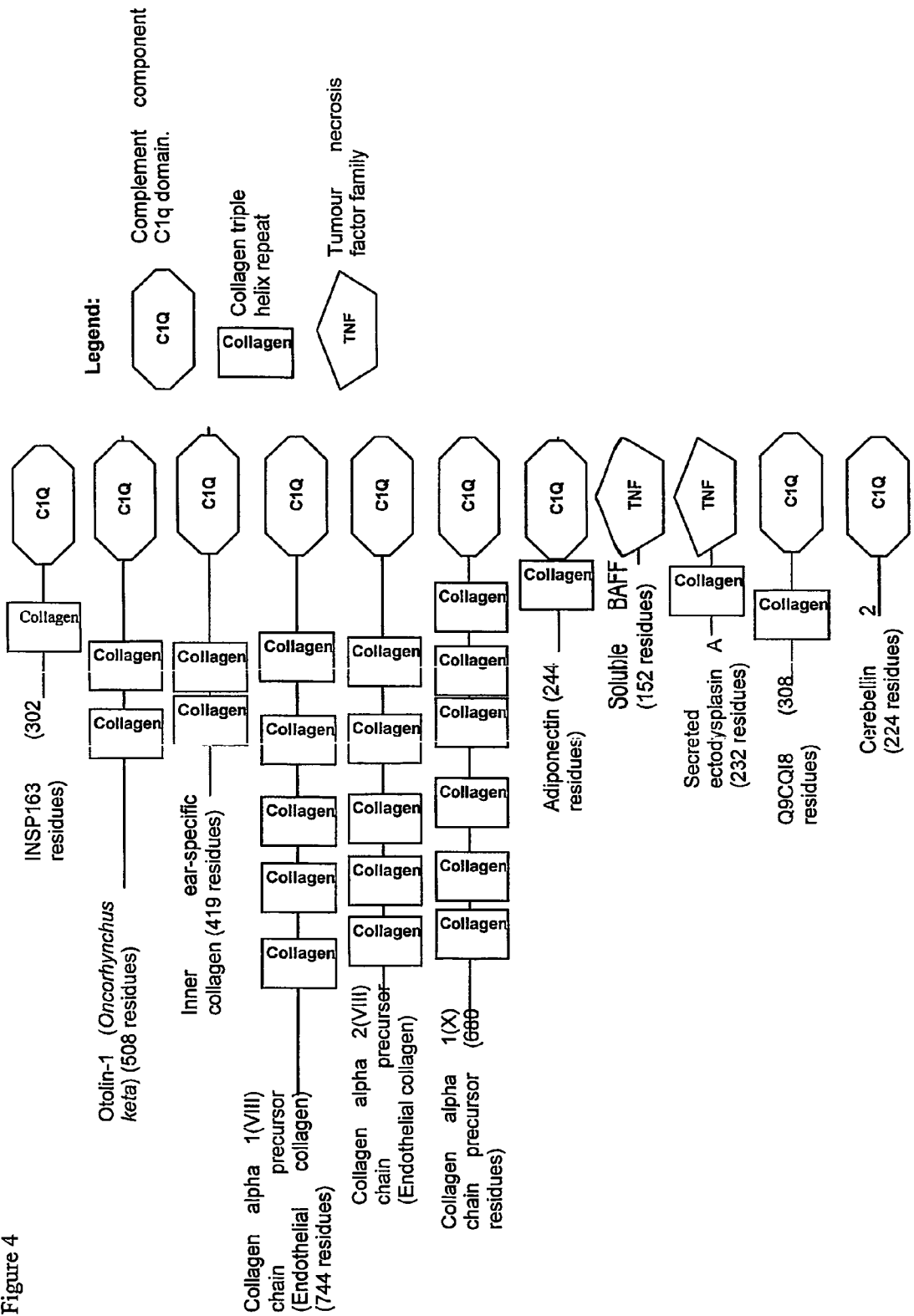

2tnf: 1.4 a resolution structure of mouse tumor necrosis factor, towards modulation of its selctivity and trimerisation (TNF)
1kxg: The 2.0 ang resolution structure of blys, b lymphocyte stimulator (TNF)
1d2q: Crystal structure of human trail (TNF)
1dg6: Crystal structure of apo21/trail (TNF)

FIG. 2: Nucleotide sequence (SEQ ID NO:49) with translation of the INSP163 PCR product (SEQ ID NO:30) cloned using primers INSP163-CP1 (SEQ ID NO:37) and INSP163-CP2 (SEQ ID NO:38). The c1q domain is boxed. The collagen domain is shaded. Position and sense of primers are indicated by arrows.

FIGS. 3A-3F: Polypeptide sequences of predicted biologically active products after proprotein cleavage (cleavage sites are indicated in table 1). A) INSP163-A (SEQ ID NO:4), B) INSP163-B (SEQ ID NO:6), C) INSP163-C (SEQ ID NO:8), D) INSP163-D (SEQ ID NO:10), E) INSP163-E (SEQ ID NO:12) and F) INSP163-F (SEQ ID NO:14).

FIG. 4: FIG. 3 represents a schematic domain representation of INSP163, inner ear specific structural protein (SwissProt Acc. Code: COLE_LEPMA), otolin-1 in fish otolith (SwissProt Acc. Code: OTO1_ONCKE), human alpha 1 and alpha 2 (VIII) chains (COL8A1, SwissProt Acc. Code: CA18_HUMAN and COL8A2, SwissProt Acc. Code: CA28_HUMAN), Collagen alpha 1(×) chain precursor (COL10A1, SwissProt Ace. Code: CA1A_HUMAN), adiponectin (SwissProt Acc. Code: APM1_HUMAN), tumor necrosis factor ligand superfamily member 13B (BAFF, TALL-1; SwissProt Acc. Code: T13B_HUMAN), Ectodysplasin A (EDA, SwissProt Acc. Code: EDA_HUMAN), cerebellin 2 (CBLN2, SwissProt Acc. Code: CBN2_HUMAN) and Mus musculus 18-day embryo whole body cDNA (SwissProt Acc. Code: Q9CQI8).

EXAMPLES

Example 1

Genome Threader

FIG. 1 shows the Genome Threader output for INSP163. Hits 5-9, which have between 68% and 84% confidence values, are for TNF proteins.

Example 2

INSP163 Signal Sequence

Using different prediction tools, two different signal peptides have been predicted for the INSP163 polypeptide. SignalP (Nielsen, H. et al. 1997, Protein Engineering, 10, 1-6; Nielsen, H., and Krogh, A.: Prediction of signal peptides and signal anchors by a hidden Markov model. In Proceedings of the Sixth International Conference on Intelligent Systems for Molecular Biology (ISMB 6), AAAI Press, Menlo Park, Calif., pp. 122-130 (1998)) predicts cleavage between residues 25 and 26. However, an internal prediction tool predicts cleavage between residues 20 and 21. Therefore there may be two alternative signal peptide cleavage sites.

Example 3

Cleavage sites for proprotein convertases have been identified in INSP163 (see table 1). The members of the subtilisin-like proprotein convertases and N-Arg dibasic convertases are proprotein convertases that process latent precursor proteins into their biologically active products (see review of Sheidah et al. 1999 Proc. Natl. Acad. Sci. 96(4):1321-6). Predicted active products resulting from the cleavages are INSP163-A, INSP163-B, INSP163-C, INSP163-D, INSP163-E and INSP163-F (FIG. 3). The proteases cut either before the c1q domain or before the collagen domain of INSP163. INSP163-A, INSP163-B and INSP163-C contain the c1q and collagen domains, whereas INSP163-D, INSP163-E and INSP163-F only harbour the c1q domain (deduced from FIG. 2).

Different members have been identified. Subtilisin/kexin isozyme-1 (SKI-1) protease is a mammalian subtilase composed of distinct functional domains. The subtilisin-like proprotein convertases are expressed extensively in mammalian neural and endocrine cells and play a major role in the proteolytic processing of both neuropeptide and peptide hormone precursors. Among the major substrates of SKI-1 are the sterol regulatory element-binding proteins, regulating cholesterol and fatty acid homeostasis. Other substrates include the stress response factor activating transcription factor-6, the brain-derived neurotrophic factor, and the surface glycoproteins of highly infectious viruses belonging to the family of Arenaviridae (Elagoz et al. 2002 J Biol Chem. 277(13):11265-75). The prohormone-processing yeast KEX2 protease can act as an intracellular membrane protein or a soluble, secreted endopeptidase. The protein is required for processing of precursors of alpha-factor and killer toxin. PCSK1 (proprotein convertase 1, NEC1) and PCSK2 (proprotein convertase 2, NEC2) are type I proinsulin-processing enzymes that play a key role in regulating insulin biosynthesis. They are also known to cleave proopiomelanocortin, prorenin, proenkephalin, prodynorphin, prosomatostatin and progastrin. PACE4 (paired basic amino acid cleaving system 4, SPC4) is a calcium-dependent serine endoprotease that can cleave precursor protein at their paired basic amino acid processing sites. Some of its substrates are transforming growth factor beta related proteins, proalbumin, and von Willebrand factor. Furin (PACE, paired basic amino acid cleaving enzyme, membrane associated receptor protein) is a serine endoprotease responsible for processing variety of substrates (proparathyroid hormone, transforming growth factor beta 1 precursor, proalbumin, pro-beta-secretase, membrane type-1 matrix metalloproteinase, beta subunit of pro-nerve growth factor and von Willebrand factor). PC7 (proprotein convertase subtilisin/kexin type 7) is a closely related to PACE and PACE4. This calcium-dependent serine endoprotease is concentrated in the trans-Golgi network, associated with the membranes, and is not secreted. It can process proalbumin. PC7 and furin are also thought to be one of the proteases responsible for the activation of HIV envelope glycoproteins gp160 and gp140.

N-Arg dibasic convertase (NDR) is a metalloendopeptidase primarily cloned from rat brain cortex and testis that cleaves peptide substrates on the N terminus of Arg residues in dibasic stretches. It hydrolyses polypeptides, preferably at -Xaa-+-Arg-Lys-, and less commonly at -Arg-+-Arg-Xaa-, in which Xaa is not Arg or Lys. It has been proved that it can cleave alpha-neoendorphin, ANF, dynorphin, preproneurotensin and somatostatin. Also there is an evidence for extracellular localization of active NDR.

TABLE 1

| Protein convertase | Motif | Residues |
|---|---|---|
| N-Arg dibasic convertase (nardilysine) cleavage site | RRP<br>LRK | 80-82<br>87-89 |

TABLE 1-continued

| Protein convertase | Motif | Residues |
|---|---|---|
| (Xaa-\|-Arg-Lys or Arg-\|-Arg-Xaa) | RRF | 131-133 |
|  | RRV | 162-164 |
| NEC1/NEC2 cleavage site | KRC | 89-91 |
| (Lys-Arg-\|-Xaa) | KRT | 166-168 |
| Proprotein convertase 7 (PC7, PCSK7) cleavage site (Arg-Xaa-Xaa-Xaa-[Arg/Lys]-Arg-\|-Xaa) | RRVDKRT | 162-168 |

Example 4

Cloning of INSP163

Preparation of Human cDNA Templates

First strand cDNA was prepared from a variety of human tissue total RNA samples (Clontech, Stratagene, Ambion, Biochain Institute and in-house preparations) using Superscript II or SuperScript II RNase H⁻ Reverse Transcriptase (Invitrogen) according to the manufacturer's protocol.

For SuperScript II: Oligo $(dT)_{15}$ primer (1 µl at 500 µg/ml) (Promega), 2 µg human total RNA, 1 µl 10 mM dNTP mix (10 mM each of dATP, dGTP, dCTP and dTTP at neutral pH) and sterile distilled water to a final volume of 12 µl were combined in a 1.5 ml Eppendorf tube, heated to 65° C. for 5 min and chilled on ice. The contents were collected by brief centrifugation and 4 µl of 5× First-Strand Buffer, 2 µl 0.1 M DTT, and 1 µl RnaseOUT™ Recombinant Ribonuclease Inhibitor (40 units/µl, Invitrogen) were added. The contents of the tube were mixed gently and incubated at 42° C. for 2 min, then 1 µl (200 units) of SuperScript II™ enzyme was added and mixed gently by pipetting. The mixture was incubated at 42° C. for 50 min and then inactivated by heating at 70° C. for 15 min. To remove RNA complementary to the cDNA, 1 µl (2 units) of E. coli RNase H (Invitrogen) was added and the reaction mixture incubated at 37° C. for 20 min.

For SuperScript III: 1 µl Oligo$(dT)_{20}$ primer (50 µM, Invitrogen), 2 µg human total RNA, 1 µl 10 mM dNTP mix (10 mM each of dATP, dGTP, dCTP and dTTP at neutral pH) and sterile distilled water to a final volume of 10 µl were combined in a 1.5 ml Eppendorf tube, heated to 65° C. for 5 min and then chilled on ice. For each RT reaction a cDNA synthesis mix was prepared as follows: 2 µl 10×RT buffer, 4 µl 25 nM $MgCl_2$, 2 µl 0.1M DTT, 1 µl RNaseOUT™ (40 U/µl) and 1 µl SuperScript III™ RT enzyme were combined in a separate tube and then 10 µl of this mix added to the tube containing the RNA/primer mixture. The contents of the tube were mixed gently, collected by brief centrifugation, and incubated at 50° C. for 50 min. The reaction was terminated by incubating at 80° C. for 5 min and the reaction mixture then chilled on ice and collected by brief centrifugation. To remove RNA complementary to the cDNA, 1 µl (2 units) of E. coli RNase H (Invitrogen) was added and the reaction mixture incubated at 37° C. for 20 min.

The final 21 µl reaction mix was diluted by adding 179 µl sterile water to give a total volume of 200 µl. This represented approximately 20 ng/µl of each individual cDNA template.

Gene Specific Cloning Primers for PCR

A pair of PCR primers having a length of between 18 and 30 bases were designed to amplify the full length of the INSP163 predicted cds using Primer Designer Software (Scientific & Educational Software, PO Box 72045, Durham, N.C. 27722-2045, USA). PCR primers were optimized to have a Tm close to 55±10° C. and a GC content of 40-60%.

Primers were selected which had high selectivity for the target sequence (INSP163) with little or no none specific priming.

PCR Amplification of INSP163 from Human cDNA Templates

Gene-specific cloning primers (INSP163-CP1 and INSP163-CP2, FIG. 2, Table 2) were designed to amplify a cDNA fragment of 929 bp covering the full length of the INSP163 cds. Interrogation of public EST sequence databases with the INSP163 prediction suggested that the sequence might be expressed in cDNA templates derived from normal kidney, Crohn's disease kidney and cancerous tissues. The primer pair was therefore used with individual cDNA samples from these sources as PCR templates. PCR was performed in a final volume of 50 µl containing 1× Platinum® Taq High Fidelity (HiFi) buffer, 2 nM MgSO$_4$, 200µM dNTPs, 0.2 µM of each cloning primer, 1 unit of Platinum® Taq DNA Polymerase High Fidelity (HiFi) (Invitrogen), approximately 20 ng of individual cDNA template, and 0×, 1× or 2×PCR$_x$ Enhancer solution (Invitrogen). Cycling was performed using an MJ Research DNA Engine, programmed as follows: 94° C., 2 min; 40 cycles of 94° C., 30 sec, 66° C., 30 sec, and 68° C., 1 min; followed by 1 cycle at 68° C., 8 min and a holding cycle at 4° C.

30 µl of each amplification product was visualized on a 0.8% agarose gel in 1×TAE buffer (Invitrogen). Products of the expected molecular weight were purified from the gel using the MinElute DNA Purification System (Qiagen), eluted in 10 µl of EB buffer (10 mM Tris.Cl, pH 8.5) and subcloned directly.

Subcloning of PCR Products

The PCR products were subcloned into the topoisomerase I modified cloning vector (pCR4-TOPO) using the TA cloning kit purchased from the Invitrogen Corporation using the conditions specified by the manufacturer. Briefly, 4 µl of gel purified PCR product was incubated for 15 min at room temperature with 1 µl of TOPO vector and 1 µl salt solution. The reaction mixture was then transformed into *E. coli* strain TOP10 (Invitrogen) as follows: a 50 µl aliquot of One Shot TOP10 cells was thawed on ice and 2 µl of TOPO reaction was added. The mixture was incubated for 15 min on ice and then heat shocked by incubation at 42° C. for exactly 30 s. Samples were returned to ice and 250 µl of warm (room temperature) SOC media was added. Samples were incubated with shaking (220 rpm) for 1 h at 37° C. The transformation mixture was then plated on L-broth (LB) plates containing ampicillin (100 µg/ml) and incubated overnight at 37° C.

Colony PCR

Colonies were inoculated into 50 µl sterile water using a sterile toothpick. A 10 µl aliquot of the inoculum was then subjected to PCR in a total reaction volume of 20 µl containing 1×AmpliTaq™ buffer, 200 µM dNTPs, 20 pmoles of T7 primer, 20 pmoles of T3 primer, and 1 unit of AmpliTaq™ (Applied Biosystems) using an MJ Research DNA Engine. The cycling conditions were as follows: 94° C., 2 min; 30 cycles of 94° C., 30 sec, 48° C., 30 sec and 72° C. for 1 min 30 sec. Samples were maintained at 4° C. (holding cycle) before further analysis.

PCR reaction products were analyzed on 1% agarose gels in 1×TAE buffer. Colonies which gave PCR products of approximately the expected molecular weight (929 bp+105 bp due to the multiple cloning site (MCS)) were grown up overnight at 37° C. in 5 ml L-Broth (LB) containing ampicillin (100 µg /ml), with shaking at 220 rpm.

Plasmid DNA Preparation and Sequencing

Miniprep plasmid DNA was prepared from the 5 ml culture using a Biorobot 8000 robotic system (Qiagen) or Wizard Plus SV Minipreps kit (Promega cat. no. 1460) according to the manufacturer's instructions. Plasmid DNA was eluted in 80 µl of sterile water. The DNA concentration was measured using an Eppendorf BO photometer or Spectramax 190 photometer (Molecular Devices). Plasmid DNA (200-500 ng) was subjected to DNA sequencing with the T7 and T3 sequencing primers (Table 2, FIG. 2) using the BigDye Terminator system (Applied Biosystems cat. no. 4390246) according to the manufacturer's instructions. Sequencing reactions were purified using Dye-Ex columns (Qiagen) or Montage SEQ 96 cleanup plates (Millipore cat. no. LSKS09624) then analyzed on an Applied Biosystems 3700 sequencer.

Sequence analysis identified a clone, amplified from a normal kidney cDNA template, which contained the expected INSP163 sequence. The sequence of the cloned cDNA fragment is shown in FIG. 2. The plasmid map of the cloned PCR product is pCR4-TOPO-INSP163.

TABLE 2

INSP163 cloning and sequencing primers

| Primer | Sequence (5'-3') |
|---|---|
| INSP163-CP1 | TGA GCC GCC TCG GGA CGG AGC CAT (SEQ ID NO: 37) |
| INSP163-CP2 | ACG TGC CCA GGA GCA GCC CGG AGA (SEQ ID NO: 38) |
| INSP163-EX1 | GCA GGC TTC <u>GCC ACC</u> ATG CGG CGC TGG GCC TGG GC (SEQ ID NO: 39) |
| INSP163-EX2 | *TG ATG GTG ATG GTG* CGT GCC CAG GAG CAG *CCC GGA* (SEQ ID NO: 40) |
| GCP Forward | G GGG ACA AGT TTG TAC AAA AAA GCA GGC TTC <u>GCC ACC</u> (SEQ ID NO: 41) |
| GCP Reverse | GGG GAC CAC TTT GTA CAA GAA AGC TGG GTT TCA *ATG GTG ATG GTG ATG GTG* (SEQ ID NO: 42) |
| pEAK12F | GCC AGC TTG GCA CTT GAT GT (SEQ ID NO: 43) |
| pEAK12R | GAT GGA GGT GGA CGT GTC AG (SEQ ID NO: 44) |
| 21M13 | TGT AAA ACG ACG GCC AGT (SEQ ID NO: 45) |
| M13REV | CAG GAA ACA GCT ATG ACC (SEQ ID NO: 46) |
| T7 | TAA TAC GAC TCA CTA TAG G (SEQ ID NO: 47) |
| T3 | ATT AAC CCT CAC TAA AGG (SEQ ID NO: 48) |

<u>Underlined</u> sequence = Kozak sequence
Bold = Stop codon
*Italic* sequence = His tag

Example 5

Construction of Mammalian Cell Expression Vectors for INSP163 pCR4-TOPO-INSP163 was used as PCR template to generate pEAK12d and pDEST12.2 expression clones containing the INSP163 ORF sequence with a 3' sequence encoding a 6HIS tag using the Gateway™ cloning methodology (Invitrogen).

Generation of Gateway Compatible INSP163 ORF Fused to an In Frame 6HIS Tag Sequence The first stage of the Gateway cloning process involves a two step PCR reaction which generates the ORF of INSP163 flanked at the 5' end by an attB1 recombination site and Kozak sequence, and flanked at the 3' end by a sequence encoding an in frame 6 histidine (6HIS) tag, a stop codon and the attB2 recombination site (Gateway compatible cDNA). The first PCR reaction (in a final volume of 50 μl) contains respectively: 1 μl (40 ng) of plasmid pCR4-TOPO-INSP163, 1.5 μl dNTPs (10 nM), 10 μl of 10×Pfx polymerase buffer, 1 μl MgSO4 (50 mM), 0.5 μl each of gene specific primer (100 μM) (INSP163-EX1 and INSP163-EX2), 10 μl 10× Enhancer™ solution (vitrogen) and 0.5 μl Platinum Pfx DNA polymerase (Invitrogen). The PCR reaction was performed using an initial denaturing step of 95° C. for 2 min, followed by 12 cycles of 94° C. for 15 s; 55° C. for 30 s and 68° C. for 2 min; and a holding cycle of 4° C. The amplification product was directly purified using the Wizard PCR Preps DNA Purification System (Promega) and recovered in 50 μl sterile water according to the manufacturer's instructions.

The second PCR reaction (in a final volume of 50 μl) contained 10 μl purified PCR1 product, 1.5 μl dNTPs (10 mM), 5 μl of 10×Pfx polymerase buffer, 1 μl MgSO4 (50 mM), 0.5 μl of each Gateway conversion primer (100 μM) (GCP forward and GCP reverse) and 0.5 μl of Platinum Pfx DNA polymerase. The conditions for the 2nd PCR reaction were: 95° C. for 1 min; 4 cycles of 94° c., 15 sec; 50° C., 30 sec and 68° C. for 2 min; 25 cycles of 94° C., 15 sec; 55° C., 30 sec and 68° C., 2 min; followed by a holding cycle of 4° C. PCR product was visualized on 0.8% agarose gel in 1×TAE buffer (Invitrogen) and the band migrating at the predicted molecular mass (976 bp) was purified from the gel using the Wizard PCR Preps DNA Purification System (Promega) and recovered in 50 μl sterile water according to the manufacturer's instructions.

Subcloning of Gateway Compatible INSP163 ORF into Gateway Entry Vector pDONR221 and Expression Vectors pEAK12d and pDEST12.2

The second stage of the Gateway cloning process involves subcloning of the Gateway modified PCR products into the Gateway entry vector pDONR221 (Invitrogen) as follows: 5 μl of purified product from PCR2 were incubated with 1.5 μl pDONR221 vector (0.1 μg/μl), 2 μl BP buffer and 1.5 μl of BP clonase enzyme mix (Invitrogen) in a final volume of 10 μl at RT for 1 h. The reaction was stopped by addition of proteinase K 1 μl (2 μg/μl) and incubated at 37° C. for a further 10 min. An aliquot of this reaction (1 μl) was used to transform E. coli DH10B cells by electroporation as follows: a 25 μl aliquot of DH10B electrocompetent cells (Invitrogen) was thawed on ice and 1 μl of the BP reaction mix was added. The mixture was transferred to a chilled 0.1 cm electroporation cuvette and the cells electroporated using a BioRad Gene-Pulser™ according to the manufacturer's recommended protocol. SOC media (0.5 ml) which had been pre-warmed to room temperature was added immediately after electroporation. The mixture was transferred to a 15 ml snap-cap tube and incubated, with shaking (220 rpm) for 1 h at 37° C. Aliquots of the transformation mixture (10 μl and 50 μl) were then plated on L-broth (LB) plates containing kanamycin (40 μg/ml) and incubated overnight at 37° C.

Plasmid mini-prep DNA was prepared from 5 ml cultures from 6 of the resultant colonies using a Qiaprep BioRobot 8000 system (Qiagen). Plasmid DNA (150-200 ng) was subjected to DNA sequencing with 21M13 and M13Rev primers using the BigDyeTerminator system (Applied Biosystems cat. no. 4336919) according to the manufacturer's instructions. The primer sequences are shown in Table 2. Sequencing reactions were purified using Montage SEQ 96 cleanup plates (Millipore cat. no. LSKS09624) then analyzed on an Applied Biosystems 3700 sequencer.

Plasmid eluate (2 μl or approx. 150 ng) from one of the clones which contained the correct sequence (pENTR_INSP163-6HIS) was then used in a recombination reaction containing 1.5 μl of either pEAK12d vector or pDEST12.2 vector (0.1 μg/μl), 2 μl LR buffer and 1.5 μl of LR clonase (Invitrogen) in a final volume of 10 μl. The mixture was incubated at RT for 1 h, stopped by addition of proteinase K (2 μg) and incubated at 37° C. for a further 10 min. An aliquot of this reaction (1 μl) was used to transform E. coli DH10B cells by electroporation as follows: a 25 μl aliquot of DH10B electrocompetent cells (Invitrogen) was thawed on ice and 1 μl of the LR reaction mix was added. The mixture was transferred to a chilled 0.1 cm electroporation cuvette and the cells electroporated using a BioRad Gene-Pulser™ according to the manufacturer's recommended protocol. SOC media (0.5 ml) which had been pre-warmed to room temperature was added immediately after electroporation. The mixture was transferred to a 15 ml snap-cap tube and incubated, with shaking (220 rpm) for 1 h at 37° C. Aliquots of the transformation mixture (10 μl and 50 μl) were then plated on L-broth (LB) plates containing ampicillin (100 μg/ml) and incubated overnight at 37° C.

Plasmid mini-prep DNA was prepared from 5 ml cultures from 6 of the resultant colonies subcloned in each vector using a Qiaprep BioRobot 8000 system (Qiagen). Plasmid DNA (200-500 ng) in the pEAK12d vector was subjected to DNA sequencing with pEAK12F and pEAK12R primers as described above. Plasmid DNA (200-500 ng) in the pDEST12.2 vector was subjected to DNA sequencing with 21M13 and M13Rev primers as described above. Primer sequences are shown in Table 2.

CsCl gradient purified maxi-prep DNA was prepared from a 500 ml culture of the sequence verified clone (pEAK12d_INSP163-6HIS) using the method described by Sambrook J. et al., 1989 (in Molecular Cloning, a Laboratory Manual, 2$^{nd}$ edition, Cold Spring Harbor Laboratory Press). Plasmid DNA was resuspended at a concentration of 1 μg/μl in sterile water (or 10 nM Tris-HCl pH 8.5) and stored at −20° C.

Endotoxin-free maxi-prep DNA was prepared from a 500 ml culture of the sequence verified clone (pDEST12.2_INSP163-6HIS) using the EndoFree Plasmid Mega kit (Qiagen) according to the manufacturer's instruc-

Example 6

Expression and Purification of INSP163

Further experiments may now be performed to determine the tissue distribution and expression levels of the INSP163 polypeptide in vivo, on the basis of the nucleotide and amino acid sequence disclosed herein.

The presence of the transcripts for INSP163 may be investigated by PCR of cDNA from different human tissues. The INSP163 transcripts may be present at very low levels in the samples tested. Therefore, extreme care is needed in the design of experiments to establish the presence of a transcript in various human tissues as a small amount of genomic contamination in the RNA preparation will provide a false positive result. Thus, all RNA should be treated with DNAse prior to use for reverse transcription. In addition, for each tissue a control reaction may be set up in which reverse transcription was not undertaken (a-ve RT control).

For example, 1 μg of total RNA from each tissue may be used to generate cDNA using Multiscript reverse transcriptase (ABI) and random hexamer primers. For each tissue, a control reaction is set up in which all the constituents are added except the reverse transcriptase (-ve RT control). PCR reactions are set up for each tissue on the reverse transcribed RNA samples and the minus RT controls. INSP163-specific primers may readily be designed on the basis of the sequence information provided herein. The presence of a product of the correct molecular weight in the reverse transcribed sample together with the absence of a product in the minus RT control may be taken as evidence for the presence of a transcript in that tissue. Any suitable cDNA libraries may be used to screen for the INSP163 transcripts, not only those generated as described above.

The tissue distribution pattern of the INSP163 polypeptides will provide further useful information in relation to the function of those polypeptides.

In addition, further experiments may now be performed using expression vectors. Transfection of mammalian cell lines with these vectors may enable the high level expression of the INSP163 proteins and thus enable the continued investigation of the functional characteristics of the INSP163 polypeptides. The following material and methods are an example of those suitable in such experiments:

Cell Culture

Human Embryonic Kidney 293 cells expressing the Epstein-Barr virus Nuclear Antigen (HEK293-EBNA, Invitrogen) are maintained in suspension in Ex-cell VPRO serum-free medium (seed stock, maintenance medium, JRH). Sixteen to 20 hours prior to transfection (Day-1), cells are seeded in 2×T225 flasks (50 ml per flask in DMEM/F12 (1:1) containing 2% FBS seeding medium (JRH) at a density of 2×10$^5$ cells/ml). The next day (transfection day 0) transfection takes place using the JetPEI™ reagent (2 μl/μg of plasmid DNA, PolyPlus-transfection). For each flask, plasmid DNA is co-transfected with GFP (fluorescent reporter gene) DNA. The transfection mix is then added to the 2×T225 flasks and incubated at 37° C. (5% $CO_2$) for 6 days. Confirmation of positive transfection may be carried out by qualitative fluorescence examination at day 1 and day 6 (Axiovert 10 Zeiss).

On day 6 (harvest day), supernatants from the two flasks are pooled and centrifuged (e.g. 4° C., 400 g) and placed into a pot bearing a unique identifier. One aliquot (500 μl) is kept for QC of the 6His-tagged protein (internal bioprocessing QC).

Scale-up batches may be produced by following the protocol called "PEI transfection of suspension cells", referenced BP/PEI/HH/02/04, with PolyEthyleneImine from Polysciences as transfection agent.

Purification Process

The culture medium sample containing the recombinant protein with a C-terminal 6His tag is diluted with cold buffer A (50 mM $NaH_2PO_4$; 600 nM NaCl; 8.7% (w/v) glycerol, pH 7.5). The sample is filtered then through a sterile filter (Millipore) and kept at 4° C. in a sterile square media bottle (Nalgene).

The purification is performed at 4° C. on the VISION workstation (Applied Biosystems) connected to an automatic sample loader (Labomatic). The purification procedure is composed of two sequential steps, metal affinity chromatography on a Poros 20 MC (Applied Biosystems) column charged with Ni ions (4.6×50 mm, 0.83 ml), followed by gel filtration on a Sephadex G-25 medium (Amersham Pharmacia) column (1.0×10 cm).

For the first chromatography step the metal affinity column is regenerated with 30 column volumes of EDTA solution (100 mM EDTA; 1M NaCl; pH 8.0), recharged with Ni ions through washing with 15 column volumes of a 100 mM $NiSO_4$ solution, washed with 10 column volumes of buffer A, followed by 7 column volumes of buffer B (50 mM $NaH_2PO_4$; 600 mM NaCl; 8.7% (w/v) glycerol, 400 mM; imidazole, pH 7.5), and finally equilibrated with 15 column volumes of buffer A containing 15 nM imidazole. The sample is transferred, by the Labomatic sample loader, into a 200 ml sample loop and subsequently charged onto the Ni metal affinity column at a flow rate of 10 ml/min. The column is washed with 12 column volumes of buffer A, followed by 28 column volumes of buffer A containing 20 mM imidazole. During the 20 mM imidazole wash loosely attached contaminating proteins are eluted from the column. The recombinant His-tagged protein is finally eluted with 10 column volumes of buffer B at a flow rate of 2 ml/min, and the eluted protein is collected.

For the second chromatography step, the Sephadex G-25 gel-filtration column is regenerated with 2 ml of buffer D (1.137M NaCl; 2.7 nM KCl; 1.5 nM $KH_2PO_4$; 8 nM $Na_2HPO_4$; pH 7.2), and subsequently equilibrated with 4 column volumes of buffer C (137 nM NaCl; 2.7 nM KCl; 1.5 nM $KH_2PO_4$; 8 mM $Na_2HPO_4$; 20% (w/v) glycerol; pH 7.4). The peak fraction eluted from the Ni-column is automatically loaded onto the Sephadex G-25 column through the integrated sample loader on the VISION and the protein is eluted with buffer C at a flow rate of 2 ml/min. The fraction was filtered through a sterile centrifugation filter (Millipore), frozen and stored at −80° C. An aliquot of the sample is analyzed on SDS-PAGE (4-12% NuPAGE gel; Novex) Western blot with anti-His antibodies. The NuPAGE gel may be stained in a 0.1% Coomassie blue R250 staining solution (30% methanol, 10% acetic acid) at room temperature for 1 h and subsequently destained in 20% methanol, 7.5% acetic acid until the background is clear and the protein bands clearly visible.

Following the electrophoresis the proteins are electrotransferred from the gel to a nitrocellulose membrane. The membrane is blocked with 5% milk powder in buffer E (137 nM NaCl; 2.7 nM KCl; 1.5 nM $KH_2PO_4$; 8 nM $Na_2HPO_4$; 0.1% Tween 20, pH 7.4) for 1 h at room temperature, and subsequently incubated with a mixture of 2 rabbit polyclonal anti-His antibodies (G-18 and H-15, 0.2 μg/ml each; Santa Cruz)

in 2.5% milk powder in buffer E overnight at 4° C. After a further 1 hour incubation at room temperature, the membrane is washed with buffer E (3×10 min), and then incubated with a secondary HRP-conjugated anti-rabbit antibody (DAKO, HRP 0399) diluted 1/3000 in buffer E containing 2.5% milk powder for 2 hours at room temperature. After washing with buffer E (3×10 minutes), the membrane is developed with the ECL kit (Amersham Pharmacia) for 1 min. The membrane is subsequently exposed to a Hyperfilm (Amersham Pharmacia), the film developed and the western blot image visually analysed.

For samples that showed detectable protein bands by Coomassie staining, the protein concentration may be determined using the BCA protein assay kit (Pierce) with bovine serum albumin as standard.

Furthermore, overexpression or knock-down of the expression of the polypeptides in cell lines may be used to determine the effect on transcriptional activation of the host cell genome. Dimerisation partners, co-activators and co-repressors of the INSP163 polypeptide may be identified by immunoprecipitation combined with Western blotting and immunoprecipitation combined with mass spectroscopy.

List of INSP163 specific sequences:

```
SEQ ID NO: 1 (INSP163 alternative mature nucleotide
sequence)
      1 GGGGGCGTCG GGGCCCGGCG GGAGGCACAG AGGACGCAGC AGCCTGGCCA

51 GCGCGCAGAT CCCCCCAACG CCACCGCCAG CGCGTCCTCC CGCGAGGGGC

101 TGCCCGAGGC CCCCAAGCCA TCCCAGGCCT CAGGACCTGA GTTCTCCGAC

151 GCCCACATGA CATGGCTGAA CTTTGTCCGG CGGCCGGACG ACGGCGCCTT

201 AAGGAAGCGG TGCGGAAGCA GGGACAAGAA GCCGCGGGAT CTCTTCGGTC

251 CCCCAGGACC TCCAGGTGCA GAAGTGACCG CGGAGACTCT GCTTCACGAG

301 TTTCAGGAGC TGCTGAAAGA GGCCACGGAG CGCCGGTTCT CAGGGCTTCT

351 GGACCCGCTG CTGCCCCAGG GGGCGGGCCT GCGGCTGGTG GGCGAGGCCT

401 TTCACTGCCG GCTGCAGGGT CCCCGCCGGG TGGACAAGCG GACGCTGGTG

451 GAGCTGCATG GTTTCCAGGC TCCTGCTGCC CAAGGTGCCT TCCTGCGAGG

501 CTCCGGTCTG AGCCTGGCCT CGGGTCGGTT CACGGCCCCC GTGTCCGGCA

551 TCTTCCAGTT CTCTGCCAGT CTGCACGTGG ACCACAGTGA GCTGCAGGGC

601 AAGGCCCGGC TGCGGGCCCG GGACGTGGTG TGTGTTCTCA TCTGTATTGA

651 GTCCCTGTGC CAGCGCCACA CGTGCCTGGA GGCCGTCTCA GGCCTGGAGA

701 GCAACAGCAG GGTCTTCACG CTACAGGTGC AGGGGCTGCT GCAGCTGCAG

751 GCTGGACAGT ACGCTTCTGT GTTTGTGGAC AATGGCTCCG GGGCCGTCCT

801 CACCATCCAG GCGGGCTCCA GCTTCTCCGG GCTGCTCCTG GGCACG

SEQ ID NO: 2 (INSP163 alternative mature polypeptide
sequence)
      1 GGVGARREAQ RTQQPGQRAD PPNATASASS REGLPEAPKP SQASGPEFSD

51 AHMTWLNFVR RPDDGALRKR CGSRDKKPRD LFGPPGPPGA EVTAETLLHE

101 FQELLKEATE RRFSGLLDPL LPQGAGLRLV GEAFHCRLQG PRRVDKRTLV

151 ELHGFQAPAA QGAFLRGSGL SLASGRFTAP VSGIFQFSAS LHVDHSELQG

201 KARLRARDVV CVLICIESLC QRHTCLEAVS GLESNSRVFT LQVQGLLQLQ

251 AGQYASVFVD NGSGAVLTIQ AGSSFSGLLL GT

SEQ ID NO: 3 (INSP163-A nucleotide sequence)
      1 CCGGACGACG GCGCCTTAAG GAAGCGGTGC GGAAGCAGGG ACAAGAAGCC

51 GCGGGATCTC TTCGGTCCCC CAGGACCTCC AGGTGCAGAA GTGACCGCGG

101 AGACTCTGCT TCACGAGTTT CAGGAGCTGC TGAAAGAGGC CACGGAGCGC

151 CGGTTCTCAG GCTTCTGGA CCCGCTGCTG CCCCAGGGGG CGGGCCTGCG

201 GCTGGTGGGC GAGGCCTTTC ACTGCCGGCT GCAGGGTCCC CGCCGGGTGG
```

-continued

```
251 ACAAGCGGAC GCTGGTGGAG CTGCATGGTT TCCAGGCTCC TGCTGCCCAA
301 GGTGCCTTCC TGCGAGGCTC CGGTCTGAGC CTGGCCTCGG GTCGGTTCAC
351 GGCCCCCGTG TCCGGCATCT TCCAGTTCTC TGCCAGTCTG CACGTGGACC
401 ACAGTGAGCT GCAGGGCAAG GCCCGGCTGC GGGCCCGGGA CGTGGTGTGT
451 GTTCTCATCT GTATTGAGTC CCTGTGCCAG CGCCACACGT GCCTGGAGGC
501 CGTCTCAGGC CTGGAGAGCA ACAGCAGGGT CTTCACGCTA CAGGTGCAGG
551 GGCTGCTGCA GCTGCAGGCT GGACAGTACG CTTCTGTGTT TGTGGACAAT
601 GGCTCCGGGG CCGTCCTCAC CATCCAGGCG GGCTCCAGCT TCTCCGGGCT
651 GCTCCTGGGC ACG
```

SEQ ID NO: 4 (INSP163-A polypeptide sequence)
```
  1 PDDGALRKRC GSRDKKPRDL FGPPGPPGAE VTAETLLHEF QELLKEATER
 51 RFSGLLDPLL PQGAGLRLVG EAFHCRLQGP RRVDKRTLVE LHGFQAPAAQ
101 GAFLRGSGLS LASGRFTAPV SGIFQFSASL HVDHSELQGK ARLRARDVVC
151 VLICIESLCQ RHTCLEAVSG LESNSRVFTL QVQGLLQLQA GQYASVFVDN
201 GSGAVLTIQA GSSFSGLLLG T
```

SEQ ID NO: 5 (INSP163-B nucleotide sequence)
```
  1 AAGCGGTGCG GAAGCAGGGA CAAGAAGCCG CGGGATCTCT TCGGTCCCCC
 51 AGGACCTCCA GGTGCAGAAG TGACCGCGGA GACTCTGCTT CACGAGTTTC
101 AGGAGCTGCT GAAAGAGGCC ACGGAGCGCC GGTTCTCAGG GCTTCTGGAC
151 CCGCTGCTGC CCAGGGGGC GGGCCTGCGG CTGGTGGGCG AGGCCTTTCA
201 CTGCCGGCTG CAGGGTCCCC GCCGGGTGGA CAAGCGGACG CTGGTGGAGC
251 TGCATGGTTT CCAGGCTCCT GCTGCCCAAG GTGCCTTCCT GCGAGGCTCC
301 GGTCTGAGCC TGGCCTCGGG TCGGTTCACG GCCCCCGTGT CCGGCATCTT
351 CCAGTTCTCT GCCAGTCTGC ACGTGGACCA CAGTGAGCTG CAGGGCAAGG
401 CCCGGCTGCG GGCCCGGGAC GTGGTGTGTG TTCTCATCTG TATTGAGTCC
451 CTGTGCCAGC GCCACACGTG CCTGGAGGCC GTCTCAGGCC TGGAGAGCAA
501 CAGCAGGGTC TTCACGCTAC AGGTGCAGGG GCTGCTGCAG CTGCAGGCTG
551 GACAGTACGC TTCTGTGTTT GTGGACAATG GCTCCGGGGC CGTCCTCACC
601 ATCCAGGCGG GCTCCAGCTT CTCCGGGCTG CTCCTGGGCA CG
```

SEQ ID NO: 6 (INSP163-B polypeptide sequence)
```
  1 KRCGSRDKKP RDLFGPPGPP GAEVTAETLL HEFQELLKEA TERRFSGLLD
 51 PLLPQGAGLR LVGEAFHCRL QGPRRVDKRT LVELHGFQAP AAQGAFLRGS
101 GLSLASGRFT APVSGIFQFS ASLHVDHSEL QGKARLRARD VVCVLICIES
151 LCQRHTCLEA VSGLESNSRV FTLQVQGLLQ LQAGQYASVF VDNGSGAVLT
201 IQAGSSFSGL LLGT
```

SEQ ID NO: 7 (INSP163-C nucleotide sequence)
```
  1 TGCGGAAGCA GGGACAAGAA GCCGCGGGAT CTCTTCGGTC CCCCAGGACC
 51 TCCAGGTGCA GAAGTGACCG CGGAGACTCT GCTTCACGAG TTTCAGGAGC
101 TGCTGAAAGA GGCCACGGAG CGCCGGTTCT CAGGGCTTCT GGACCCGCTG
151 CTGCCCCAGG GGGCGGGCCT GCGGCTGGTG GGCGAGGCCT TTCACTGCCG
201 GCTGCAGGGT CCCCGCCGGG TGGACAAGCG GACGCTGGTG GAGCTGCATG
```

-continued

```
    251 GTTTCCAGGC TCCTGCTGCC CAAGGTGCCT TCCTGCGAGG CTCCGGTCTG

301 AGCCTGGCCT CGGGTCGGTT CACGGCCCCC GTGTCCGGCA TCTTCCAGTT

351 CTCTGCCAGT CTGCACGTGG ACCACAGTGA GCTGCAGGGC AAGGCCCGGC

401 TGCGGGCCCG GGACGTGGTG TGTGTTCTCA TCTGTATTGA GTCCCTGTGC

451 CAGCGCCACA CGTGCCTGGA GGCCGTCTCA GGCCTGGAGA GCAACAGCAG

501 GGTCTTCACG CTACAGGTGC AGGGGCTGCT GCAGCTGCAG GCTGGACAGT

551 ACGCTTCTGT GTTTGTGGAC AATGGCTCCG GGGCCGTCCT CACCATCCAG

601 GCGGGCTCCA GCTTCTCCGG GCTGCTCCTG GGCACG

SEQ ID NO: 8 (INSP163-C polypeptide sequence)
      1 CGSRDKKPRD LFGPPGPPGA EVTAETLLHE FQELLKEATE RRFSGLLDPL

51 LPQGAGLRLV GEAFHCRLQG PRRVDKRTLV ELHGFQAPAA QGAFLRGSGL

101 SLASGRFTAP VSGIFQFSAS LHVDHSELQG KARLRARDVV CVLICIESLC

151 QRHTCLEAVS GLESNSRVFT LQVQGLLQLQ AGQYASVFVD NGSGAVLTIQ

201 AGSSFSGLLL GT

SEQ ID NO: 9 (INSP163-D nucleotide sequence)
      1 TTCTCAGGGC TTCTGGACCC GCTGCTGCCC CAGGGGGCGG GCCTGCGGCT

51 GGTGGGCGAG GCCTTTCACT GCCGGCTGCA GGGTCCCCGC CGGGTGGACA

101 AGCGGACGCT GGTGGAGCTG CATGGTTTCC AGGCTCCTGC TGCCCAAGGT

151 GCCTTCCTGC GAGGCTCCGG TCTGAGCCTG GCCTCGGGTC GGTTCACGGC

201 CCCCGTGTCC GGCATCTTCC AGTTCTCTGC CAGTCTGCAC GTGGACCACA

251 GTGAGCTGCA GGGCAAGGCC CGGCTGCGGG CCCGGGACGT GGTGTGTGTT

301 CTCATCTGTA TTGAGTCCCT GTGCCAGCGC CACACGTGCC TGGAGGCCGT

351 CTCAGGCCTG GAGAGCAACA GCAGGGTCTT CACGCTACAG GTGCAGGGGC

401 TGCTGCAGCT GCAGGCTGGA CAGTACGCTT CTGTGTTTGT GGACAATGGC

451 TCCGGGGCCG TCCTCACCAT CCAGGCGGGC TCCAGCTTCT CCGGGCTGCT

501 CCTGGGCACG

SEQ ID NO: 10 (INSP163-D polypeptide sequence)
      1 FSGLLDPLLP QGAGLRLVGE AFHCRLQGPR RVDKRTLVEL HGFQAPAAQG

51 AFLRGSGLSL ASGRFTAPVS GIFQFSASLH VDHSELQGKA RLRARDVVCV

101 LICIESLCQR HTCLEAVSGL ESNSRVFTLQ VQGLLQLQAG QYASVFVDNG

151 SGAVLTIQAG SSFSGLLLGT

SEQ ID NO: 11 (INSP163-E nucleotide sequence)
      1 GTGGACAAGC GGACGCTGGT GGAGCTGCAT GGTTTCCAGG CTCCTGCTGC

51 CCAAGGTGCC TTCCTGCGAG GCTCCGGTCT GAGCCTGGCC TCGGGTCGGT

101 TCACGGCCCC CGTGTCCGGC ATCTTCCAGT CTCTGCCAG TCTGCACGTG

151 GACCACAGTG AGCTGCAGGG CAAGGCCCGG CTGCGGGCCC GGGACGTGGT

201 GTGTGTTCTC ATCTGTATTG AGTCCCTGTG CCAGCGCCAC ACGTGCCTGG

251 AGGCCGTCTC AGGCCTGGAG AGCAACAGCA GGGTCTTCAC GCTACAGGTG

301 CAGGGGCTGC TGCAGCTGCA GGCTGGACAG TACGCTTCTG TGTTTGTGGA

351 CAATGGCTCC GGGGCCGTCC TCACCATCCA GGCGGGCTCC AGCTTCTCCG

401 GCTGCTCCT GGGCACG
```

-continued

SEQ ID NO: 12 (INSP163-E polypeptide sequence)
```
  1 VDKRTLVELH GFQAPAAQGA FLRGSGLSLA SGRFTAPVSG IFQFSASLHV

51 DHSELQGKAR LRARDVVCVL ICIESLCQRH TCLEAVSGLE SNSRVFTLQV

101 QGLLQLQAGQ YASVFVDNGS GAVLTIQAGS SFSGLLLGT
```

SEQ ID NO: 13 (INSP163-F nucleotide sequence)
```
  1 ACGCTGGTGG AGCTGCATGG TTTCCAGGCT CCTGCTGCCC AAGGTGCCTT

51 CCTGCGAGGC TCCGGTCTGA GCCTGGCCTC GGGTCGGTTC ACGGCCCCCG

101 TGTCCGGCAT CTTCCAGTTC TCTGCCAGTC TGCACGTGGA CCACAGTGAG

151 CTGCAGGGCA AGGCCCGGCT GCGGGCCCGG ACGTGGTGT GTGTTCTCAT

201 CTGTATTGAG TCCCTGTGCC AGCGCCACAC GTGCCTGGAG GCCGTCTCAG

251 GCCTGGAGAG CAACAGCAGG GTCTTCACGC TACAGGTGCA GGGGCTGCTG

301 CAGCTGCAGG CTGGACAGTA CGCTTCTGTG TTTGTGGACA ATGGCTCCGG

351 GGCCGTCCTC ACCATCCAGG CGGGCTCCAG CTTCTCCGGG CTGCTCCTGG

401 GCACG
```

SEQ ID NO: 14 (INSP163-F polypeptide sequence)
```
  1 TLVELHGFQA PAAQGAFLRG SGLSLASGRF TAPVSGIFQF SASLHVDHSE

51 LQGKARLRAR DVVCVLICIE SLCQRHTCLE AVSGLESNSR VFTLQVQGLL

101 QLQAGQYASV FVDNGSGAVL TIQAGSSFSG LLLGT
```

SEQ ID NO: 15 (histidine tag INSP163 alternative mature
nucleotide sequence)
```
  1 GGGGGCGTCG GGCCCGGCG GGAGGCACAG AGGACGCAGC AGCCTGGCCA

51 GCGCGCAGAT CCCCCCAACG CCACCGCCAG CGCGTCCTCC CGCGAGGGGC

101 TGCCCGAGGC CCCCAAGCCA TCCCAGGCCT CAGGACCTGA GTTCTCCGAC

151 GCCCACATGA CATGGCTGAA CTTTGTCCGG CGGCCGGACG ACGGCGCCTT

201 AAGGAAGCGG TGCGGAAGCA GGGACAAGAA GCCGCGGGAT CTCTTCGGTC

251 CCCCAGGACC TCCAGGTGCA GAAGTGACCG CGGAGACTCT GCTTCACGAG

301 TTTCAGGAGC TGCTGAAAGA GGCCACGGAG CGCCGGTTCT CAGGGCTTCT

351 GGACCCGCTG CTGCCCCAGG GGGCGGGCCT GCGGCTGGTG GGCGAGGCCT

401 TTCACTGCCG GCTGCAGGGT CCCCGCCGGG TGGACAAGCG GACGCTGGTG

451 GAGCTGCATG GTTTCCAGGC TCCTGCTGCC CAAGGTGCCT TCCTGCGAGG

501 CTCCGGTCTG AGCCTGGCCT CGGGTCGGTT CACGGCCCCC GTGTCCGGCA

551 TCTTCCAGTT CTCTGCCAGT CTGCACGTGG ACCACAGTGA GCTGCAGGGC

601 AAGGCCCGGC TGCGGGCCCG GGACGTGGTG TGTGTTCTCA TCTGTATTGA

651 GTCCCTGTGC CAGCGCCACA CGTGCCTGGA GGCCGTCTCA GGCCTGGAGA

701 GCAACAGCAG GGTCTTCACG CTACAGGTGC AGGGGCTGCT GCAGCTGCAG

751 GCTGGACAGT ACGCTTCTGT GTTTGTGGAC AATGGCTCCG GGCCGTCCT

801 CACCATCCAG GCGGGCTCCA GCTTCTCCGG GCTGCTCCTG GCACGCACC

851 ATCACCATCA CCAT
```

SEQ ID NO: 16 (histidine tag INSP163 alternative mature
polypeptide sequence)
```
  1 GGVGARREAQ RTQQPGQRAD PPNATASASS REGLPEAPKP SQASGPEFSD

51 AHMTWLNFVR RPDDGALRKR CGSRDKKPRD LFGPPGPPGA EVTAETLLHE

101 FQELLKEATE RRFSGLLDPL LPQGAGLRLV GEAFHCRLQG PRRVDKRTLV
```

```
151 ELHGFQAPAA QGAFLRGSGL SLASGRFTAP VSGIFQFSAS LHVDHSELQG

201 KARLRARDVV CVLICIESLC QRHTCLEAVS GLESNSRVFT LQVQGLLQLQ

251 AGQYASVFVD NGSGAVLTIQ AGSSFSGLLL GTHHHHHH
```

SEQ ID NO: 17 (histidine tag INSP163-A nucleotide sequence)
```
  1 CCGGACGACG GCGCCTTAAG GAAGCGGTGC GGAAGCAGGG ACAAGAAGCC

51 GCGGGATCTC TTCGGTCCCC AGGACCTCC AGGTGCAGAA GTGACCGCGG

101 AGACTCTGCT TCACGAGTTT CAGGAGCTGC TGAAAGAGGC CACGGAGCGC

151 CGGTTCTCAG GCTTCTGGA CCCGCTGCTG CCCCAGGGGG CGGGCCTGCG

201 GCTGGTGGGC GAGGCCTTTC ACTGCCGGCT GCAGGGTCCC CGCCGGGTGG

251 ACAAGCGGAC GCTGGTGGAG CTGCATGGTT TCCAGGCTCC TGCTGCCCAA

301 GGTGCCTTCC TGCGAGGCTC CGGTCTGAGC CTGGCCTCGG GTCGGTTCAC

351 GGCCCCCGTG TCCGGCATCT TCCAGTTCTC TGCCAGTCTG CACGTGGACC

401 ACAGTGAGCT GCAGGGCAAG GCCCGGCTGC GGGCCCGGGA CGTGGTGTGT

451 GTTCTCATCT GTATTGAGTC CCTGTGCCAG CGCCACACGT GCCTGGAGGC

501 CGTCTCAGGC CTGGAGAGCA ACAGCAGGGT CTTCACGCTA CAGGTGCAGG

551 GGCTGCTGCA GCTGCAGGCT GGACAGTACG CTTCTGTGTT TGTGGACAAT

601 GGCTCCGGGG CCGTCCTCAC CATCCAGGCG GGCTCCAGCT TCTCCGGGCT

651 GCTCCTGGGC ACGCACCATC ACCATCACCA T
```

SEQ ID NO: 18 (histidine tag INSP163-A polypeptide sequence)
```
  1 PDDGALRKRC GSRDKKPRDL FGPPGPPGAE VTAETLLHEF QELLKEATER

51 RFSGLLDPLL PQGAGLRLVG EAFHCRLQGP RRVDKRTLVE LHGFQAPAAQ

101 GAFLRGSGLS LASGRFTAPV SGIFQFSASL HVDHSELQGK ARLRARDVVC

151 VLICIESLCQ RHTCLEAVSG LESNSRVFTL QVQGLLQLQA GQYASVFVDN

201 GSGAVLTIQA GSSFSGLLLG THHHHHH
```

SEQ ID NO: 19 (histidine tag INSP163-B nucleotide sequence)
```
  1 AAGCGGTGCG GAAGCAGGGA CAAGAAGCCG CGGGATCTCT TCGGTCCCCA

51 GGACCTCCA GGTGCAGAAG TGACCGCGGA GACTCTGCTT CACGAGTTTC

101 AGGAGCTGCT GAAAGAGGCC ACGGAGCGCC GGTTCTCAGG CTTCTGGAC

151 CCGCTGCTGC CCAGGGGGC GGGCCTGCGG CTGGTGGGCG AGGCCTTTCA

201 CTGCCGGCTG CAGGGTCCCC GCCGGGTGGA CAAGCGGACG CTGGTGGAGC

251 TGCATGGTTT CCAGGCTCCT GCTGCCCAAG GTGCCTTCCT GCGAGGCTCC

301 GGTCTGAGCC TGGCCTCGGG TCGGTTCACG GCCCCCGTGT CCGGCATCTT

351 CCAGTTCTCT GCCAGTCTGC ACGTGGACCA CAGTGAGCTG CAGGGCAAGG

401 CCCGGCTGCG GGCCCGGGAC GTGGTGTGTG TTCTCATCTG TATTGAGTCC

451 CTGTGCCAGC GCCACACGTG CCTGGAGGCC GTCTCAGGCC TGGAGAGCAA

501 CAGCAGGGTC TTCACGCTAC AGGTGCAGGG GCTGCTGCAG CTGCAGGCTG

551 GACAGTACGC TTCTGTGTTT GTGGACAATG GCTCCGGGGC CGTCCTCACC

601 ATCCAGGCGG CTCCAGCTT CTCCGGGCTG CTCCTGGGCA CGCACCATCA

651 CCATCACCAT
```

SEQ ID NO: 20 (histidine tag INSP163-B polypeptide sequence)
```
  1 KRCGSRDKKP RDLFGPPGPP GAEVTAETLL HEFQELLKEA TERRFSGLLD
```

```
 51 PLLPQGAGLR LVGEAFHCRL QGPRRVDKRT LVELHGFQAP AAQGAFLRGS

101 GLSLASGRFT APVSGIFQFS ASLHVDHSEL QGKARLRARD VVCVLICIES

151 LCQRHTCLEA VSGLESNSRV FTLQVQGLLQ LQAGQYASVF VDNGSGAVLT

201 IQAGSSFSGL LLGTHHHHHH
```

SEQ ID NO: 21 (histidine tag INSP163-C nucleotide sequence)
```
  1 TGCGGAAGCA GGGACAAGAA GCCGCGGGAT CTCTTCGGTC CCCCAGGACC

51 TCCAGGTGCA GAAGTGACCG CGGAGACTCT GCTTCACGAG TTTCAGGAGC

101 TGCTGAAAGA GGCCACGGAG CGCCGGTTCT CAGGGCTTCT GGACCCGCTG

151 CTGCCCCAGG GGGCGGGCCT GCGGCTGGTG GGCGAGGCCT TCACTGCCG

201 GCTGCAGGGT CCCCGCCGGG TGGACAAGCG GACGCTGGTG GAGCTGCATG

251 GTTTCCAGGC TCCTGCTGCC CAAGGTGCCT TCCTGCGAGG CTCCGGTCTG

301 AGCCTGGCCT CGGGTCGGTT CACGGCCCCC GTGTCCGGCA TCTTCCAGTT

351 CTCTGCCAGT CTGCACGTGG ACCACAGTGA GCTGCAGGGC AAGGCCCGGC

401 TGCGGGCCCG GGACGTGGTG TGTGTTCTCA TCTGTATTGA GTCCCTGTGC

451 CAGCGCCACA CGTGCCTGGA GGCCGTCTCA GGCCTGGAGA GCAACAGCAG

501 GGTCTTCACG CTACAGGTGC AGGGGCTGCT GCAGCTGCAG GCTGGACAGT

551 ACGCTTCTGT GTTTGTGGAC AATGGCTCCG GGGCCGTCCT CACCATCCAG

601 GCGGGCTCCA GCTTCTCCGG GCTGCTCCTG GGCACGCACC ATCACCATCA

651 CCAT
```

SEQ ID NO: 22 (histidine tag INSP163-C polypeptide sequence)
```
  1 CGSRDKKPRD LFGPPGPPGA EVTAETLLHE FQELLKEATE RRFSGLLDPL

51 LPQGAGLRLV GEAFHCRLQG PRRVDKRTLV ELHGFQAPAA QGAFLRGSGL

101 SLASGRFTAP VSGIFQFSAS LHVDHSELQG KARLRARDVV CVLICIESLC

151 QRHTCLEAVS GLESNSRVFT LQVQGLLQLQ AGQYASVFVD NGSGAVLTIQ

201 AGSSFSGLLL GTHHHHHH
```

SEQ ID NO: 23 (histidine tag INSP163-D nucleotide sequence)
```
  1 TTCTCAGGGC TTCTGGACCC GCTGCTGCCC CAGGGGGCGG GCCTGCGGCT

51 GGTGGGCGAG GCCTTTCACT GCCGGCTGCA GGGTCCCCGC CGGGTGGACA

101 AGCGGACGCT GGTGGAGCTG CATGGTTTCC AGGCTCCTGC TGCCCAAGGT

151 GCCTTCCTGC GAGGCTCCGG TCTGAGCCTG GCCTCGGGTC GGTTCACGGC

201 CCCCGTGTCC GGCATCTTCC AGTTCTCTGC CAGTCTGCAC GTGGACCACA

251 GTGAGCTGCA GGGCAAGGCC CGGCTGCGGG CCCGGGACGT GGTGTGTGTT

301 CTCATCTGTA TTGAGTCCCT GTGCCAGCGC ACACGTGCC TGGAGGCCGT

351 CTCAGGCCTG GAGAGCAACA GCAGGGTCTT CACGCTACAG GTGCAGGGGC

401 TGCTGCAGCT GCAGGCTGGA CAGTACGCTT CTGTGTTTGT GGACAATGGC

451 TCCGGGGCCG TCCTCACCAT CCAGGCGGGC TCCAGCTTCT CCGGGCTGCT

501 CCTGGGCACG CACCATCACC ATCACCAT
```

SEQ ID NO: 24 (histidine tag INSP163-D polypeptide sequence)
```
  1 FSGLLDPLLP QGAGLRLVGE AFHCRLQGPR RVDKRTLVEL HGFQAPAAQG

51 AFLRGSGLSL ASGRFTAPVS GIFQFSASLH VDHSELQGKA RLRARDVVCV
```

```
101 LICIESLCQR HTCLEAVSGL ESNSRVFTLQ VQGLLQLQAG QYASVFVDNG

151 SGAVLTIQAG SSFSGLLLGT HHHHHH
```

SEQ ID NO: 25 (histidine tag INSP163-E nucleotide sequence)
```
  1 GTGGACAAGC GGACGCTGGT GGAGCTGCAT GGTTTCCAGG CTCCTGCTGC

51 CCAAGGTGCC TTCCTGCGAG GCTCCGGTCT GAGCCTGGCC TCGGGTCGGT

101 TCACGGCCCC CGTGTCCGGC ATCTTCCAGT CTCTGCCAG TCTGCACGTG

151 GACCACAGTG AGCTGCAGGG CAAGGCCCGG CTGCGGGCCC GGGACGTGGT

201 GTGTGTTCTC ATCTGTATTG AGTCCCTGTG CCAGCGCCAC ACGTGCCTGG

251 AGGCCGTCTC AGGCCTGGAG AGCAACAGCA GGGTCTTCAC GCTACAGGTG

301 CAGGGGCTGC TGCAGCTGCA GGCTGGACAG TACGCTTCTG TGTTTGTGGA

351 CAATGGCTCC GGGGCCGTCC TCACCATCCA GGCGGGCTCC AGCTTCTCCG

401 GGCTGCTCCT GGGCACGCAC CATCACCATC ACCAT
```

SEQ ID NO: 26 (histidine tag INSP163-E polypeptide sequence)
```
  1 VDKRTLVELH GFQAPAAQGA FLRGSGLSLA SGRFTAPVSG IFQFSASLHV

51 DHSELQGKAR LRARDVVCVL ICIESLCQRH TCLEAVSGLE SNSRVFTLQV

101 QGLLQLQAGQ YASVFVDNGS GAVLTIQAGS SFSGLLLGTH HHHH
```

SEQ ID NO: 27 (histidine tag INSP163-F nucleotide sequence)
```
  1 ACGCTGGTGG AGCTGCATGG TTTCCAGGCT CCTGCTGCCC AAGGTGCCTT

51 CCTGCGAGGC TCCGGTCTGA GCCTGGCCTC GGGTCGGTTC ACGGCCCCCG

101 TGTCCGGCAT CTTCCAGTTC TCTGCCAGTC TGCACGTGGA CCACAGTGAG

151 CTGCAGGGCA AGGCCCGGCT GCGGGCCCGG GACGTGGTGT GTGTTCTCAT

201 CTGTATTGAG TCCCTGTGCC AGCGCCACAC GTGCCTGGAG GCCGTCTCAG

251 GCCTGGAGAG CAACAGCAGG GTCTTCACGC TACAGGTGCA GGGGCTGCTG

301 CAGCTGCAGG CTGGACAGTA CGCTTCTGTG TTTGTGGACA ATGGCTCCGG

351 GGCCGTCCTC ACCATCCAGG CGGGCTCCAG CTTCTCCGGG CTGCTCCTGG

401 GCACGCACCA TCACCATCAC CAT
```

SEQ ID NO: 28 (histidine tag INSP163-F polypeptide sequence)
```
  1 TLVELHGFQA PAAQGAFLRG SGLSLASGRF TAPVSGIFQF SASLHVDHSE

51 LQGKARLRAR DVVCVLICIE SLCQRHTCLE AVSGLESNSR VFTLQVQGLL

101 QLQAGQYASV FVDNGSGAVL TIQAGSSFSG LLLGTHHHHH H
```

SEQ ID NO: 29 (INSP163 nucleotide sequence)
```
  1 ATGCGGCGCT GGGCCTGGGC CGCGGTCGTG GTCCTCCTCG GCCGCAGCT

51 CGTGCTCCTC GGGGCGTCG GGCCCGGCG GGAGGCACAG AGGACGCAGC

101 AGCCTGGCCA GCGCGCAGAT CCCCCCAACG CCACCGCCAG CGCGTCCTCC

151 CGCGAGGGGC TGCCCGAGGC CCCCAAGCCA TCCCAGGCCT CAGGACCTGA

201 GTTCTCCGAC GCCCACATGA CATGGCTGAA CTTTGTCCGG CGGCCGGACG

251 ACGGCGCCTT AAGGAAGCGG TGCGGAAGCA GGGACAAGAA GCCGCGGGAT

301 CTCTTCGGTC CCCCAGGACC TCCAGGTGCA GAAGTGACCG CGGAGACTCT

351 GCTTCACGAG TTTCAGGAGC TGCTGAAAGA GGCCACGGAG CGCCGGTTCT

401 CAGGGCTTCT GGACCCGCTG CTGCCCCAGG GGCGGGCCT GCGGCTGGTG

451 GGCGAGGCCT TCACTGCCG GCTGCAGGGT CCCCGCCGGG TGGACAAGCG

501 GACGCTGGTG GAGCTGCATG GTTTCCAGGC TCCTGCTGCC CAAGGTGCCT
```

```
551 TCCTGCGAGG CTCCGGTCTG AGCCTGGCCT CGGGTCGGTT CACGGCCCCC

601 GTGTCCGGCA TCTTCCAGTT CTCTGCCAGT CTGCACGTGG ACCACAGTGA

651 GCTGCAGGGC AAGGCCCGGC TGCGGGCCCG GGACGTGGTG TGTGTTCTCA

701 TCTGTATTGA GTCCCTGTGC CAGCGCCACA CGTGCCTGGA GGCCGTCTCA

751 GGCCTGGAGA GCAACAGCAG GGTCTTCACG CTACAGGTGC AGGGGCTGCT

801 GCAGCTGCAG GCTGGACAGT ACGCTTCTGT GTTTGTGGAC AATGGCTCCG

851 GGGCCGTCCT CACCATCCAG GCGGGCTCCA GCTTCTCCGG GCTGCTCCTG

901 GGCACG

SEQ ID NO: 30 (INSP163 polypeptide sequence)
    1 MRRWAWAAVV VLLGPQLVLL GGVGARREAQ RTQQPGQRAD PPNATASASS

51 REGLPEAPKP SQASGPEFSD AHMTWLNFVR RPDDGALRKR CGSRDKKPRD

101 LFGPPGPPGA EVTAETLLHE FQELLKEATE RRFSGLLDPL LPQGAGLRLV

151 GEAFHCRLQG PRRVDKRTLV ELHGFQAPAA QGAFLRGSGL SLASGRFTAP

201 VSGIFQFSAS LHVDHSELQG KARLRARDVV CVLICIESLC QRHTCLEAVS

251 GLESNSRVFT LQVQGLLQLQ AGQYASVFVD NGSGAVLTIQ AGSSFSGLLL

301 GT

SEQ ID NO: 31 (histidine tag INSP163 nucleotide sequence)
    1 ATGCGGCGCT GGGCCTGGGC CGCGGTCGTG GTCCTCCTCG GGCCGCAGCT

51 CGTGCTCCTC GGGGGCGTCG GGGCCCGGCG GGAGGCACAG AGGACGCAGC

101 AGCCTGGCCA GCGCGCAGAT CCCCCCAACG CCACCGCCAG CGCGTCCTCC

151 CGCGAGGGGC TGCCCGAGGC CCCCAAGCCA TCCCAGGCCT CAGGACCTGA

201 GTTCTCCGAC GCCCACATGA CATGGCTGAA CTTTGTCCGG CGGCCGGACG

251 ACGGCGCCTT AAGGAAGCGG TGCGGAAGCA GGGACAAGAA GCCGCGGGAT

301 CTCTTCGGTC CCCCAGGACC TCCAGGTGCA GAAGTGACCG CGGAGACTCT

351 GCTTCACGAG TTTCAGGAGC TGCTGAAAGA GGCCACGGAG CGCCGGTTCT

401 CAGGGCTTCT GGACCCGCTG CTGCCCCAGG GGGCGGGCCT GCGGCTGGTG

451 GGCGAGGCCT TTCACTGCCG GCTGCAGGGT CCCCGCCGGG TGGACAAGCG

501 GACGCTGGTG GAGCTGCATG GTTTCCAGGC TCCTGCTGCC CAAGGTGCCT

551 TCCTGCGAGG CTCCGGTCTG AGCCTGGCCT CGGGTCGGTT CACGGCCCCC

601 GTGTCCGGCA TCTTCCAGTT CTCTGCCAGT CTGCACGTGG ACCACAGTGA

651 GCTGCAGGGC AAGGCCCGGC TGCGGGCCCG GGACGTGGTG TGTGTTCTCA

701 TCTGTATTGA GTCCCTGTGC CAGCGCCACA CGTGCCTGGA GGCCGTCTCA

751 GGCCTGGAGA GCAACAGCAG GGTCTTCACG CTACAGGTGC AGGGGCTGCT

801 GCAGCTGCAG GCTGGACAGT ACGCTTCTGT GTTTGTGGAC AATGGCTCCG

851 GGGCCGTCCT CACCATCCAG GCGGGCTCCA GCTTCTCCGG GCTGCTCCTG

901 GGCACGCACC ATCACCATCA CCAT

SEQ ID NO: 32 (histidine tag INSP163 polypeptide sequence)
    1 MRRWAWAAVV VLLGPQLVLL GGVGARREAQ RTQQPGQRAD PPNATASASS

51 REGLPEAPKP SQASGPEFSD AHMTWLNFVR RPDDGALRKR CGSRDKKPRD

101 LFGPPGPPGA EVTAETLLHE FQELLKEATE RRFSGLLDPL LPQGAGLRLV

151 GEAFHCRLQG PRRVDKRTLV ELHGFQAPAA QGAFLRGSGL SLASGRFTAP
```

```
201 VSGIFQFSAS LHVDHSELQG KARLRARDVV CVLICIESLC QRHTCLEAVS

251 GLESNSRVFT LQVQGLLQLQ AGQYASVFVD NGSGAVLTIQ AGSSFSGLLL

301 GTHHHHHH

SEQ ID NO: 33 (INSP163 mature nucleotide sequence)
    1 CGGCGGGAGG CACAGAGGAC GCAGCAGCCT GGCCAGCGCG CAGATCCCCC

51 CAACGCCACC GCCAGCGCGT CCTCCCGCGA GGGGCTGCCC GAGGCCCCCA

101 AGCCATCCCA GGCCTCAGGA CCTGAGTTCT CCGACGCCCA CATGACATGG

151 CTGAACTTTG TCCGGCGGCC GGACGACGGC GCCTTAAGGA AGCGGTGCGG

201 AAGCAGGGAC AAGAAGCCGC GGGATCTCTT CGGTCCCCCA GGACCTCCAG

251 GTGCAGGAGT GACCGCGGAG ACTCTGCTTC ACGAGTTTCA GGAGCTGCTG

301 AAAGAGGCCA CGGAGCGCCG GTTCTCAGGG CTTCTGGACC CGCTGCTGCC

351 CCAGGGGGCG GGCCTGCGGC TGGTGGGCGA GGCCTTTCAC TGCCGGCTGC

401 AGGGTCCCCG CCGGGTGGAC AAGCGGACGC TGGTGGAGCT GCATGGTTTC

451 CAGGCTCCTG CTGCCCAAGG TGCCTTCCTG CGAGGCTCCG GTCTGAGCCT

501 GGCCTCGGGT CGGTTCACGG CCCCCGTGTC CGGCATCTTC CAGTTCTCTG

551 CCAGTCTGCA CGTGGACCAC AGTGAGCTGC AGGGCAAGGC CCGGCTGCGG

601 GCCCGGGACG TGGTGTGTGT TCTCATCTGT ATTGAGTCCC TGTGCCAGCG

651 CCACACGTGC CTGGAGGCCG TCTCAGGCCT GGAGAGCAAC AGCAGGGTCT

701 TCACGCTACA GGTGCAGGGG CTGCTGCAGC TGCAGGCTGG ACAGTACGCT

751 TCTGTGTTTG TGGACAATGG CTCCGGGGCC GTCCTCACCA TCCAGGCGGG

801 CTCCAGCTTC TCCGGGCTGC TCCTGGGCAC G

SEQ ID NO: 34 (INSP163 mature polypeptide sequence)
    1 RREAQRTQQP GQRADPPNAT ASASSREGLP EAPKPSQASG PEFSDAHMTW

51 LNFVRRPDDG ALRKRCGSRD KKPRDLFGPP GPPGAEVTAE TLLHEFQELL

101 KEATERRFSG LLDPLLPQGA GLRLVGEAFH CRLQGPRRVD KRTLVELHGF

151 QAPAAQGAFL RGSGLSLASG RFTAPVSGIF QFSASLHVDH SELQGKARLR

201 ARDVVCVLIC IESLCQRHTC LEAVSGLESN SRVFTLQVQG LLQLQAGQYA

251 SVFVDNGSGA VLTIQAGSSF SGLLLGT

SEQ ID NO: 35 (histidine tag INSP163 mature nucleotide
sequence)
    1 CGGCGGGAGG CACAGAGGAC GCAGCAGCCT GGCCAGCGCG CAGATCCCCC

51 CAACGCCACC GCCAGCGCGT CCTCCCGCGA GGGGCTGCCC GAGGCCCCCA

101 AGCCATCCCA GGCCTCAGGA CCTGAGTTCT CCGACGCCCA CATGACATGG

151 CTGAACTTTG TCCGGCGGCC GGACGACGGC GCCTTAAGGA AGCGGTGCGG

201 AAGCAGGGAC AAGAAGCCGC GGGATCTCTT CGGTCCCCCA GGACCTCCAG

251 GTGCAGAAGT GACCGCGGAG ACTCTGCTTC ACGAGTTTCA GGAGCTGCTG

301 AAAGAGGCCA CGGAGCGCCG GTTCTCAGGG CTTCTGGACC CGCTGCTGCC

351 CCAGGGGGCG GGCCTGCGGC TGGTGGGCGA GGCCTTTCAC TGCCGGCTGC

401 AGGGTCCCCG CCGGGTGGAC AAGCGGACGC TGGTGGAGCT GCATGGTTTC

451 CAGGCTCCTG CTGCCCAAGG TGCCTTCCTG CGAGGCTCCG GTCTGAGCCT
```

```
501 GGCCTCGGGT CGGTTCACGG CCCCCGTGTC CGGCATCTTC CAGTTCTCTG

551 CCAGTCTGCA CGTGGACCAC AGTGAGCTGC AGGGCAAGGC CCGGCTGCGG

601 GCCCGGGACG TGGTGTGTGT TCTCATCTGT ATTGAGTCCC TGTGCCAGCG

651 CCACACGTGC CTGGAGGCCG TCTCAGGCCT GGAGAGCAAC AGCAGGGTCT

701 TCACGCTACA GGTGCAGGGG CTGCTGCAGC TGCAGGCTGG ACAGTACGCT

751 TCTGTGTTTG TGGACAATGG CTCCGGGGCC GTCCTCACCA TCCAGGCGGG

801 CTCCAGCTTC TCCGGGCTGC TCCTGGGCAC GCACCATCAC CATCACCAT
```

SEQ ID NO: 36 (histidine tag INSP163 mature polypeptide sequence)
```
  1 RREAQRTQQP GQRADPPNAT ASASSREGLP EAPKPSQASG PEFSDAHMTW

51 LNFVRRPDDG ALRKRCGSRD KKPRDLFGPP GPPGAEVTAE TLLHEFQELL

101 KEATERRFSG LLDPLLPQGA GLRLVGEAFH CRLQGPRRVD KRTLVELHGF

151 QAPAAQGAFL RGSGLSLASG RFTAPVSGIF QFSASLHVDH SELQGKARLR

201 ARDVVCVLIC IESLCQRHTC LEAVSGLESN SRVFTLQVQG LLQLQAGQYA

251 SVFVDNGSGA VLTIQAGSSF SGLLLGTHHH HHH
```

We claim:

1. An isolated polypeptide comprising:
   a) SEQ ID NO:34; or
   b) a fusion protein comprising SEQ ID NO: 34 and a heterologous sequence.

2. The isolated polypeptide according to claim 1, wherein said polypeptide comprises SEQ ID NO: 34.

3. The isolated polypeptide according to claim 1, wherein said polypeptide comprises a fusion protein comprising SEQ ID NO: 34 and a heterologous sequence.

4. The isolated polypeptide according to claim 3, wherein said fusion protein comprises SEQ ID NO: 34 and said heterologous sequence comprises an extracellular domain of a membrane-bound protein, an immunoglobulin constant region, a multimerization domain, a signal sequence or a histidine tag.

5. The isolated polypeptide according to claim 4, wherein said heterologous sequence comprises an extracellular domain of a membrane-bound protein.

6. The isolated polypeptide according to claim 4, wherein said heterologous sequence comprises an immunoglobulin constant region.

7. The isolated polypeptide according to claim 4, wherein said heterologous sequence comprises a multimerization domain.

8. The isolated polypeptide according to claim 4, wherein said heterologous sequence comprises a signal sequence.

9. The isolated polypeptide according to claim 4, wherein said heterologous sequence comprises a histidine tag.

10. A composition comprising a pharmaceutically acceptable excipient and a polypeptide comprising:
    a) SEQ ID NO:34; or
    b) a fusion protein comprising SEQ ID NO: 34 and a heterologous sequence.

11. The composition according to claim 10, wherein said polypeptide comprises SEQ ID NO: 34.

12. The composition according to claim 10, wherein said polypeptide comprises a fusion protein comprising SEQ ID NO: 34 and a heterologous sequence.

13. The composition according to claim 10, wherein said fusion protein comprises SEQ ID NO: 34 and said heterologous sequence comprises an extracellular domain of a membrane-bound protein, an immunoglobulin constant region, a multimerization domain, a signal sequence or a histidine tag.

14. The composition according to claim 13, wherein said heterologous sequence comprises an extracellular domain of a membrane-bound protein.

15. The composition according to claim 13, wherein said heterologous sequence comprises an immunoglobulin constant region.

16. The composition according to claim 13, wherein said heterologous sequence comprises a multimerization domain.

17. The composition according to claim 13, wherein said heterologous sequence comprises a signal sequence.

18. The composition according to claim 13, wherein said heterologous sequence comprises a histidine tag.

* * * * *

UNITED STATES PATENT AND TRADEMARK OFFICE
CERTIFICATE OF CORRECTION

PATENT NO. : 7,700,724 B2
APPLICATION NO. : 10/573936
DATED : April 20, 2010
INVENTOR(S) : Stephen Noel Fitzgerald et al.

It is certified that error appears in the above-identified patent and that said Letters Patent is hereby corrected as shown below:

Column 2,
Line 32, "MRNA" should read --mRNA--.

Column 5,
Line 47, "β-amayloid" should read --β-amyloid--.

Column 10,
Lines 4-5, "osteoarritis" should read --osteoarthritis--.

Column 13,
Line 36, "comeal dystrophy" should read --corneal dystrophy--.
Line 43, "diffuise large cell" should read --diffuse large cell--.
Line 50, "athritis" should read --arthritis--.

Column 18,
Line 17, "used herin" should read --used herein--.

Column 19,
Line 43, "singie" should read --single--.

Column 20,
Line 46, "Jones et aL," should read --Jones et al.,--.
Line 48, "Queen et aL," should read --Queen et al.,--.

Column 21,
Line 31, "MRNA" should read --mRNA--.
Line 32, "CDNA" should read --cDNA--.

Column 22,
Line 11, "MRNA" should read --mRNA--.

Signed and Sealed this

Fifth Day of October, 2010

David J. Kappos
*Director of the United States Patent and Trademark Office*

CERTIFICATE OF CORRECTION (continued)
U.S. Pat. No. 7,700,724 B2

Column 23,
Line 33, "15 nM" should read --15mM--.

Column 25,
Line 34, "Johns Hopldns" should read --Johns Hopkins--.

Column 26,
Line 2, "MRNA" should read --mRNA--.

Column 29,
Line 29, "MRNA" should read --mRNA--.

Column 32,
Line 34, "MRNA" should read --mRNA--.

Column 44,
Line 22, "or SuperScript II" should read --or SuperScript III--.
Line 46, "4 μl 25 nM" should read --4 μl 25 mM--.

Column 45,
Line 17, "2 nM" should read --2mM--.

Column 48,
Line 62, "(or 10 nM" should read --(or 10mM--.

Column 50,
Line 11, "600 nM" should read --600mM--.
Line 32, "15 nM" should read --15mM--.
Line 45, "2.7 nM KCl; 1.5 nM KH$_2$PO$_4$; 8 nM" should read
      --2.7mM KCl; 1.5mM KH$_2$PO$_4$; 8mM--.
Lines 47-48, "137 nM NaCl; 2.7 nM KCl; 1.5 nM" should read
      --137mM NaCl; 2.7mM KCl; 1.5mM--.
Lines 63-64, "137 nM NaCl; 2.7 nM KCl; 1.5 nM KH$_2$PO$_4$; 8 nM" should read
      --137mM NaCl; 2.7mM KCl; 1.5mM KH$_2$PO$_4$; 8mM--.

SEQUENCE LISTING

<160> NUMBER OF SEQ ID NOS: 49

<210> SEQ ID NO 1
<211> LENGTH: 846
<212> TYPE: DNA
<213> ORGANISM: Homo sapiens

<400> SEQUENCE: 1

```
gggggcgtcg gggcccggcg ggaggcacag aggacgcagc agcctggcca gcgcgcagat     60 cccccaacg ccaccgccag cgcgtcctcc cgcgaggggc tgcccgaggc ccccaagcca    120
tcccaggcct caggacctga gttctccgac gcccacatga catggctgaa ctttgtccgg    180
cggccggacg acggcgcctt aaggaagcgg tgcggaagca gggacaagaa gccgcgggat    240
ctcttcggtc ccccaggacc tccaggtgca gaagtgaccg cggagactct gcttcacgag    300
tttcaggagc tgctgaaaga ggccacggag cgccggttct cagggcttct ggacccgctg    360
ctgccccagg gggcgggcct gcggctggtg ggcgaggcct ttcactgccg gctgcagggt    420
ccccgccggg tggacaagcg gacgctgtg gagctgcatg gtttccaggc tcctgctgcc    480
caaggtgcct tcctgcgagg ctccggtctg agcctggcct cgggtcggtt cacggccccc    540
gtgtccggca tcttccagtt ctctgccagt ctgcacgtgg accacagtga gctgcagggc    600
aaggcccggc tgcgggcccg ggacgtggtg tgtgttctca tctgtattga gtccctgtgc    660
cagcgccaca cgtgcctgga ggccgtctca ggcctggaga gcaacagcag ggtcttcacg    720
ctacaggtgc aggggctgct gcagctgcag gctggacagt acgcttctgt gtttgtggac    780
aatggctccg gggccgtcct caccatccag gcgggctcca gcttctccgg gctgctcctg    840
ggcacg                                                              846
```

<210> SEQ ID NO 2
<211> LENGTH: 282

<212> TYPE: PRT
<213> ORGANISM: Homo sapiens

<400> SEQUENCE: 2

```
Gly Gly Val Gly Ala Arg Arg Glu Ala Gln Arg Thr Gln Gln Pro Gly
1               5                   10                  15

Gln Arg Ala Asp Pro Pro Asn Ala Thr Ala Ser Ala Ser Ser Arg Glu
            20                  25                  30

Gly Leu Pro Glu Ala Pro Lys Pro Ser Gln Ala Ser Gly Pro Glu Phe
        35                  40                  45

Ser Asp Ala His Met Thr Trp Leu Asn Phe Val Arg Arg Pro Asp Asp
50                  55                  60

Gly Ala Leu Arg Lys Arg Cys Gly Ser Arg Asp Lys Lys Pro Arg Asp
65                  70                  75                  80

Leu Phe Gly Pro Pro Gly Pro Pro Gly Ala Glu Val Thr Ala Glu Thr
                85                  90                  95

Leu Leu His Glu Phe Gln Glu Leu Leu Lys Glu Ala Thr Glu Arg Arg
            100                 105                 110

Phe Ser Gly Leu Leu Asp Pro Leu Pro Gln Gly Ala Gly Leu Arg
        115                 120                 125

Leu Val Gly Glu Ala Phe His Cys Arg Leu Gln Gly Pro Arg Arg Val
130                 135                 140

Asp Lys Arg Thr Leu Val Glu Leu His Gly Phe Gln Ala Pro Ala Ala
145                 150                 155                 160

Gln Gly Ala Phe Leu Arg Gly Ser Gly Leu Ser Leu Ala Ser Gly Arg
                165                 170                 175

Phe Thr Ala Pro Val Ser Gly Ile Phe Gln Phe Ser Ala Ser Leu His
            180                 185                 190

Val Asp His Ser Glu Leu Gln Gly Lys Ala Arg Leu Arg Ala Arg Asp
        195                 200                 205

Val Val Cys Val Leu Ile Cys Ile Glu Ser Leu Cys Gln Arg His Thr
210                 215                 220

Cys Leu Glu Ala Val Ser Gly Leu Glu Ser Asn Ser Arg Val Phe Thr
225                 230                 235                 240

Leu Gln Val Gln Gly Leu Leu Gln Leu Gln Ala Gly Gln Tyr Ala Ser
                245                 250                 255

Val Phe Val Asp Asn Gly Ser Gly Ala Val Leu Thr Ile Gln Ala Gly
            260                 265                 270

Ser Ser Phe Ser Gly Leu Leu Leu Gly Thr
        275                 280
```

<210> SEQ ID NO 3
<211> LENGTH: 663
<212> TYPE: DNA
<213> ORGANISM: Homo sapiens

<400> SEQUENCE: 3

```
ccggacgacg gcgccttaag gaagcggtgc ggaagcaggg acaagaagcc gcgggatctc      60
ttcggtcccc caggacctcc aggtgcagaa gtgaccgcgg agactctgct tcacgagttt     120
caggagctgc tgaaagaggc cacggagcgc cggttctcag gcttctggga cccgctgctg     180
ccccaggggg cgggcctgcg gctggtgggc gaggcctttc actgccggct gcagggtccc     240
cgccgggtgg acaagcggac gctggtggag ctgcatggtt tccaggctcc tgctgcccaa     300
ggtgccttcc tgcgaggctc cggtctgagc ctggcctcgg gtcggttcac ggcccccgtg     360
```

-continued

```
tccggcatct tccagttctc tgccagtctg cacgtggacc acagtgagct gcagggcaag    420
gcccggctgc gggcccggga cgtggtgtgt gttctcatct gtattgagtc cctgtgccag    480
cgccacacgt gcctggaggc cgtctcaggc ctggagagca acagcagggt cttcacgcta    540
caggtgcagg ggctgctgca gctgcaggct ggacagtacg cttctgtgtt tgtggacaat    600
ggctccgggg ccgtcctcac catccaggcg ggctccagct ctccgggct gctcctgggc     660 acg                                                                  663
```

<210> SEQ ID NO 4
<211> LENGTH: 221
<212> TYPE: PRT
<213> ORGANISM: Homo sapiens

<400> SEQUENCE: 4

Pro Asp Asp Gly Ala Leu Arg Lys Arg Cys Gly Ser Arg Asp Lys Lys
1               5                   10                  15

Pro Arg Asp Leu Phe Gly Pro Gly Pro Gly Ala Glu Val Thr
                20                  25                  30

Ala Glu Thr Leu Leu His Glu Phe Gln Glu Leu Leu Lys Glu Ala Thr
            35                  40                  45

Glu Arg Arg Phe Ser Gly Leu Leu Asp Pro Leu Leu Pro Gln Gly Ala
        50                  55                  60

Gly Leu Arg Leu Val Gly Glu Ala Phe His Cys Arg Leu Gln Gly Pro
65                  70                  75                  80

Arg Arg Val Asp Lys Arg Thr Leu Val Glu Leu His Gly Phe Gln Ala
                85                  90                  95

Pro Ala Ala Gln Gly Ala Phe Leu Arg Gly Ser Gly Leu Ser Leu Ala
            100                 105                 110

Ser Gly Arg Phe Thr Ala Pro Val Ser Gly Ile Phe Gln Phe Ser Ala
        115                 120                 125

Ser Leu His Val Asp His Ser Glu Leu Gln Gly Lys Ala Arg Leu Arg
130                 135                 140

Ala Arg Asp Val Val Cys Val Leu Ile Cys Ile Glu Ser Leu Cys Gln
145                 150                 155                 160

Arg His Thr Cys Leu Glu Ala Val Ser Gly Leu Glu Ser Asn Ser Arg
                165                 170                 175

Val Phe Thr Leu Gln Val Gln Gly Leu Leu Gln Leu Ala Gly Gln
            180                 185                 190

Tyr Ala Ser Val Phe Val Asp Asn Gly Ser Gly Ala Val Leu Thr Ile
        195                 200                 205

Gln Ala Gly Ser Ser Phe Ser Gly Leu Leu Leu Gly Thr
    210                 215                 220

<210> SEQ ID NO 5
<211> LENGTH: 642
<212> TYPE: DNA
<213> ORGANISM: Homo sapiens

<400> SEQUENCE: 5

```
aagcggtgcg gaagcaggga caagaagccg cgggatctct tcggtccccc aggacctcca    60
ggtgcagaag tgaccgcgga gactctgctt cacgagtttc aggagctgct gaaagaggcc   120
acggagcgcc ggttctcagg gcttctggac ccgctgctgc cccagggggc gggcctgcgg   180
ctggtgggcg aggcctttca ctgccggctg caggtccccc gccgggtgga caagcggacg   240
ctggtggagc tgcatggttt ccaggctcct gctgcccaag gtgccttcct gcgaggctcc   300
```

```
ggtctgagcc tggcctcggg tcggttcacg gcccccgtgt ccggcatctt ccagttctct    360
gccagtctgc acgtggacca cagtgagctg cagggcaagg cccggctgcg ggcccgggac    420
gtggtgtgtg ttctcatctg tattgagtcc ctgtgccagc gccacacgtg cctggaggcc    480
gtctcaggcc tggagagcaa cagcagggtc ttcacgctac aggtgcaggg gctgctgcag    540
ctgcaggctg gacagtacgc ttctgtgttt gtggacaatg gctccggggc cgtcctcacc    600
atccaggcgg gctccagctt ctccgggctg ctcctgggca cg                       642
```

```
<210> SEQ ID NO 6
<211> LENGTH: 214
<212> TYPE: PRT
<213> ORGANISM: Homo sapiens

<400> SEQUENCE: 6
```

| Lys | Arg | Cys | Gly | Ser | Arg | Asp | Lys | Lys | Pro | Arg | Asp | Leu | Phe | Gly | Pro |
|---|---|---|---|---|---|---|---|---|---|---|---|---|---|---|---|
| 1 | | | | 5 | | | | | 10 | | | | | 15 | |

| Pro | Gly | Pro | Pro | Gly | Ala | Glu | Val | Thr | Ala | Glu | Thr | Leu | Leu | His | Glu |
|---|---|---|---|---|---|---|---|---|---|---|---|---|---|---|---|
| | | | 20 | | | | | 25 | | | | | 30 | | |

| Phe | Gln | Glu | Leu | Leu | Lys | Glu | Ala | Thr | Glu | Arg | Arg | Phe | Ser | Gly | Leu |
|---|---|---|---|---|---|---|---|---|---|---|---|---|---|---|---|
| | | | 35 | | | | | 40 | | | | | 45 | | |

| Leu | Asp | Pro | Leu | Leu | Pro | Gln | Gly | Ala | Gly | Leu | Arg | Leu | Val | Gly | Glu |
|---|---|---|---|---|---|---|---|---|---|---|---|---|---|---|---|
| | 50 | | | | | 55 | | | | | 60 | | | | |

| Ala | Phe | His | Cys | Arg | Leu | Gln | Gly | Pro | Arg | Arg | Val | Asp | Lys | Arg | Thr |
|---|---|---|---|---|---|---|---|---|---|---|---|---|---|---|---|
| 65 | | | | | 70 | | | | | 75 | | | | | 80 |

| Leu | Val | Glu | Leu | His | Gly | Phe | Gln | Ala | Pro | Ala | Ala | Gln | Gly | Ala | Phe |
|---|---|---|---|---|---|---|---|---|---|---|---|---|---|---|---|
| | | | | 85 | | | | | 90 | | | | | 95 | |

| Leu | Arg | Gly | Ser | Gly | Leu | Ser | Leu | Ala | Ser | Gly | Arg | Phe | Thr | Ala | Pro |
|---|---|---|---|---|---|---|---|---|---|---|---|---|---|---|---|
| | | | 100 | | | | | 105 | | | | | 110 | | |

| Val | Ser | Gly | Ile | Phe | Gln | Phe | Ser | Ala | Ser | Leu | His | Val | Asp | His | Ser |
|---|---|---|---|---|---|---|---|---|---|---|---|---|---|---|---|
| | | | 115 | | | | | 120 | | | | | 125 | | |

| Glu | Leu | Gln | Gly | Lys | Ala | Arg | Leu | Arg | Ala | Arg | Asp | Val | Val | Cys | Val |
|---|---|---|---|---|---|---|---|---|---|---|---|---|---|---|---|
| | 130 | | | | | 135 | | | | | 140 | | | | |

| Leu | Ile | Cys | Ile | Glu | Ser | Leu | Cys | Gln | Arg | His | Thr | Cys | Leu | Glu | Ala |
|---|---|---|---|---|---|---|---|---|---|---|---|---|---|---|---|
| 145 | | | | | 150 | | | | | 155 | | | | | 160 |

| Val | Ser | Gly | Leu | Glu | Ser | Asn | Ser | Arg | Val | Phe | Thr | Leu | Gln | Val | Gln |
|---|---|---|---|---|---|---|---|---|---|---|---|---|---|---|---|
| | | | | 165 | | | | | 170 | | | | | 175 | |

| Gly | Leu | Leu | Gln | Leu | Gln | Ala | Gly | Gln | Tyr | Ala | Ser | Val | Phe | Val | Asp |
|---|---|---|---|---|---|---|---|---|---|---|---|---|---|---|---|
| | | | 180 | | | | | 185 | | | | | 190 | | |

| Asn | Gly | Ser | Gly | Ala | Val | Leu | Thr | Ile | Gln | Ala | Gly | Ser | Ser | Phe | Ser |
|---|---|---|---|---|---|---|---|---|---|---|---|---|---|---|---|
| | | | 195 | | | | | 200 | | | | | 205 | | |

| Gly | Leu | Leu | Leu | Gly | Thr |
|---|---|---|---|---|---|
| | | | 210 | | |

```
<210> SEQ ID NO 7
<211> LENGTH: 636
<212> TYPE: DNA
<213> ORGANISM: Homo sapiens

<400> SEQUENCE: 7
```

```
tgcggaagca gggacaagaa gccgcgggat ctcttcggtc ccccaggacc tccaggtgca     60
gaagtgaccg cggagactct gcttcacgag tttcaggagc tgctgaaaga ggccacggag    120
cgccggttct cagggcttct ggacccgctg ctgccccagg ggcgggcct gcggctggtg     180 ggcgaggcct tcactgcccg gctgcagggt ccccgccggg tggacaagcg gacgctggtg    240
```

```
gagctgcatg gtttccaggc tcctgctgcc caaggtgcct tcctgcgagg ctccggtctg      300
agcctggcct cgggtcggtt cacggccccc gtgtccggca tcttccagtt ctctgccagt      360
ctgcacgtgg accacagtga gctgcagggc aaggcccggc tgcgggcccg ggacgtggtg      420
tgtgttctca tctgtattga gtccctgtgc cagcgccaca cgtgcctgga ggccgtctca      480
ggcctggaga gcaacagcag ggtcttcacg ctacaggtgc aggggctgct gcagctgcag      540
gctggacagt acgcttctgt gtttgtggac aatggctccg gggccgtcct caccatccag      600
gcgggctcca gcttctccgg gctgctcctg ggcacg                               636
```

```
<210> SEQ ID NO 8
<211> LENGTH: 212
<212> TYPE: PRT
<213> ORGANISM: Homo sapiens

<400> SEQUENCE: 8

Cys Gly Ser Arg Asp Lys Lys Pro Arg Asp Leu Phe Gly Pro Pro Gly
  1               5                  10                  15

Pro Pro Gly Ala Glu Val Thr Ala Glu Thr Leu Leu His Glu Phe Gln
             20                  25                  30

Glu Leu Leu Lys Glu Ala Thr Glu Arg Arg Phe Ser Gly Leu Leu Asp
         35                  40                  45

Pro Leu Leu Pro Gln Gly Ala Gly Leu Arg Leu Val Gly Glu Ala Phe
     50                  55                  60

His Cys Arg Leu Gln Gly Pro Arg Arg Val Asp Lys Arg Thr Leu Val
 65                  70                  75                  80

Glu Leu His Gly Phe Gln Ala Pro Ala Ala Gln Gly Ala Phe Leu Arg
                 85                  90                  95

Gly Ser Gly Leu Ser Leu Ala Ser Gly Arg Phe Thr Ala Pro Val Ser
            100                 105                 110

Gly Ile Phe Gln Phe Ser Ala Ser Leu His Val Asp His Ser Glu Leu
        115                 120                 125

Gln Gly Lys Ala Arg Leu Arg Ala Arg Asp Val Val Cys Val Leu Ile
    130                 135                 140

Cys Ile Glu Ser Leu Cys Gln Arg His Thr Cys Leu Glu Ala Val Ser
145                 150                 155                 160

Gly Leu Glu Ser Asn Ser Arg Val Phe Thr Leu Gln Val Gln Gly Leu
                165                 170                 175

Leu Gln Leu Gln Ala Gly Gln Tyr Ala Ser Val Phe Val Asp Asn Gly
            180                 185                 190

Ser Gly Ala Val Leu Thr Ile Gln Ala Gly Ser Ser Phe Ser Gly Leu
        195                 200                 205

Leu Leu Gly Thr
    210

<210> SEQ ID NO 9
<211> LENGTH: 510
<212> TYPE: DNA
<213> ORGANISM: Homo sapiens

<400> SEQUENCE: 9
ttctcagggc ttctggaccc gctgctgccc caggggcgg gcctgcggct ggtgggcgag       60
gcctttcact gccggctgca gggtccccgc cgggtggaca agcggacgct ggtggagctg     120
catggtttcc aggctcctgc tgcccaaggt gccttcctgc gaggctccgg tctgagcctg     180
gcctcgggtc ggttcacggc cccgtgtcc ggcatcttcc agttctctgc cagtctgcac     240
```

```
gtggaccaca gtgagctgca gggcaaggcc cggctgcggg cccgggacgt ggtgtgtgtt    300
ctcatctgta ttgagtccct gtgccagcgc cacacgtgcc tggaggccgt ctcaggcctg    360
gagagcaaca gcagggtctt cacgctacag gtgcaggggc tgctgcagct gcaggctgga    420
cagtacgctt ctgtgtttgt ggacaatggc tccggggccg tcctcaccat ccaggcgggc    480
tccagcttct ccgggctgct cctgggcacg                                     510
```

<210> SEQ ID NO 10
<211> LENGTH: 170
<212> TYPE: PRT
<213> ORGANISM: Homo sapiens

<400> SEQUENCE: 10

Phe Ser Gly Leu Leu Asp Pro Leu Pro Gln Gly Ala Gly Leu Arg
1               5                   10                  15

Leu Val Gly Glu Ala Phe His Cys Arg Leu Gln Gly Pro Arg Arg Val
            20                  25                  30

Asp Lys Arg Thr Leu Val Glu Leu His Gly Phe Gln Ala Pro Ala Ala
        35                  40                  45

Gln Gly Ala Phe Leu Arg Gly Ser Gly Leu Ser Leu Ala Ser Gly Arg
    50                  55                  60

Phe Thr Ala Pro Val Ser Gly Ile Phe Gln Phe Ser Ala Ser Leu His
65                  70                  75                  80

Val Asp His Ser Glu Leu Gln Gly Lys Ala Arg Leu Arg Ala Arg Asp
                85                  90                  95

Val Val Cys Val Leu Ile Cys Ile Glu Ser Leu Cys Gln Arg His Thr
            100                 105                 110

Cys Leu Glu Ala Val Ser Gly Leu Glu Ser Asn Ser Arg Val Phe Thr
        115                 120                 125

Leu Gln Val Gln Gly Leu Leu Gln Leu Gln Ala Gly Gln Tyr Ala Ser
    130                 135                 140

Val Phe Val Asp Asn Gly Ser Gly Ala Val Leu Thr Ile Gln Ala Gly
145                 150                 155                 160

Ser Ser Phe Ser Gly Leu Leu Leu Gly Thr
                165                 170

<210> SEQ ID NO 11
<211> LENGTH: 417
<212> TYPE: DNA
<213> ORGANISM: Homo sapiens

<400> SEQUENCE: 11

```
gtggacaagc ggacgctggt ggagctgcat ggtttccagg ctcctgctgc ccaaggtgcc     60
ttcctgcgag gctccggtct gagcctggcc tcgggtcggt tcacggcccc cgtgtccggc    120
atcttccagt tctctgccag tctgcacgtg gaccacagtg agctgcaggg caaggcccgg    180
ctgcgggccc gggacgtggt gtgtgttctc atctgtattg agtccctgtg ccagcgccac    240
acgtgcctgg aggccgtctc aggcctggag agcaacagca gggtcttcac gctacaggtg    300
caggggctgc tgcagctgca ggctggacag tacgcttctg tgtttgtgga caatggctcc    360
ggggccgtcc tcaccatcca ggcgggctcc agcttctccg gctgctcct gggcacg        417
```

<210> SEQ ID NO 12
<211> LENGTH: 139
<212> TYPE: PRT
<213> ORGANISM: Homo sapiens

<400> SEQUENCE: 12

Val Asp Lys Arg Thr Leu Val Glu Leu His Gly Phe Gln Ala Pro Ala
1               5                   10                  15

Ala Gln Gly Ala Phe Leu Arg Gly Ser Gly Leu Ser Leu Ala Ser Gly
            20                  25                  30

Arg Phe Thr Ala Pro Val Ser Gly Ile Phe Gln Phe Ser Ala Ser Leu
        35                  40                  45

His Val Asp His Ser Glu Leu Gln Gly Lys Ala Arg Leu Arg Ala Arg
    50                  55                  60

Asp Val Val Cys Val Leu Ile Cys Ile Glu Ser Leu Cys Gln Arg His
65                  70                  75                  80

Thr Cys Leu Glu Ala Val Ser Gly Leu Glu Ser Asn Ser Arg Val Phe
                85                  90                  95

Thr Leu Gln Val Gln Gly Leu Leu Gln Leu Gln Ala Gly Gln Tyr Ala
            100                 105                 110

Ser Val Phe Val Asp Asn Gly Ser Gly Ala Val Leu Thr Ile Gln Ala
        115                 120                 125

Gly Ser Ser Phe Ser Gly Leu Leu Leu Gly Thr
    130                 135

<210> SEQ ID NO 13
<211> LENGTH: 405
<212> TYPE: DNA
<213> ORGANISM: Homo sapiens

<400> SEQUENCE: 13
acgctggtgg agctgcatgg tttccaggct cctgctgccc aaggtgcctt cctgcgaggc     60
tccggtctga gcctggcctc gggtcggttc acggccccg tgtccggcat cttccagttc    120
tctgccagtc tgcacgtgga ccacagtgag ctgcagggca aggcccggct gcgggcccgg    180
gacgtggtgt gtgttctcat ctgtattgag tccctgtgcc agcgccacac gtgcctggag    240
gccgtctcag gcctggagag caacagcagg gtcttcacgc tacaggtgca ggggctgctg    300
cagctgcagg ctggacagta cgcttctgtg tttgtggaca atggctccgg ggccgtcctc    360
accatccagg cgggctccag cttctccggg ctgctcctgg gcacg                    405

<210> SEQ ID NO 14
<211> LENGTH: 135
<212> TYPE: PRT
<213> ORGANISM: Homo sapiens

<400> SEQUENCE: 14

Thr Leu Val Glu Leu His Gly Phe Gln Ala Pro Ala Ala Gln Gly Ala
1               5                   10                  15

Phe Leu Arg Gly Ser Gly Leu Ser Leu Ala Ser Gly Arg Phe Thr Ala
            20                  25                  30

Pro Val Ser Gly Ile Phe Gln Phe Ser Ala Ser Leu His Val Asp His
        35                  40                  45

Ser Glu Leu Gln Gly Lys Ala Arg Leu Arg Ala Arg Asp Val Val Cys
    50                  55                  60

Val Leu Ile Cys Ile Glu Ser Leu Cys Gln Arg His Thr Cys Leu Glu
65                  70                  75                  80

Ala Val Ser Gly Leu Glu Ser Asn Ser Arg Val Phe Thr Leu Gln Val
                85                  90                  95

Gln Gly Leu Leu Gln Leu Gln Ala Gly Gln Tyr Ala Ser Val Phe Val

-continued

```
                100                 105                 110

Asp Asn Gly Ser Gly Ala Val Leu Thr Ile Gln Ala Gly Ser Ser Phe
        115                 120                 125

Ser Gly Leu Leu Leu Gly Thr
        130                 135

<210> SEQ ID NO 15
<211> LENGTH: 864
<212> TYPE: DNA
<213> ORGANISM: Homo sapiens

<400> SEQUENCE: 15
gggggcgtcg ggccccggcg ggaggcacag aggacgcagc agcctggcca gcgcgcagat     60
ccccccaacg ccaccgccag cgcgtcctcc cgcgaggggc tgcccgaggc ccccaagcca    120
tcccaggcct caggacctga gttctccgac gcccacatga catggctgaa ctttgtccgg    180
cggccggaca cggcgccctt aaggaagcgg tgcggaagca gggacaagaa gccgcgggat    240
ctcttcggtc ccccaggacc tccaggtgca gaagtgaccg cggagactct gcttcacgag    300
tttcaggagc tgctgaaaga ggccacggag cgccggttct cagggcttct ggacccgctg    360
ctgccccagg gggcgggcct gcggctggtg ggcgaggcct ttcactgccg gctgcagggt    420
ccccgccggg tggacaagcg gacgctggtg gagctgcatg gtttccaggc tcctgctgcc    480
caaggtgcct tcctgcgagg ctccggtctg agcctggcct cgggtcggtt cacggccccc    540
gtgtccggca tcttccagtt ctctgccagt ctgcacgtgg accacagtga gctgcagggc    600
aaggcccggc tgcgggcccg ggacgtggtg tgtgttctca tctgtattga gtccctgtgc    660
cagcgccaca cgtgcctgga ggccgtctca ggcctggaga gcaacagcag ggtcttcacg    720
ctacaggtgc aggggctgct gcagctgcag gctggacagt acgcttctgt gtttgtggac    780
aatggctccg gggccgtcct caccatccag gcgggctcca gcttctccgg gctgctcctg    840
ggcacgcacc atcaccatca ccat                                           864

<210> SEQ ID NO 16
<211> LENGTH: 288
<212> TYPE: PRT
<213> ORGANISM: Homo sapiens

<400> SEQUENCE: 16

Gly Gly Val Gly Ala Arg Arg Glu Ala Gln Arg Thr Gln Gln Pro Gly
1               5                   10                  15

Gln Arg Ala Asp Pro Pro Asn Ala Thr Ala Ser Ala Ser Ser Arg Glu
            20                  25                  30

Gly Leu Pro Glu Ala Pro Lys Pro Ser Gln Ala Ser Gly Pro Glu Phe
        35                  40                  45

Ser Asp Ala His Met Thr Trp Leu Asn Phe Val Arg Arg Pro Asp Asp
    50                  55                  60

Gly Ala Leu Arg Lys Arg Cys Gly Ser Arg Asp Lys Lys Pro Arg Asp
65                  70                  75                  80

Leu Phe Gly Pro Pro Gly Pro Pro Gly Ala Glu Val Thr Ala Glu Thr
                85                  90                  95

Leu Leu His Glu Phe Gln Glu Leu Leu Lys Glu Ala Thr Glu Arg Arg
            100                 105                 110

Phe Ser Gly Leu Leu Asp Pro Leu Leu Pro Gln Gly Ala Gly Leu Arg
        115                 120                 125

Leu Val Gly Glu Ala Phe His Cys Arg Leu Gln Gly Pro Arg Arg Val
```

-continued

```
                130                 135                 140
Asp Lys Arg Thr Leu Val Glu Leu His Gly Phe Gln Ala Pro Ala Ala
145                 150                 155                 160

Gln Gly Ala Phe Leu Arg Gly Ser Gly Leu Ser Leu Ala Ser Gly Arg
                165                 170                 175

Phe Thr Ala Pro Val Ser Gly Ile Phe Gln Phe Ser Ala Ser Leu His
                180                 185                 190

Val Asp His Ser Glu Leu Gln Gly Lys Ala Arg Leu Arg Ala Arg Asp
                195                 200                 205

Val Val Cys Val Leu Ile Cys Ile Glu Ser Leu Cys Gln Arg His Thr
210                 215                 220

Cys Leu Glu Ala Val Ser Gly Leu Glu Ser Asn Ser Arg Val Phe Thr
225                 230                 235                 240

Leu Gln Val Gln Gly Leu Leu Gln Leu Gln Ala Gly Gln Tyr Ala Ser
                245                 250                 255

Val Phe Val Asp Asn Gly Ser Gly Ala Val Leu Thr Ile Gln Ala Gly
                260                 265                 270

Ser Ser Phe Ser Gly Leu Leu Leu Gly Thr His His His His His
                275                 280                 285
```

<210> SEQ ID NO 17
<211> LENGTH: 681
<212> TYPE: DNA
<213> ORGANISM: Homo sapiens

<400> SEQUENCE: 17

```
ccggacgacg gcgccttaag gaagcggtgc ggaagcaggg acaagaagcc gcgggatctc    60
ttcggtcccc caggacctcc aggtgcagaa gtgaccgcgg agactctgct tcacgagttt   120
caggagctgc tgaaagaggc cacggagcgc cggttctcag gcttctggac ccgctgctg   180
ccccagggg cgggcctgcg gctggtgggc gaggcctttc actgccggct gcagggtccc   240
cgccgggtgg acaagcggac gctggtggag ctgcatggtt tccaggctcc tgctgcccaa   300
ggtgccttcc tgcgaggctc cggtctgagc ctggcctcgg tcggttcac ggccccgtg    360
tccggcatct tccagttctc tgccagtctg cacgtggacc acagtgagct gcagggcaag   420
gcccggctgc gggcccggga cgtggtgtgt gttctcatct gtattgagtc cctgtgccag   480
cgccacacgt gcctggaggc cgtctcaggc ctggagagca acagcagggt cttcacgcta   540
caggtgcagg gctgctgca gctgcaggct ggacagtacg cttctgtgtt tgtggacaat    600
ggctccgggg ccgtcctcac catccaggcg ggctccagct tctccgggct gctcctgggc   660
acgcaccatc accatcacca t                                           681
```

<210> SEQ ID NO 18
<211> LENGTH: 227
<212> TYPE: PRT
<213> ORGANISM: Homo sapiens

<400> SEQUENCE: 18

```
Pro Asp Asp Gly Ala Leu Arg Lys Arg Cys Gly Ser Arg Asp Lys Lys
1               5                  10                  15

Pro Arg Asp Leu Phe Gly Pro Gly Pro Gly Ala Glu Val Thr
                20                  25                  30

Ala Glu Thr Leu Leu His Glu Phe Gln Glu Leu Leu Lys Glu Ala Thr
                35                  40                  45

Glu Arg Arg Phe Ser Gly Leu Leu Asp Pro Leu Leu Pro Gln Gly Ala
```

```
                50                  55                  60
Gly Leu Arg Leu Val Gly Glu Ala Phe His Cys Arg Leu Gln Gly Pro
 65                  70                  75                  80

Arg Arg Val Asp Lys Arg Thr Leu Val Glu Leu His Gly Phe Gln Ala
                 85                  90                  95

Pro Ala Ala Gln Gly Ala Phe Leu Arg Gly Ser Gly Leu Ser Leu Ala
            100                 105                 110

Ser Gly Arg Phe Thr Ala Pro Val Ser Gly Ile Phe Gln Phe Ser Ala
            115                 120                 125

Ser Leu His Val Asp His Ser Glu Leu Gln Gly Lys Ala Arg Leu Arg
        130                 135                 140

Ala Arg Asp Val Val Cys Val Leu Ile Cys Ile Glu Ser Leu Cys Gln
145                 150                 155                 160

Arg His Thr Cys Leu Glu Ala Val Ser Gly Leu Glu Ser Asn Ser Arg
                165                 170                 175

Val Phe Thr Leu Gln Val Gln Gly Leu Leu Gln Leu Ala Gly Gln
            180                 185                 190

Tyr Ala Ser Val Phe Val Asp Asn Gly Ser Gly Ala Val Leu Thr Ile
        195                 200                 205

Gln Ala Gly Ser Ser Phe Ser Gly Leu Leu Leu Gly Thr His His His
    210                 215                 220

His His His
225

<210> SEQ ID NO 19
<211> LENGTH: 660
<212> TYPE: DNA
<213> ORGANISM: Homo sapiens

<400> SEQUENCE: 19
aagcggtgcg gaagcaggga caagaagccg cgggatctct tcggtccccc aggacctcca      60
ggtgcagaag tgaccgcgga gactctgctt cacgagtttc aggagctgct gaaagaggcc    120
acggagcgcc ggttctcagg gcttctggac ccgctgctgc cccagggggc gggcctgcgg    180
ctggtgggcg aggcctttca ctgccggctg cagggtcccc gccgggtgga caagcggacg    240
ctggtggagc tgcatggttt ccaggctcct gctgcccaag gtgccttcct gcaggctcc    300 ggtctgagcc tggcctcggg tcggttcacg gccccgtgt ccggcatctt ccagttctct    360
gccagtctgc acgtggacca cagtgagctg cagggcaagg cccggctgcg ggcccgggac    420
gtggtgtgtg ttctcatctg tattgagtcc ctgtgccagc gccacacgtg cctggaggcc    480
gtctcaggcc tggagagcaa cagcagggtc ttcacgctac aggtgcaggg gctgctgcag    540
ctgcaggctg gacagtacgc ttctgtgttt gtggacaatg gctccggggc cgtcctcacc    600
atccaggcgg gctccagctt ctccgggctg ctcctgggca cgcaccatca ccatcaccat    660

<210> SEQ ID NO 20
<211> LENGTH: 220
<212> TYPE: PRT
<213> ORGANISM: Homo sapiens

<400> SEQUENCE: 20

Lys Arg Cys Gly Ser Arg Asp Lys Lys Pro Arg Asp Leu Phe Gly Pro
  1               5                  10                  15

Pro Gly Pro Pro Gly Ala Glu Val Thr Ala Glu Thr Leu Leu His Glu
             20                  25                  30
```

Phe Gln Glu Leu Leu Lys Glu Ala Thr Glu Arg Arg Phe Ser Gly Leu
            35                  40                  45

Leu Asp Pro Leu Leu Pro Gln Gly Ala Gly Leu Arg Leu Val Gly Glu
        50                  55                  60

Ala Phe His Cys Arg Leu Gln Gly Pro Arg Arg Val Asp Lys Arg Thr
65                  70                  75                  80

Leu Val Glu Leu His Gly Phe Gln Ala Pro Ala Gln Gly Ala Phe
                85                  90                  95

Leu Arg Gly Ser Gly Leu Ser Leu Ala Ser Gly Arg Phe Thr Ala Pro
                100                 105                 110

Val Ser Gly Ile Phe Gln Phe Ser Ala Ser Leu His Val Asp His Ser
            115                 120                 125

Glu Leu Gln Gly Lys Ala Arg Leu Arg Ala Arg Asp Val Val Cys Val
        130                 135                 140

Leu Ile Cys Ile Glu Ser Leu Cys Gln Arg His Thr Cys Leu Glu Ala
145                 150                 155                 160

Val Ser Gly Leu Glu Ser Asn Ser Arg Val Phe Thr Leu Gln Val Gln
                165                 170                 175

Gly Leu Leu Gln Leu Gln Ala Gly Gln Tyr Ala Ser Val Phe Val Asp
                180                 185                 190

Asn Gly Ser Gly Ala Val Leu Thr Ile Gln Ala Gly Ser Ser Phe Ser
                195                 200                 205

Gly Leu Leu Leu Gly Thr His His His His His His
                210                 215                 220

<210> SEQ ID NO 21
<211> LENGTH: 654
<212> TYPE: DNA
<213> ORGANISM: Homo sapiens

<400> SEQUENCE: 21
tgcggaagca gggacaagaa gccgcgggat ctcttcggtc ccccaggacc tccaggtgca     60
gaagtgaccg cggagactct gcttcacgag tttcaggagc tgctgaaaga ggccacggag    120
cgccggttct cagggcttct ggacccgctg ctgccccagg ggcgggcct gcggctggtg     180 ggcgaggcct ttcactgccg gctgcagggt ccccgccggg tggacaagcg acgctggtg    240 gagctgcatg gtttccaggc tcctgctgcc caaggtgcct cctgcgagg ctccggtctg    300 agcctggcct cgggtcggtt cacggccccc gtgtccggca tcttccagtt ctctgccagt    360
ctgcacgtgg accacagtga gctgcagggc aaggcccggc tgcgggcccg gacgtggtg    420 tgtgttctca tctgtattga gtccctgtgc cagcgccaca cgtgcctgga ggccgtctca    480
ggcctggaga gcaacagcag ggtcttcacg ctacaggtgc aggggctgct gcagctgcag    540
gctggacagt acgcttctgt gtttgtggac aatggctccg gggccgtcct caccatccag    600
gcgggctcca gcttctccgg gctgctcctg ggcacgcacc atcaccatca ccat          654

<210> SEQ ID NO 22
<211> LENGTH: 218
<212> TYPE: PRT
<213> ORGANISM: Homo sapiens

<400> SEQUENCE: 22

Cys Gly Ser Arg Asp Lys Lys Pro Arg Asp Leu Phe Gly Pro Pro Gly
1               5                   10                  15

Pro Pro Gly Ala Glu Val Thr Ala Glu Thr Leu Leu His Glu Phe Gln
                20                  25                  30

Glu Leu Leu Lys Glu Ala Thr Glu Arg Arg Phe Ser Gly Leu Leu Asp
                35                  40                  45

Pro Leu Leu Pro Gln Gly Ala Gly Leu Arg Leu Val Gly Glu Ala Phe
        50                  55                  60

His Cys Arg Leu Gln Gly Pro Arg Arg Val Asp Lys Arg Thr Leu Val
65                  70                  75                  80

Glu Leu His Gly Phe Gln Ala Pro Ala Ala Gln Gly Ala Phe Leu Arg
                85                  90                  95

Gly Ser Gly Leu Ser Leu Ala Ser Gly Arg Phe Thr Ala Pro Val Ser
            100                 105                 110

Gly Ile Phe Gln Phe Ser Ala Ser Leu His Val Asp His Ser Glu Leu
        115                 120                 125

Gln Gly Lys Ala Arg Leu Arg Ala Arg Asp Val Val Cys Val Leu Ile
    130                 135                 140

Cys Ile Glu Ser Leu Cys Gln Arg His Thr Cys Leu Glu Ala Val Ser
145                 150                 155                 160

Gly Leu Glu Ser Asn Ser Arg Val Phe Thr Leu Gln Val Gln Gly Leu
                165                 170                 175

Leu Gln Leu Gln Ala Gly Gln Tyr Ala Ser Val Phe Val Asp Asn Gly
        180                 185                 190

Ser Gly Ala Val Leu Thr Ile Gln Ala Gly Ser Ser Phe Ser Gly Leu
    195                 200                 205

Leu Leu Gly Thr His His His His His
210                 215

<210> SEQ ID NO 23
<211> LENGTH: 528
<212> TYPE: DNA
<213> ORGANISM: Homo sapiens

<400> SEQUENCE: 23
ttctcagggc ttctggaccc gctgctgccc caggggcgg gcctgcggct ggtgggcgag      60
gcctttcact gccggctgca gggtccccgc cgggtggaca gcggacgct ggtggagctg     120
catggtttcc aggctcctgc tgcccaaggt gccttcctgc gaggctccgg tctgagcctg     180
gcctcgggtc ggttcacggc ccccgtgtcc ggcatcttcc agttctctgc cagtctgcac     240
gtggaccaca gtgagctgca gggcaaggcc cggctgcggg cccgggacgt ggtgtgtgtt     300
ctcatctgta ttgagtccct gtgccagcgc cacacgtgcc tggaggccgt ctcaggcctg     360
gagagcaaca gcagggtctt cacgctacag gtgcaggggc tgctgcagct gcaggctgga     420
cagtacgctt ctgtgtttgt ggacaatggc tccggggccg tcctcaccat ccaggcgggc     480
tccagcttct ccgggctgct cctgggcacg caccatcacc atcaccat                 528

<210> SEQ ID NO 24
<211> LENGTH: 176
<212> TYPE: PRT
<213> ORGANISM: Homo sapiens

<400> SEQUENCE: 24

Phe Ser Gly Leu Leu Asp Pro Leu Leu Pro Gln Gly Ala Gly Leu Arg
1               5                   10                  15

Leu Val Gly Glu Ala Phe His Cys Arg Leu Gln Gly Pro Arg Arg Val
                20                  25                  30

Asp Lys Arg Thr Leu Val Glu Leu His Gly Phe Gln Ala Pro Ala Ala
        35                  40                  45

```
Gln Gly Ala Phe Leu Arg Gly Ser Gly Leu Ser Leu Ala Ser Gly Arg
         50                  55                  60
Phe Thr Ala Pro Val Ser Gly Ile Phe Gln Phe Ser Ala Ser Leu His
 65                  70                  75                  80
Val Asp His Ser Glu Leu Gln Gly Lys Ala Arg Leu Arg Ala Arg Asp
                 85                  90                  95
Val Val Cys Val Leu Ile Cys Ile Glu Ser Leu Cys Gln Arg His Thr
            100                 105                 110
Cys Leu Glu Ala Val Ser Gly Leu Glu Ser Asn Ser Arg Val Phe Thr
        115                 120                 125
Leu Gln Val Gln Gly Leu Leu Gln Leu Gln Ala Gly Gln Tyr Ala Ser
    130                 135                 140
Val Phe Val Asp Asn Gly Ser Gly Ala Val Leu Thr Ile Gln Ala Gly
145                 150                 155                 160
Ser Ser Phe Ser Gly Leu Leu Leu Gly Thr His His His His His
                165                 170                 175
```

<210> SEQ ID NO 25
<211> LENGTH: 435
<212> TYPE: DNA
<213> ORGANISM: Homo sapiens

<400> SEQUENCE: 25

```
gtggacaagc ggacgctggt ggagctgcat ggtttccagg ctcctgctgc ccaaggtgcc     60
ttcctgcgag gctccggtct gagcctggcc tcgggtcggt tcacggcccc cgtgtccggc    120
atcttccagt tctctgccag tctgcacgtg gaccacagtg agctgcaggg caaggcccgg    180
ctgcgggccc gggacgtggt gtgtgttctc atctgtattg agtccctgtg ccagcgccac    240
acgtgcctgg aggccgtctc aggcctggag agcaacagca gggtcttcac gctacaggtg    300
caggggctgc tgcagctgca ggctggacag tacgcttctg tgtttgtgga caatggctcc    360
ggggccgtcc tcaccatcca ggcgggctcc agcttctccg gctgctcct  gggcacgcac    420
catcaccatc accat                                                    435
```

<210> SEQ ID NO 26
<211> LENGTH: 145
<212> TYPE: PRT
<213> ORGANISM: Homo sapiens

<400> SEQUENCE: 26

```
Val Asp Lys Arg Thr Leu Val Glu Leu His Gly Phe Gln Ala Pro Ala
 1               5                  10                  15
Ala Gln Gly Ala Phe Leu Arg Gly Ser Gly Leu Ser Leu Ala Ser Gly
             20                  25                  30
Arg Phe Thr Ala Pro Val Ser Gly Ile Phe Gln Phe Ser Ala Ser Leu
         35                  40                  45
His Val Asp His Ser Glu Leu Gln Gly Lys Ala Arg Leu Arg Ala Arg
     50                  55                  60
Asp Val Val Cys Val Leu Ile Cys Ile Glu Ser Leu Cys Gln Arg His
 65                  70                  75                  80
Thr Cys Leu Glu Ala Val Ser Gly Leu Glu Ser Asn Ser Arg Val Phe
                 85                  90                  95
Thr Leu Gln Val Gln Gly Leu Leu Gln Leu Gln Ala Gly Gln Tyr Ala
            100                 105                 110
Ser Val Phe Val Asp Asn Gly Ser Gly Ala Val Leu Thr Ile Gln Ala
```

-continued

```
                115                 120                 125
Gly Ser Ser Phe Ser Gly Leu Leu Leu Gly Thr His His His His
    130                 135                 140
His
145
```

<210> SEQ ID NO 27
<211> LENGTH: 423
<212> TYPE: DNA
<213> ORGANISM: Homo sapiens

<400> SEQUENCE: 27

```
acgctggtgg agctgcatgg tttccaggct cctgctgccc aaggtgcctt cctgcgaggc    60
tccggtctga gcctggcctc gggtcggttc acggcccccg tgtccggcat cttccagttc   120
tctgccagtc tgcacgtgga ccacagtgag ctgcagggca aggcccggct gcgggcccgg   180
gacgtggtgt gtgttctcat ctgtattgag tccctgtgcc agcgccacac gtgcctggag   240
gccgtctcag gcctggagag caacagcagg gtcttcacgc tacaggtgca ggggctgctg   300
cagctgcagg ctggacagta cgcttctgtg tttgtggaca atggctccgg ggccgtcctc   360
accatccagg cgggctccag cttctccggg ctgctcctgg gcacgcacca tcaccatcac   420
cat                                                                 423
```

<210> SEQ ID NO 28
<211> LENGTH: 141
<212> TYPE: PRT
<213> ORGANISM: Homo sapiens

<400> SEQUENCE: 28

```
Thr Leu Val Glu Leu His Gly Phe Gln Ala Pro Ala Ala Gln Gly Ala
1               5                   10                  15
Phe Leu Arg Gly Ser Gly Leu Ser Leu Ala Ser Gly Arg Phe Thr Ala
            20                  25                  30
Pro Val Ser Gly Ile Phe Gln Phe Ser Ala Ser Leu His Val Asp His
        35                  40                  45
Ser Glu Leu Gln Gly Lys Ala Arg Leu Arg Ala Arg Asp Val Val Cys
    50                  55                  60
Val Leu Ile Cys Ile Glu Ser Leu Cys Gln Arg His Thr Cys Leu Glu
65                  70                  75                  80
Ala Val Ser Gly Leu Glu Ser Asn Ser Arg Val Phe Thr Leu Gln Val
                85                  90                  95
Gln Gly Leu Leu Gln Leu Gln Ala Gly Gln Tyr Ala Ser Val Phe Val
            100                 105                 110
Asp Asn Gly Ser Gly Ala Val Leu Thr Ile Gln Ala Gly Ser Ser Phe
        115                 120                 125
Ser Gly Leu Leu Leu Gly Thr His His His His His
    130                 135                 140
```

<210> SEQ ID NO 29
<211> LENGTH: 906
<212> TYPE: DNA
<213> ORGANISM: Homo sapiens

<400> SEQUENCE: 29

```
atgcggcgct gggcctgggc cgcggtcgtg gtcctcctcg gccgcagct cgtgctcctc    60
gggggcgtcg gggcccggcg ggaggcacag aggacgcagc agcctggcca gcgcgcagat   120
```

```
cccccccaacg ccaccgccag cgcgtcctcc cgcgagggc tgcccgaggc ccccaagcca      180
tcccaggcct caggacctga gttctccgac gcccacatga catggctgaa ctttgtccgg      240
cggccggacg acggcgcctt aaggaagcgg tgcggaagca gggacaagaa gccgcgggat      300
ctcttcggtc ccccaggacc tccaggtgca gaagtgaccg cggagactct gcttcacgag      360
tttcaggagc tgctgaaaga ggccacggag cgccggttct cagggcttct ggacccgctg      420
ctgccccagg gggcgggcct gcggctggtg ggcgaggcct tcactgccg gctgcagggt      480 ccccgccggg tggacaagcg gacgctggtg gagctgcatg gtttccaggc tcctgctgcc      540
caaggtgcct tcctgcgagg ctccggtctg agcctggcct cgggtcggtt cacggccccc      600
gtgtccggca tcttccagtt ctctgccagt ctgcacgtgg accacagtga gctgcagggc      660
aaggcccggc tgcgggcccg ggacgtggtg tgtgttctca tctgtattga gtccctgtgc      720
cagcgccaca cgtgcctgga ggccgtctca ggcctggaga gcaacagcag ggtcttcacg      780
ctacaggtgc aggggctgct gcagctgcag gctggacagt acgcttctgt gtttgtggac      840
aatggctccg gggccgtcct caccatccag gcgggctcca gcttctccgg gctgctcctg      900
ggcacg                                                                906

<210> SEQ ID NO 30
<211> LENGTH: 302
<212> TYPE: PRT
<213> ORGANISM: Homo sapiens

<400> SEQUENCE: 30

Met Arg Arg Trp Ala Trp Ala Ala Val Val Leu Leu Gly Pro Gln
 1               5                  10                  15

Leu Val Leu Leu Gly Gly Val Gly Ala Arg Arg Glu Ala Gln Arg Thr
                20                  25                  30

Gln Gln Pro Gly Gln Arg Ala Asp Pro Pro Asn Ala Thr Ala Ser Ala
            35                  40                  45

Ser Ser Arg Glu Gly Leu Pro Glu Ala Pro Lys Pro Ser Gln Ala Ser
        50                  55                  60

Gly Pro Glu Phe Ser Asp Ala His Met Thr Trp Leu Asn Phe Val Arg
65                  70                  75                  80

Arg Pro Asp Asp Gly Ala Leu Arg Lys Arg Cys Gly Ser Arg Asp Lys
                85                  90                  95

Lys Pro Arg Asp Leu Phe Gly Pro Pro Gly Pro Pro Gly Ala Glu Val
            100                 105                 110

Thr Ala Glu Thr Leu Leu His Glu Phe Gln Glu Leu Leu Lys Glu Ala
        115                 120                 125

Thr Glu Arg Arg Phe Ser Gly Leu Leu Asp Pro Leu Leu Pro Gln Gly
    130                 135                 140

Ala Gly Leu Arg Leu Val Gly Glu Ala Phe His Cys Arg Leu Gln Gly
145                 150                 155                 160

Pro Arg Arg Val Asp Lys Arg Thr Leu Val Glu Leu His Gly Phe Gln
                165                 170                 175

Ala Pro Ala Ala Gln Gly Ala Phe Leu Arg Gly Ser Gly Leu Ser Leu
            180                 185                 190

Ala Ser Gly Arg Phe Thr Ala Pro Val Ser Gly Ile Phe Gln Phe Ser
        195                 200                 205

Ala Ser Leu His Val Asp His Ser Glu Leu Gln Gly Lys Ala Arg Leu
    210                 215                 220

Arg Ala Arg Asp Val Val Cys Val Leu Ile Cys Ile Glu Ser Leu Cys
```

```
                225                 230                 235                 240
Gln Arg His Thr Cys Leu Glu Ala Val Ser Gly Leu Glu Ser Asn Ser
                245                 250                 255

Arg Val Phe Thr Leu Gln Val Gln Gly Leu Leu Gln Leu Gln Ala Gly
                260                 265                 270

Gln Tyr Ala Ser Val Phe Val Asp Asn Gly Ser Gly Ala Val Leu Thr
                275                 280                 285

Ile Gln Ala Gly Ser Ser Phe Ser Gly Leu Leu Leu Gly Thr
                290                 295                 300
```

<210> SEQ ID NO 31
<211> LENGTH: 924
<212> TYPE: DNA
<213> ORGANISM: Homo sapiens

<400> SEQUENCE: 31

| | | | | | |
|---|---|---|---|---|---|
| atgcggcgct | gggcctgggc | cgcggtcgtg | gtcctcctcg | gccgcagct | cgtgctcctc | 60 |
| gggggcgtcg | ggcccggcg | ggaggcacag | aggacgcagc | agcctggcca | gcgcgcagat | 120 |
| ccccccaacg | ccaccgccag | cgcgtcctcc | cgcgaggggc | tgcccgaggc | ccccaagcca | 180 |
| tcccaggcct | caggacctga | gttctccgac | gcccacatga | catggctgaa | ctttgtccgg | 240 |
| cggccggaca | cggcgccctt | aaggaagcgg | tgcggaagca | gggacaagaa | gccgcgggat | 300 |
| ctcttcggtc | ccccaggacc | tccaggtgca | gaagtgaccg | cggagactct | gcttcacgag | 360 |
| tttcaggagc | tgctgaaaga | ggccacggag | cgccggttct | cagggcttct | ggacccgctg | 420 |
| ctgccccagg | gggcgggcct | gcggctggtg | ggcgaggcct | ttcactgccg | gctgcagggt | 480 |
| ccccgccggg | tggacaagcg | gacgctggtg | gagctgcatg | gtttccaggc | tcctgctgcc | 540 |
| caaggtgcct | tcctgcgagg | ctccggtctg | agcctggcct | cgggtcggtt | cacggccccc | 600 |
| gtgtccggca | tcttccagtt | ctctgccagt | ctgcacgtgg | accacagtga | gctgcagggc | 660 |
| aaggcccggc | tgcgggcccg | ggacgtggtg | tgtgttctca | tctgtattga | gtccctgtgc | 720 |
| cagcgccaca | cgtgcctgga | ggccgtctca | ggcctggaga | gcaacagcag | ggtcttcacg | 780 |
| ctacaggtgc | aggggctgct | gcagctgcag | gctggacagt | acgcttctgt | gtttgtggac | 840 |
| aatggctccg | gggccgtcct | caccatccag | gcgggctcca | gcttctccgg | gctgctcctg | 900 |
| ggcacgcacc | atcaccatca | ccat | | | | 924 |

<210> SEQ ID NO 32
<211> LENGTH: 308
<212> TYPE: PRT
<213> ORGANISM: Homo sapiens

<400> SEQUENCE: 32

```
Met Arg Arg Trp Ala Trp Ala Ala Val Val Val Leu Leu Gly Pro Gln
1               5                   10                  15

Leu Val Leu Leu Gly Gly Val Gly Ala Arg Arg Glu Ala Gln Arg Thr
                20                  25                  30

Gln Gln Pro Gly Gln Arg Ala Asp Pro Pro Asn Ala Thr Ala Ser Ala
            35                  40                  45

Ser Ser Arg Glu Gly Leu Pro Glu Ala Pro Lys Pro Ser Gln Ala Ser
        50                  55                  60

Gly Pro Glu Phe Ser Asp Ala His Met Thr Trp Leu Asn Phe Val Arg
65                  70                  75                  80

Arg Pro Asp Asp Gly Ala Leu Arg Lys Arg Cys Gly Ser Arg Asp Lys
                85                  90                  95
```

Lys Pro Arg Asp Leu Phe Gly Pro Pro Gly Pro Pro Gly Ala Glu Val
            100                 105                 110

Thr Ala Glu Thr Leu Leu His Glu Phe Gln Glu Leu Leu Lys Glu Ala
        115                 120                 125

Thr Glu Arg Arg Phe Ser Gly Leu Leu Asp Pro Leu Leu Pro Gln Gly
    130                 135                 140

Ala Gly Leu Arg Leu Val Gly Glu Ala Phe His Cys Arg Leu Gln Gly
145                 150                 155                 160

Pro Arg Arg Val Asp Lys Arg Thr Leu Val Glu Leu His Gly Phe Gln
                165                 170                 175

Ala Pro Ala Ala Gln Gly Ala Phe Leu Arg Gly Ser Gly Leu Ser Leu
            180                 185                 190

Ala Ser Gly Arg Phe Thr Ala Pro Val Ser Gly Ile Phe Gln Phe Ser
        195                 200                 205

Ala Ser Leu His Val Asp His Ser Glu Leu Gln Gly Lys Ala Arg Leu
    210                 215                 220

Arg Ala Arg Asp Val Val Cys Val Leu Ile Cys Ile Glu Ser Leu Cys
225                 230                 235                 240

Gln Arg His Thr Cys Leu Glu Ala Val Ser Gly Leu Glu Ser Asn Ser
                245                 250                 255

Arg Val Phe Thr Leu Gln Val Gln Gly Leu Leu Gln Leu Gln Ala Gly
            260                 265                 270

Gln Tyr Ala Ser Val Phe Val Asp Asn Gly Ser Gly Ala Val Leu Thr
        275                 280                 285

Ile Gln Ala Gly Ser Ser Phe Ser Gly Leu Leu Leu Gly Thr His His
    290                 295                 300

His His His His
305

<210> SEQ ID NO 33
<211> LENGTH: 831
<212> TYPE: DNA
<213> ORGANISM: Homo sapiens

<400> SEQUENCE: 33
cggcgggagg cacagaggac gcagcagcct ggccagcgcg cagatccccc caacgccacc      60
gccagcgcgt cctcccgcga ggggctgccc gaggccccca agccatccca ggcctcagga     120
cctgagttct ccgacgccca catgacatgg ctgaactttg tccggcggcc ggacgacggc     180
gccttaagga agcggtgcgg aagcagggac aagaagccgc gggatctctt cggtccccca     240
ggacctccag gtgcagaagt gaccgcggag actctgcttc acgagtttca ggagctgctg     300
aaagaggcca cggagcgccg gttctcaggg cttctggacc cgctgctgcc caggggggcg     360
ggcctgcggc tggtgggcga ggcctttcac tgccggctgc agggtccccg ccgggtggac     420
aagcggacgc tggtggagct gcatggtttc caggctcctg ctgcccaagg tgccttcctg     480
cgaggctccg gtctgagcct ggcctcgggt cggttcacgg cccccgtgtc cggcatcttc     540
cagttctctg ccagtctgca cgtggaccac agtgagctgc agggcaaggc ccggctgcgg     600
gcccgggacg tggtgtgtgt tctcatctgt attgagtccc tgtgccagcg ccacacgtgc     660
ctggaggccg tctcaggcct ggagagcaac agcagggtct tcacgctaca ggtgcagggg     720
ctgctgcagc tgcaggctgg acagtacgct tctgtgtttg tggacaatgg ctccggggcc     780
gtcctcacca tccaggcggg ctccagcttc tccgggctgc tcctgggcac g              831

<210> SEQ ID NO 34
<211> LENGTH: 277
<212> TYPE: PRT
<213> ORGANISM: Homo sapiens

<400> SEQUENCE: 34

Arg Arg Glu Ala Gln Arg Thr Gln Gln Pro Gly Gln Arg Ala Asp Pro
1               5                   10                  15

Pro Asn Ala Thr Ala Ser Ala Ser Ser Arg Glu Gly Leu Pro Glu Ala
            20                  25                  30

Pro Lys Pro Ser Gln Ala Ser Gly Pro Glu Phe Ser Asp Ala His Met
        35                  40                  45

Thr Trp Leu Asn Phe Val Arg Arg Pro Asp Asp Gly Ala Leu Arg Lys
    50                  55                  60

Arg Cys Gly Ser Arg Asp Lys Lys Pro Arg Asp Leu Phe Gly Pro Pro
65                  70                  75                  80

Gly Pro Pro Gly Ala Glu Val Thr Ala Glu Thr Leu Leu His Glu Phe
                85                  90                  95

Gln Glu Leu Leu Lys Glu Ala Thr Glu Arg Arg Phe Ser Gly Leu Leu
            100                 105                 110

Asp Pro Leu Leu Pro Gln Gly Ala Gly Leu Arg Leu Val Gly Glu Ala
        115                 120                 125

Phe His Cys Arg Leu Gln Gly Pro Arg Arg Val Asp Lys Arg Thr Leu
    130                 135                 140

Val Glu Leu His Gly Phe Gln Ala Pro Ala Ala Gln Gly Ala Phe Leu
145                 150                 155                 160

Arg Gly Ser Gly Leu Ser Leu Ala Ser Gly Arg Phe Thr Ala Pro Val
                165                 170                 175

Ser Gly Ile Phe Gln Phe Ser Ala Ser Leu His Val Asp His Ser Glu
            180                 185                 190

Leu Gln Gly Lys Ala Arg Leu Arg Ala Arg Asp Val Val Cys Val Leu
        195                 200                 205

Ile Cys Ile Glu Ser Leu Cys Gln Arg His Thr Cys Leu Glu Ala Val
    210                 215                 220

Ser Gly Leu Glu Ser Asn Ser Arg Val Phe Thr Leu Gln Val Gln Gly
225                 230                 235                 240

Leu Leu Gln Leu Gln Ala Gly Gln Tyr Ala Ser Val Phe Val Asp Asn
                245                 250                 255

Gly Ser Gly Ala Val Leu Thr Ile Gln Ala Gly Ser Ser Phe Ser Gly
            260                 265                 270

Leu Leu Leu Gly Thr
        275

<210> SEQ ID NO 35
<211> LENGTH: 849
<212> TYPE: DNA
<213> ORGANISM: Homo sapiens

<400> SEQUENCE: 35
cggcgggagg cacagaggac gcagcagcct ggccagcgcg cagatccccc caacgccacc      60
gccagcgcgt cctcccgcga ggggctgccc gaggccccca gccatccca ggcctcagga     120 cctgagttct ccgacgccca catgacatgg ctgaactttg tccggcggcc ggacgacggc     180
gccttaagga agcggtgcgg aagcagggac aagaagccgc gggatctctt cggtccccca     240
ggacctccag gtgcagaagt gaccgcggag actctgcttc acgagtttca ggagctgctg     300

```
aaagaggcca cggagcgccg gttctcaggg cttctggacc cgctgctgcc ccagggggcg    360
ggcctgcggc tggtgggcga ggcctttcac tgccggctgc agggtccccg ccgggtggac    420
aagcggacgc tggtggagct gcatggtttc caggctcctg ctgcccaagg tgccttcctg    480
cgaggctccg gtctgagcct ggcctcgggt cggttcacgg ccccgtgtc cggcatcttc      540 cagttctctg ccagtctgca cgtggaccac agtgagctgc agggcaaggc ccggctgcgg    600
gcccgggacg tggtgtgtgt tctcatctgt attgagtccc tgtgccagcg ccacacgtgc    660
ctggaggccg tctcaggcct ggagagcaac agcagggtct tcacgctaca ggtgcagggg    720
ctgctgcagc tgcaggctgg acagtacgct tctgtgtttg tggacaatgg ctccggggcc    780
gtcctcacca tccaggcggg ctccagcttc tccgggctgc tcctgggcac gcaccatcac    840
catcaccat                                                            849
```

<210> SEQ ID NO 36
<211> LENGTH: 283
<212> TYPE: PRT
<213> ORGANISM: Homo sapiens

<400> SEQUENCE: 36

```
Arg Arg Glu Ala Gln Arg Thr Gln Gln Pro Gly Gln Arg Ala Asp Pro
1               5                   10                  15

Pro Asn Ala Thr Ala Ser Ala Ser Ser Arg Glu Gly Leu Pro Glu Ala
            20                  25                  30

Pro Lys Pro Ser Gln Ala Ser Gly Pro Glu Phe Ser Asp Ala His Met
        35                  40                  45

Thr Trp Leu Asn Phe Val Arg Arg Pro Asp Asp Gly Ala Leu Arg Lys
    50                  55                  60

Arg Cys Gly Ser Arg Asp Lys Lys Pro Arg Asp Leu Phe Gly Pro Pro
65                  70                  75                  80

Gly Pro Pro Gly Ala Glu Val Thr Ala Glu Thr Leu Leu His Glu Phe
                85                  90                  95

Gln Glu Leu Leu Lys Glu Ala Thr Glu Arg Arg Phe Ser Gly Leu Leu
            100                 105                 110

Asp Pro Leu Leu Pro Gln Gly Ala Gly Leu Arg Leu Val Gly Glu Ala
        115                 120                 125

Phe His Cys Arg Leu Gln Gly Pro Arg Arg Val Asp Lys Arg Thr Leu
    130                 135                 140

Val Glu Leu His Gly Phe Gln Ala Pro Ala Gln Gly Ala Phe Leu
145                 150                 155                 160

Arg Gly Ser Gly Leu Ser Leu Ala Ser Gly Arg Phe Thr Ala Pro Val
                165                 170                 175

Ser Gly Ile Phe Gln Phe Ser Ala Ser Leu His Val Asp His Ser Glu
            180                 185                 190

Leu Gln Gly Lys Ala Arg Leu Arg Ala Arg Asp Val Val Cys Val Leu
        195                 200                 205

Ile Cys Ile Glu Ser Leu Cys Gln Arg His Thr Cys Leu Glu Ala Val
    210                 215                 220

Ser Gly Leu Glu Ser Asn Ser Arg Val Phe Thr Leu Gln Val Gln Gly
225                 230                 235                 240

Leu Leu Gln Leu Gln Ala Gly Gln Tyr Ala Ser Val Phe Val Asp Asn
                245                 250                 255

Gly Ser Gly Ala Val Leu Thr Ile Gln Ala Gly Ser Ser Phe Ser Gly
            260                 265                 270
```

Leu Leu Leu Gly Thr His His His His His His
      275                 280

<210> SEQ ID NO 37
<211> LENGTH: 24
<212> TYPE: DNA
<213> ORGANISM: Artificial Sequence
<220> FEATURE:
<223> OTHER INFORMATION: Primer INSP163-CP1

<400> SEQUENCE: 37
tgagccgcct cgggacggag ccat                                        24

<210> SEQ ID NO 38
<211> LENGTH: 24
<212> TYPE: DNA
<213> ORGANISM: Artificial Sequence
<220> FEATURE:
<223> OTHER INFORMATION: Primer INSP163-CP2

<400> SEQUENCE: 38
acgtgcccag gagcagcccg gaga                                        24

<210> SEQ ID NO 39
<211> LENGTH: 35
<212> TYPE: DNA
<213> ORGANISM: Artificial Sequence
<220> FEATURE:
<223> OTHER INFORMATION: Primer INSP163-EX1

<400> SEQUENCE: 39
gcaggcttcg ccaccatgcg gcgctgggcc tgggc                            35

<210> SEQ ID NO 40
<211> LENGTH: 35
<212> TYPE: DNA
<213> ORGANISM: Artificial Sequence
<220> FEATURE:
<223> OTHER INFORMATION: Primer INSP163-EX2

<400> SEQUENCE: 40
tgatggtgat ggtgcgtgcc caggagcagc ccgga                            35

<210> SEQ ID NO 41
<211> LENGTH: 37
<212> TYPE: DNA
<213> ORGANISM: Artificial Sequence
<220> FEATURE:
<223> OTHER INFORMATION: Primer GCP Forward

<400> SEQUENCE: 41
ggggacaagt ttgtacaaaa aagcaggctt cgccacc                          37

<210> SEQ ID NO 42
<211> LENGTH: 51
<212> TYPE: DNA
<213> ORGANISM: Artificial Sequence
<220> FEATURE:
<223> OTHER INFORMATION: Primer GCP Reverse

<400> SEQUENCE: 42
ggggaccact ttgtacaaga aagctgggtt tcaatggtga tggtgatggt g           51

<210> SEQ ID NO 43
<211> LENGTH: 20

```
<212> TYPE: DNA
<213> ORGANISM: Artificial Sequence
<220> FEATURE:
<223> OTHER INFORMATION: Primer pEAK12F

<400> SEQUENCE: 43
gccagcttgg cacttgatgt                                              20

<210> SEQ ID NO 44
<211> LENGTH: 20
<212> TYPE: DNA
<213> ORGANISM: Artificial Sequence
<220> FEATURE:
<223> OTHER INFORMATION: Primer pEAK12R

<400> SEQUENCE: 44
gatggaggtg gacgtgtcag                                              20

<210> SEQ ID NO 45
<211> LENGTH: 18
<212> TYPE: DNA
<213> ORGANISM: Artificial Sequence
<220> FEATURE:
<223> OTHER INFORMATION: Primer 21M13

<400> SEQUENCE: 45
tgtaaaacga cggccagt                                                18

<210> SEQ ID NO 46
<211> LENGTH: 18
<212> TYPE: DNA
<213> ORGANISM: Artificial Sequence
<220> FEATURE:
<223> OTHER INFORMATION: Primer M13REV

<400> SEQUENCE: 46
caggaaacag ctatgacc                                                18

<210> SEQ ID NO 47
<211> LENGTH: 19
<212> TYPE: DNA
<213> ORGANISM: Artificial Sequence
<220> FEATURE:
<223> OTHER INFORMATION: Primer T7

<400> SEQUENCE: 47
taatacgact cactatagg                                               19

<210> SEQ ID NO 48
<211> LENGTH: 18
<212> TYPE: DNA
<213> ORGANISM: Artificial Sequence
<220> FEATURE:
<223> OTHER INFORMATION: Primer T3

<400> SEQUENCE: 48
attaaccctc actaaagg                                                18

<210> SEQ ID NO 49
<211> LENGTH: 929
<212> TYPE: DNA
<213> ORGANISM: Homo sapiens
<220> FEATURE:
<221> NAME/KEY: exon
<222> LOCATION: (23)..(929)

<400> SEQUENCE: 49
```

```
                                                    -continued tgagccgcct cgggacggag cc atg cgg cgc tgg gcc tgg gcc gcg gtc gtg        52
                        Met Arg Arg Trp Ala Trp Ala Ala Val Val
                         1               5                  10 gtc ctc ctc ggg ccg cag ctg gtg ctc ctc ggg ggc gtc ggg gcc cgg        100
Val Leu Leu Gly Pro Gln Leu Val Leu Leu Gly Gly Val Gly Ala Arg
                 15                  20                  25 cgg gag gca cag agg acg cag cag cct ggc cag cgc gca gat ccc ccc        148
Arg Glu Ala Gln Arg Thr Gln Gln Pro Gly Gln Arg Ala Asp Pro Pro
             30                  35                  40 aac gcc acc gcc agc gcg tcc tcc cgc gag ggg ctg ccc gag gcc ccc        196
Asn Ala Thr Ala Ser Ala Ser Ser Arg Glu Gly Leu Pro Glu Ala Pro
         45                  50                  55 aag cca tcc cag gcc tca gga cct gag ttc tcc gac gcc cac atg aca        244
Lys Pro Ser Gln Ala Ser Gly Pro Glu Phe Ser Asp Ala His Met Thr
     60                  65                  70 tgg ctg aac ttt gtc cgg cgg ccg gac gac ggc gcc tta agg aag cgg        292
Trp Leu Asn Phe Val Arg Arg Pro Asp Asp Gly Ala Leu Arg Lys Arg
 75                  80                  85                  90 tgc gga agc agg gac aag aag ccg cgg gat ctc ttc ggt ccc cca gga        340
Cys Gly Ser Arg Asp Lys Lys Pro Arg Asp Leu Phe Gly Pro Pro Gly
                 95                 100                 105 cct cca ggt gca gaa gtg acc gcg gag act ctg ctt cac gag ttt cag        388
Pro Pro Gly Ala Glu Val Thr Ala Glu Thr Leu Leu His Glu Phe Gln
            110                 115                 120 gag ctg ctg aaa gag gcc acg gag cgc cgg ttc tca ggg ctt ctg gac        436
Glu Leu Leu Lys Glu Ala Thr Glu Arg Arg Phe Ser Gly Leu Leu Asp
        125                 130                 135 ccg ctg ctg ccc cag ggg gcg ggc ctg cgg ctg gtg ggc gag gcc ttt        484
Pro Leu Leu Pro Gln Gly Ala Gly Leu Arg Leu Val Gly Glu Ala Phe
    140                 145                 150 cac tgc cgg ctg cag ggt ccc gcc cgg gtg gac aag cgg acg ctg gtg        532
His Cys Arg Leu Gln Gly Pro Arg Arg Val Asp Lys Arg Thr Leu Val
155                 160                 165                 170 gag ctg cat ggt ttc cag gct cct gct gcc caa ggt gcc ttc ctg cga        580
Glu Leu His Gly Phe Gln Ala Pro Ala Ala Gln Gly Ala Phe Leu Arg
                175                 180                 185 ggc tcc ggt ctg agc ctg gcc tcg ggt cgg ttc acg gcc ccc gtg tcc        628
Gly Ser Gly Leu Ser Leu Ala Ser Gly Arg Phe Thr Ala Pro Val Ser
            190                 195                 200 ggc atc ttc cag ttc tct gcc agt ctg cac gtg gac cac agt gag ctg        676
Gly Ile Phe Gln Phe Ser Ala Ser Leu His Val Asp His Ser Glu Leu
        205                 210                 215 cag ggc aag gcc cgg ctg cgg gcc cgg gac gtg gtg tgt gtt ctc atc        724
Gln Gly Lys Ala Arg Leu Arg Ala Arg Asp Val Val Cys Val Leu Ile
    220                 225                 230 tgt att gag tcc ctg tgc cag cgc cac acg tgc ctg gag gcc gtc tca        772
Cys Ile Glu Ser Leu Cys Gln Arg His Thr Cys Leu Glu Ala Val Ser
235                 240                 245                 250 ggc ctg gag agc aac agc agg gtc ttc acg cta cag gtg cag ggg ctg        820
Gly Leu Glu Ser Asn Ser Arg Val Phe Thr Leu Gln Val Gln Gly Leu
                255                 260                 265 ctg cag ctg cag gct gga cag tac gct tct gtg ttt gtg gac aat ggc        868
Leu Gln Leu Gln Ala Gly Gln Tyr Ala Ser Val Phe Val Asp Asn Gly
            270                 275                 280 tcc ggg gcc gtc ctc acc atc cag gcg ggc tcc agc ttc tcc ggg ctg        916
Ser Gly Ala Val Leu Thr Ile Gln Ala Gly Ser Ser Phe Ser Gly Leu
        285                 290                 295
```

```
ctc ctg ggc acg t                                                       929
Leu Leu Gly Thr
    300
```